United States Patent [19]
Fenster et al.

[11] Patent Number: 5,454,371
[45] Date of Patent: Oct. 3, 1995

[54] METHOD AND SYSTEM FOR CONSTRUCTING AND DISPLAYING THREE-DIMENSIONAL IMAGES

[75] Inventors: Aaron Fenster; Shane Dunne; Thomas K. C. Chan; Donal Downey, all of London, Canada

[73] Assignee: London Health Association, London, Canada

[21] Appl. No.: 264,800

[22] Filed: Jun. 23, 1994

Related U.S. Application Data

[63] Continuation-in-part of Ser. No. 158,267, Nov. 29, 1993, abandoned.

[51] Int. Cl.$^6$ ..................................................... A61B 8/00
[52] U.S. Cl. ..................... 128/660.07; 128/916; 395/119
[58] Field of Search ......................... 128/660.07, 660.08, 128/660.09, 660.10, 661.01, 916; 364/413.22, 413.19; 395/162, 163, 119; 382/6, 44, 45, 46

[56] References Cited

U.S. PATENT DOCUMENTS

| | | | |
|---|---|---|---|
| 4,763,661 | 8/1988 | Sommer et al. | 128/660 |
| 4,945,478 | 7/1990 | Merickel et al. | 364/413.22 |
| 5,159,931 | 11/1992 | Pini | 128/660.07 |
| 5,170,347 | 12/1992 | Tuy et al. | 364/413.22 |
| 5,201,035 | 4/1993 | Stytz et al. | 395/163 |

FOREIGN PATENT DOCUMENTS

| | | | |
|---|---|---|---|
| 0514584 | 11/1992 | European Pat. Off. | A61B 8/00 |
| 3610439 | 10/1987 | Germany | A61B 8/08 |
| 9103792 | 3/1991 | WIPO . | |
| 9400052 | 1/1994 | WIPO . | |

OTHER PUBLICATIONS

Three–Dimensional Sonographic Reconstruction:Techniques and Diagnostic Applications, Richard N. Rankin, et al. AJR (1993); 161:pp. 695–702.

Three–Dimensional Colour Doppler Imaging, Paul A. Picot, et al., Ultrasound in Med. & Biology, vol. 19, No. 2, pp. 95–104, (1993).

Three–Dimensional Colour Doppler Imaging Of The Carotid Artery, Paul A. Picot, et al., SPIE, vol. 1444, pp. 206–213 (1991).

New scans from old: digital reformatting of ultrasound images, M. Halliwell, pp. 824–829; Multidimensional Ultrasonic Imaging for Cardiology, Hugh A. McCann, et al.; 3–D Ultrasound Angiograms from Color Flow Mapping Images, J. Goddard, et al.

*Primary Examiner*—George Manuel
*Attorney, Agent, or Firm*—Fitzpatrick, Cella, Harper & Scinto

[57] ABSTRACT

A three-dimensional ultrasound imaging system includes an ultrasound probe to direct ultrasound waves to and to receive reflected ultrasound waves from a target volume of a subject under examination. The ultrasound probe is swept over the target volume and the reflected ultrasound waves are conveyed to a computer wherein successive two-dimensional images of the target volume are reconstructed to form a three-dimensional image of the target volume. The three-dimensional image is displayed on the monitor of the computer. A user interface allows a user to manipulate the displayed image. Specifically, the entire displayed image may be rotated about an arbitrary axis, a surface of the displayed image may be translated to provide different cross-sectional views of the image and a selected surface of the displayed image may be rotated about an arbitrary axis. All of these manipulations can be achieved via a single graphical input device such as a mouse connected to the computer.

32 Claims, 41 Drawing Sheets

+ ASSUME THE SCAN PROBE IS AT THE TOP OR BOTTOM OF THE IMAGES. IF IT IS ON THE LEFT OR RIGHT OF THE IMAGES, THE TRANSFORMATION WILL BE $f:(x,y,z) \rightarrow (Y-y,z,x)$ WHERE $Y$ IS THE $y$-DIMENSION OF THE IMAGES.

[ ] - SEE RECONSTRUCTION DIAGRAMS IN FIGURES 10 TO 13

[ ] - SEE RECONSTRUCTION DIAGRAMS IN FIGURES 14 TO 18a

[ ] - SEE RECONSTRUCTION DIAGRAMS IN FIGURES 14 TO 16b AND 18a

[ ] - SEE RECONSTRUCTION DIAGRAMS IN FIGURES 16a TO 16c

[ ] - SEE RECONSTRUCTION DIAGRAMS IN FIGURES 16a AND 16b

[I] Types of hardwares offsets considered

*Image-tilt Offset*

*Displacement Offset*

[T] Types of hardware offsets considered(cont'd)

*Tilting Offset*

[II] Rotate $I(x,y,z)$ to eliminate image-tilt effect

*Geometry for eliminating image-tilt effect* image-tilt angle $\beta$

*Or, if image tilts to the other side* image-tilt angle $\beta$

[III] Transformation of $I'(x,y,z)$ to $R(x,y,z)$

[IV] Create temporary raster $T(x,y)$ $T(x,y)$
—buffer to hold z-slice of reconstructed image $V(x,y,z)$.

[V] Extract a z-slice $A(x,y)$ of $R(x,y,z)$

[VI] Compute pertaining offset of A(x,y)

*Geometry for calculating tilting offset*

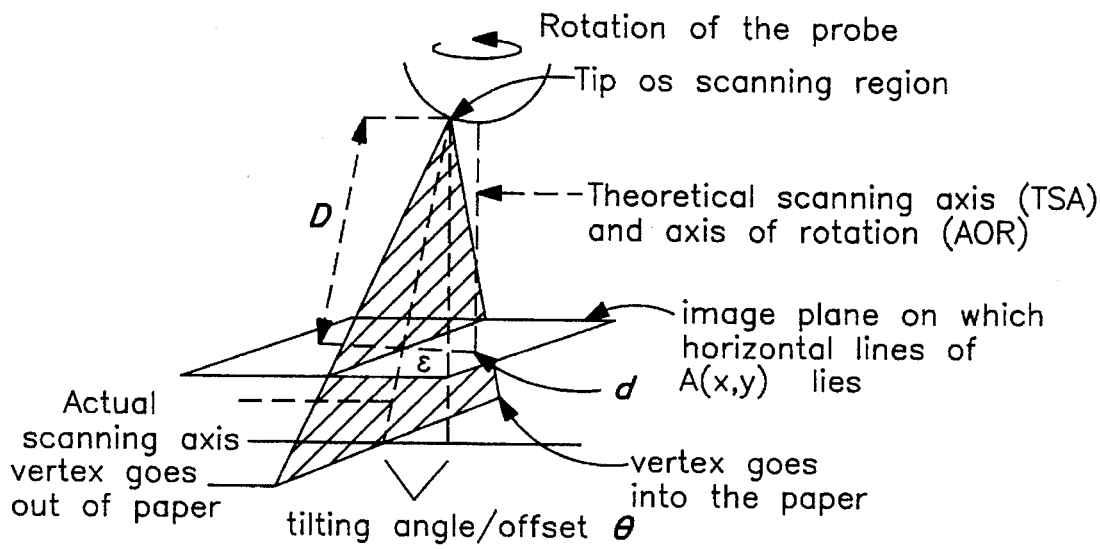

$d$ = displacement offset $D$ = distance from the tip of scanning region to A(x,y)

$\varepsilon = D * \text{SIN}(\theta)$

Pertaining offset $p = d + \varepsilon$

Note: $\varepsilon$ is negative if the actual scanning axis tilts inwards (relative to the direction of rotation), and $d$ is negative if the actual scanning axis is "behind" the theoretical scanning axis (relative to the direction of rotation).

FIG. 15

[VIII] Compute the position of A(x,y) in T(x,y)

$a$ Angle of rotation
$p$ Pertaining offset
$A(i_c,j)$ pixel of $A(x,j)$ closest to the axis of rotation The position of $A(0,j)$ in $T$ is $(r_x, r_y)$, with $$r_x = C_x - i_c * \cos(a) + p * \sin(a)$$
$$r_y = C_y - i_c * \sin(a) + p * \cos(a)$$

Subsequent positions of $A(x,j)$ are acquired by incrementing $r_x$ by $\cos(a)$, and decrementing $r_y$ by $\sin(a)$.

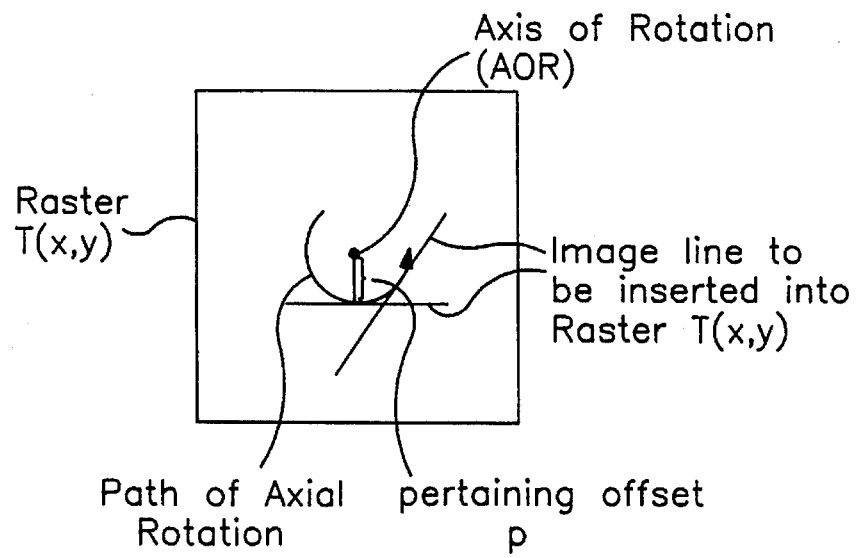
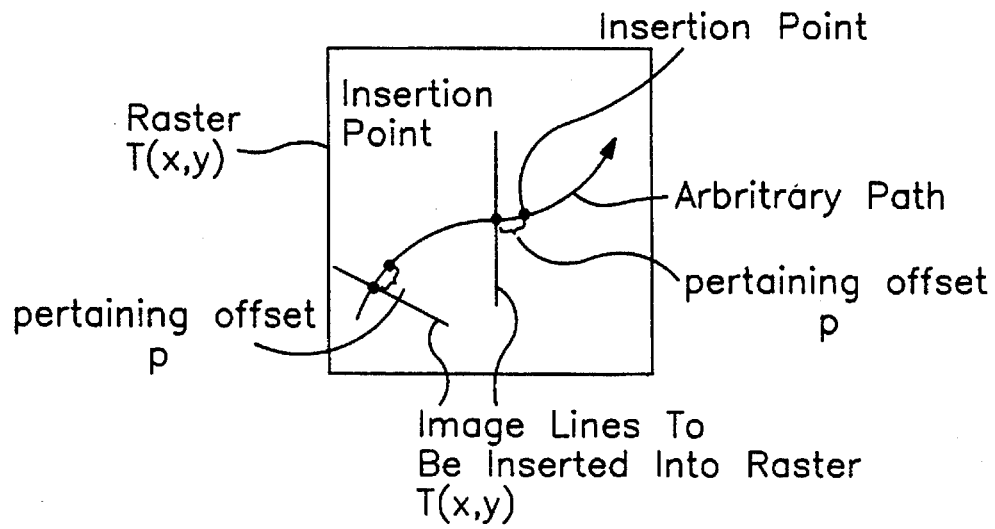
FIG. 18b

METHOD AND SYSTEM FOR CONSTRUCTING AND DISPLAYING THREE-DIMENSIONAL IMAGES

RELATED APPLICATIONS

The present application is a continuation-in-part of U.S. patent application Ser. No. 08/158,267 filed on Nov. 29, 1993 now abandoned for an invention entitled "Three-Dimensional Ultrasound Imaging System".

FIELD OF THE INVENTION

The present invention relates to medical diagnostics and in particular to a method and system for constructing and displaying three-dimensional images and to a system for displaying three-dimensional images.

BACKGROUND OF THE INVENTION

In the medical field, it is common to use ultrasound diagnostic equipment to view internal organs of a subject. For example, in diagnosing prostate cancer, a diagnostician uses transrectal ultrasound (TRUS) to identify whether lesions are present as well as to determine the location, size and extent of lesions if present. Conventional ultrasound diagnostic equipment typically comprise an ultrasound probe for transmitting ultrasound signals into the subject and receiving reflected ultrasound signals therefrom. The reflected ultrasound signals received by the ultrasound probe are processed and a two-dimensional image of the target under examination is formed.

Unfortunately, this conventional equipment produces two-dimensional images even though the target under examination is three-dimensional. Also, the two-dimensional images represent a single thin plane taken at an arbitrary angle to the target making it very difficult to localize the image plane in the target and very difficult to reproduce a particular image location at a later time.

In U.S application Ser. No. 08/158,267, assigned to the assignee of the present application, a three-dimensional ultrasound imaging system is described. Although, this system overcomes disadvantages associated with the prior art, improvements to enhance imaging are continually being sought.

It is therefore an object of the present invention to provide a novel system and method for generating a three-dimensional image from a succession of two-dimensional images, a novel system for allowing a user to manipulate a displayed three-dimensional image, and a novel ultrasound imaging system.

SUMMARY OF THE INVENTION

According to one aspect of the present invention there is provided a method and system for converting two-dimensional images of a target volume represented by an array of pixels $I(x,y,z)$ into a three-dimensional image represented by a volumetric image array $V(x,y,z)$. Specifically, the method comprises the steps of:

(i) transforming said array of pixels $I(x,y,z)$ into an image array $R(x,y,z)$ so that each z-slice $A(x,y)$ of image array $R(x,y,z)$ provides sufficient image data to construct an image slice;

(ii) extracting a z-slice $A(x,y)$ of image array $R(x,y,z)$ and computing the position of each pixel of z-slice $A(x,y)$ in a volumetric image array $V(x,y,z)$;

(iii) mapping a gray-level or color value for the pixels of z-slice $A(x,y)$ into corresponding pixels of said volumetric image array; (iv) repeating steps (ii) and (iii) until all z-slices $A(x,y)$ of image array $R(x,y,z)$ have been processed to complete said volumetric image array; and (v) compensating for at least one hardware offset affecting said volumetric image array which occurred when said two-dimensional images were taken.

In another aspect of the present invention there is provided a three-dimensional imaging system for acquiring a succession of two-dimensional images of a target volume represented by an array of pixels $I(x,y,z)$ into a three-dimensional image represented by a volumetric image array $V(x,y,z)$ comprising:

scanning means to scan said target volume and generate a succession of two-dimensional images thereof; and processing means in communication with said scanning means, said processing means including:

means to convert the two-dimensional images of the target volume into an array of pixels $I(x,y,z)$;

means to transform said array of pixels $I(x,y,z)$ into an image array $R(x,y,z)$ so that each z-slice $A(x,y)$ of image array $R(x,y,z)$ provides sufficient image data to construct an image slice;

means to extract each z-slice $A(x,y)$ of image array $R(x,y,z)$ and compute the position of each pixel of each z-slice $A(x,y)$ in a volumetric image array;

means to compute and store a gray level or color for each of the pixels of each z-slice $A(x,y)$;

means to map the computed gray-levels or colors into corresponding pixels of said volumetric image array $V(x,y,z)$; and means to compensate for at least one hardware offset affecting said array of pixels associated with said scanning means.

In yet another aspect of the present invention there is provided a system for displaying and manipulating a displayed three-dimensional image represented by a volumetric image array $V(x,y,z)$, said three-dimensional image having a plurality of surfaces, at least one of which is visible on a display at any given time, said system comprising:

means to contextually interpret actuation of a user input device to detect a desired manipulation of said displayed image selected from a group of desired manipulations including (i) rotation of said displayed image about an arbitrary axis; (ii) translation of a selected visible surface of said image along an axis; and (iii) rotation of a visible surface about an axis; and processing means in communication with said detection means, said processing means acting on said volumetric image array in response to the user input device and updating said displayed image in accordance with the selected desired manipulated thereof.

In still yet another aspect of the present invention there is provided a three-dimensional imaging system for generating a three-dimensional image of a target volume under examination, said system comprising:

scanning means to transmit signals to said target volume, to scan said entire target volume; and a processor in communication with said scanning means and receiving output signals therefrom, said processor reconstructing a volumetric image array $V(x,y,z)$ representing a three-dimensional image of said target volume from said output signals, said processor establishing a model in the form of a convex polyhedron having a plurality of planes which encompasses substantially said volumetric image array, said processor mapping said image array onto said model to form a displayed three-dimensional image having a plurality of surfaces, at least one of which is visible on said display at any given time, said processor including:

detection means to contextually interpret actuation of a user input device to detect a desired manipulation of said displayed image selected from a group of desired manipulations including (i) rotation of said displayed image about an arbitrary axis; (ii) translation of a selected plane of said image; and (iii) rotation of a selected plane of said image about an arbitrary axis; and means in communication with said detection means, to act on said volumetric image array in response to the user input device and update said displayed image in accordance with the selected desired manipulated thereof.

BRIEF DESCRIPTION OF THE DRAWINGS

The file of this patent contains at least one drawing executed in color. Copies of this patent with color drawings will be provided by the Patent and Trademark Office upon request and payment of the necessary fee.

Embodiments of the present invention will now be described more fully with reference to the accompanying drawings in which:

FIGS. 11a and 11b show a method of removing the hardware offset illustrated in FIG. 10a;

FIG. 15 shows a method of determining the pertaining offset contributed by hardware offsets illustrated in FIGS. 10b and 10c;

FIG. 18b are reconstruction diagrams showing the contents of a temporary raster for axial rotation and arbitrary path geometries;

DESCRIPTION OF THE PREFERRED EMBODIMENTS

Figure 1:
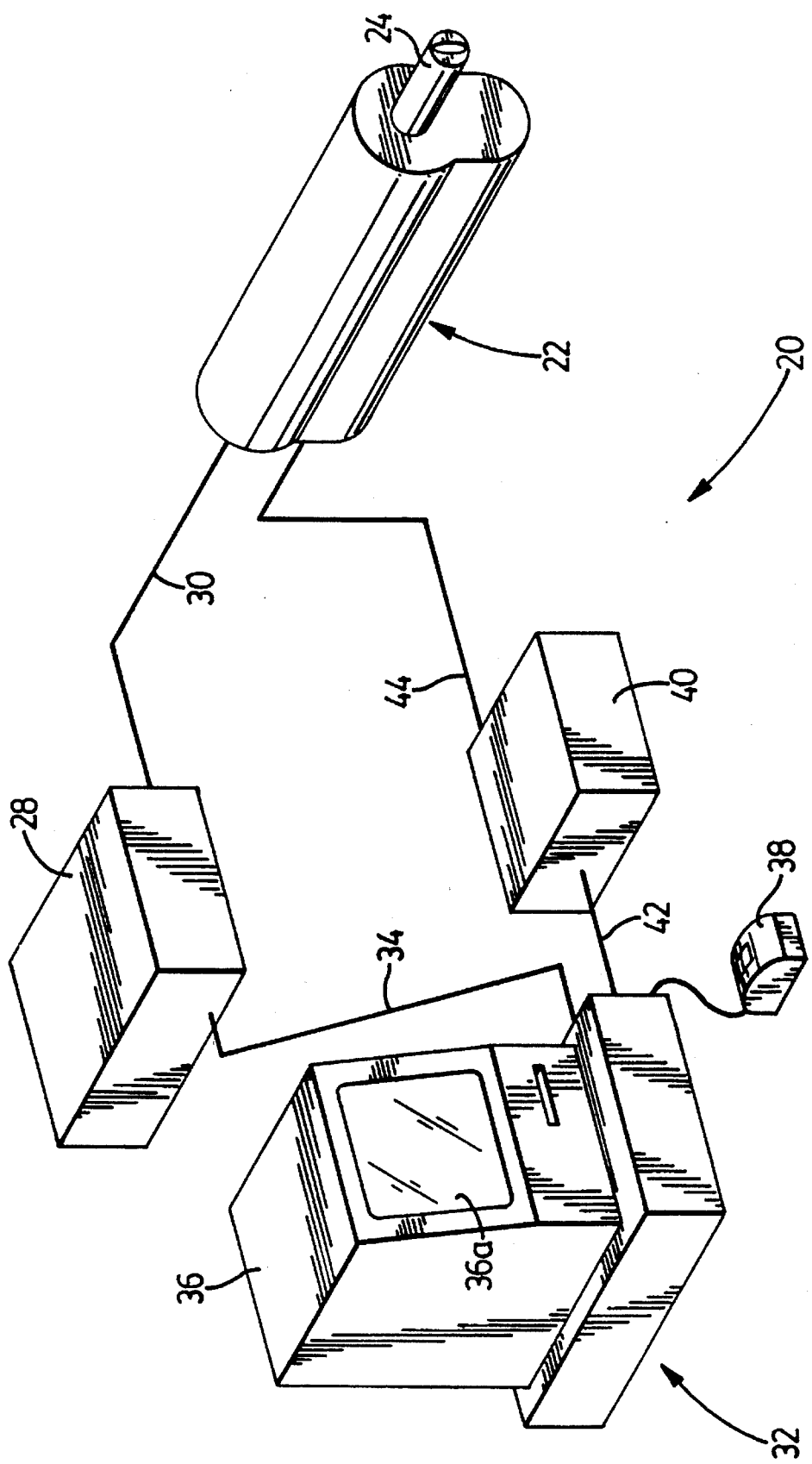
FIG. 1 is a perspective view of a three-dimensional ultrasound imaging system.

Referring now to FIG. 1, a three-dimensional ultrasound imaging system is shown and is generally indicated by reference numeral 20. The system 20 is capable of generating a three-dimensional ultrasound image of a target volume of a subject under examination from a succession of two-dimensional ultrasound images of the target volume and allow the generated three-dimensional image to be manipulated. The subject under examination may be inanimate or animate. In the later case, the system 20 may be used in both medical and veterinary environments and may be used as a diagnostic tool or during surgery to provide updated images of the target volume undergoing surgery.

The system 20 includes an ultrasound probe actuating assembly 22 for removably retaining an ultrasound probe 24. The probe actuating assembly 22 is designed to move the ultrasound probe through a predetermined angular sweep so that the succession of two-dimensional images of the target volume can be taken.

The ultrasound probe 24 is connected to a clinical ultrasound machine 28 via a communication line 30. The ultrasound machine 28 in turn is connected to a computer 32 via communication line 34. The computer 32 includes a keyboard (not shown), a monitor 36 with a display screen 36a and a graphical input device 38 such as a single button mouse. It should however be realized that many other graphical input devices can be used to allow a user to input commands to the computer. The computer 32 provides output signals to a controller 40 via communication line 42 which in turn provides control signals to the probe actuating assembly 22 via communication line 44.

Figure 2:
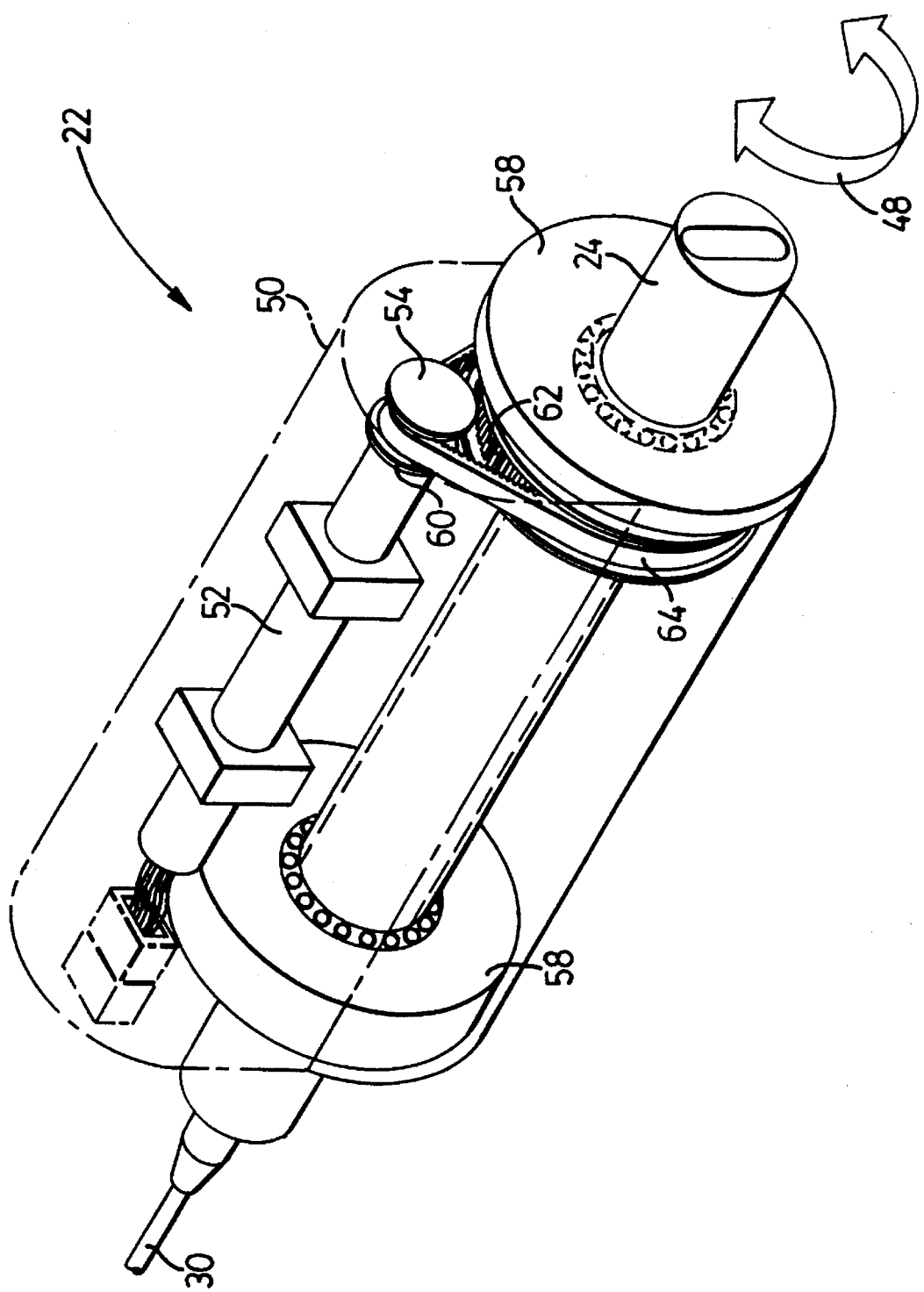
FIG. 2 is a perspective view of an ultrasound probe and probe actuating assembly forming part of the system illustrated in FIG. 1.
Figure 3:
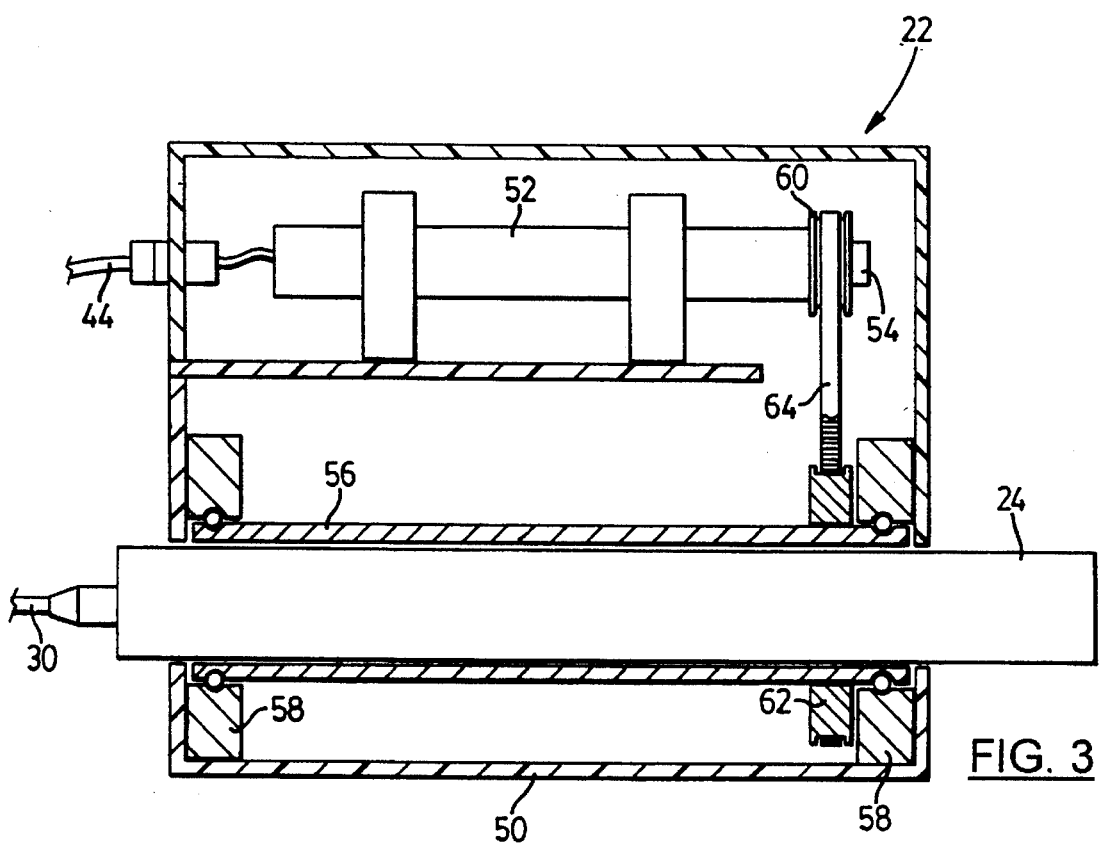
FIG. 3 is a sectional view of the probe actuating assembly illustrated in FIG. 2.
Figure 4:
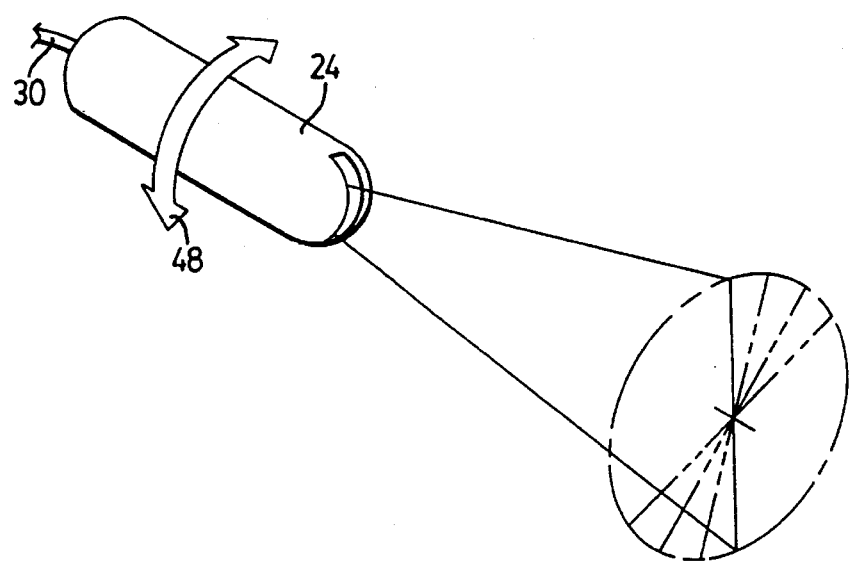
FIG. 4 is a perspective view of the geometry of the ultrasound probe movement when driven by the probe actuating assembly illustrated in FIG. 2.

Referring now to FIGS. 2 to 4, the ultrasound probe 24 and probe actuating assembly 22 are better illustrated. In this particular example, the ultrasound probe 24 is of the end-firing type and is rotated axially by the probe actuating assembly 22 to obtain the succession of two-dimensional ultrasound images of the target volume. This motion of the ultrasound probe is indicated by arrow 48. The probe actuating assembly 22 includes an external housing 50 in which a motor 52 is located. The motor is preferably a precision servo-motor which rotates with a substantially constant angular velocity. Thus, when the succession of two-dimensional ultrasound images are acquired, the images are taken at equally spaced, angular intervals. An output shaft 54 extends from the motor 52. The ultrasound probe 24 is held securely in a barrel 56 which itself is supported by a pair of ball bearing mounts 58. Gear reduction wheels 60 and 62 are connected to the output shaft 54 and the barrel 56 respectively. A belt 64 translates rotary motion of the output shaft 54 to the barrel 56 and hence, to the ultrasound probe 24 in a reciprocating circular motion. Thus, the volume swept by the ultrasound probe 24 is generally conical. This ultrasound probe 24 and probe actuating assembly 22 are particularly useful for scanning organs of a subject under examination, such as the eye or the prostate.

The ultrasound probe 24 during its sweep transmits ultrasound signals which impinge on the target volume. Reflected ultrasound signals from the target volume are also received by the probe 24 and are converted into analog signals by a crystal (not shown) in the ultrasound probe 24. These analog signals are conveyed to the clinical ultrasound machine 28 where a succession of two-dimensional analog images of the target volume are generated. This operation of the ultrasound probe 24 and clinical ultrasound machine 28 is well known to those of skill in the art and therefore, will not be described in any further detail herein.

The two-dimensional analog images generated by the ultrasound machine 28 are conveyed to the computer 32 via communication line 34. The computer 32 in turn constructs a three-dimensional image of the target volume from the succession of two-dimensional images. Once the three-dimensional image has been created, the computer 32 allows the three-dimensional image to be displayed and manipulated as will be described.

Figure 5:
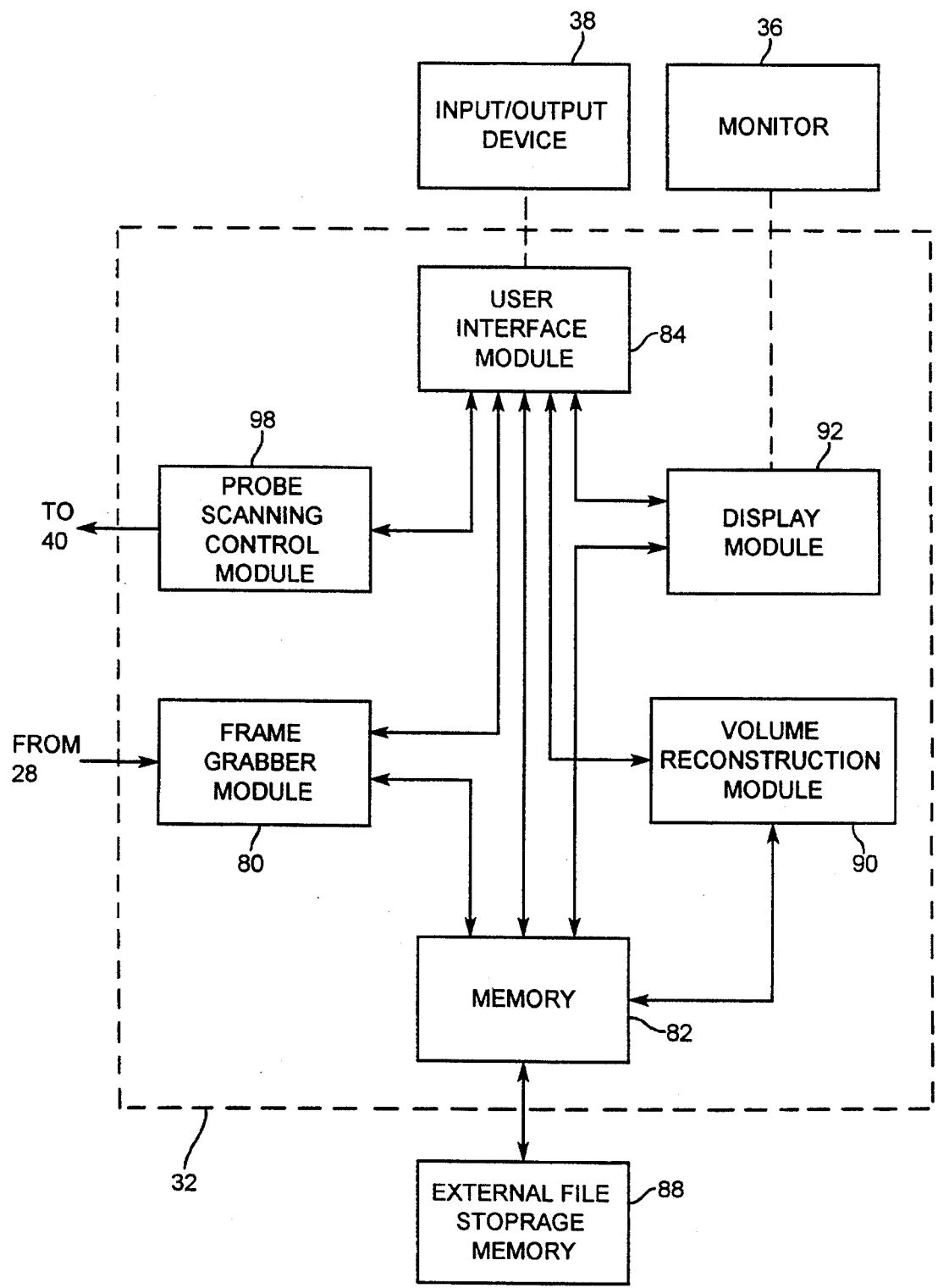
FIG. 5 is a block diagram showing various hardware and software modules of the computer forming part of the system illustrated in FIG. 1.

Referring now to FIG. 5, a block diagram of the computer 32 is shown illustrating some of the hardware and software modules therein. As can be seen, the computer 32 includes a frame grabber module 80, such as for example, an IMAXX Video Capture Board with appropriate software manufactured by Precision Digital Images Corporation of Redmond, Washington, to process the two-dimensional analog images received from the clinical ultrasound machine 28 via communication line 34. Specifically, the frame grabber module 80 captures and digitizes the succession of two-dimensional analog images. Once digitized, the succession of two-dimensional images is stored in memory 82.

The computer 32 also includes a user interface module 84 for interpreting input commands received via the graphical input device 38. As should be realized, the user interface module 84 controls and co-ordinates the operation of the other modules of system 20 in response to input from the graphical input device 38 allowing the user to control the system as desired.

Once a succession of two-dimensional images of the target volume has been captured and digitized by frame grabber module 80 and stored in the memory 82, the digitized information can be processed in a number of ways depending on the input commands received by the user interface module 84 from the graphical input device 38. Specifically, the digitized information can be transferred to an external file storage memory 88. Alternatively, the digitized information can be processed by a volume reconstruction module 90 to form a volumetric image array V(x,y,z) representing a three-dimensional image of the target volume. Once created, the volumetric image array is stored in the external file storage memory 88. Alternatively, the volumetric image array may be further processed by a display module 92 in response to input received from graphical input device 38 so that a three-dimensional image of the target volume can be displayed on the screen 36a of the monitor 36 and manipulated as will be described further herein.

The computer 32 also includes a probe scanning control module 98 which provides output signals to controller 40 to actuate the probe actuating assembly 22 as desired. The probe scanning control module 98 also receives input from the user interface module 84.

Image Capturing

Figure 6A:
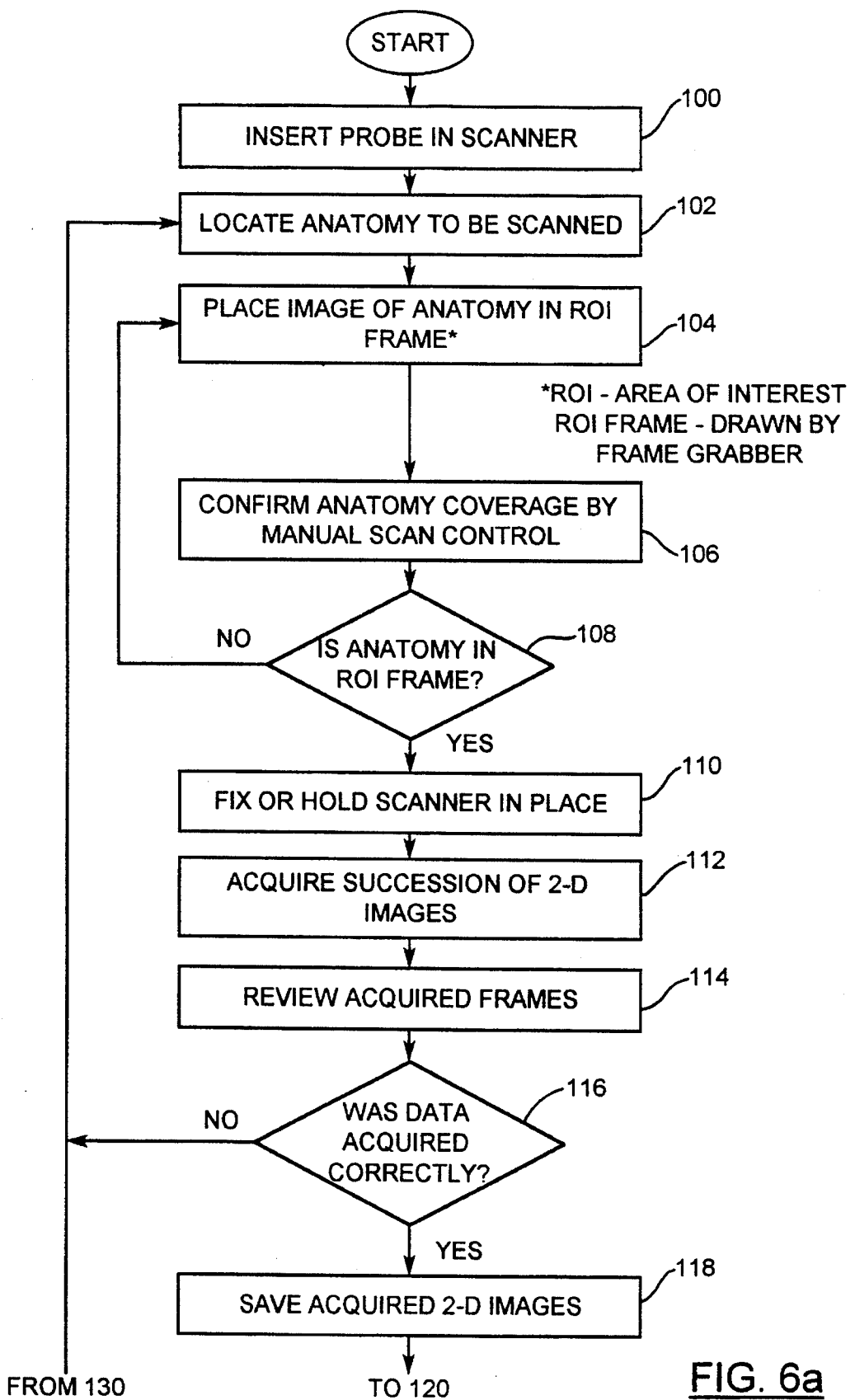
FIG. 6a is a flowchart showing some of the operational steps of the system illustrated in FIG. 1.
Figure 6B:
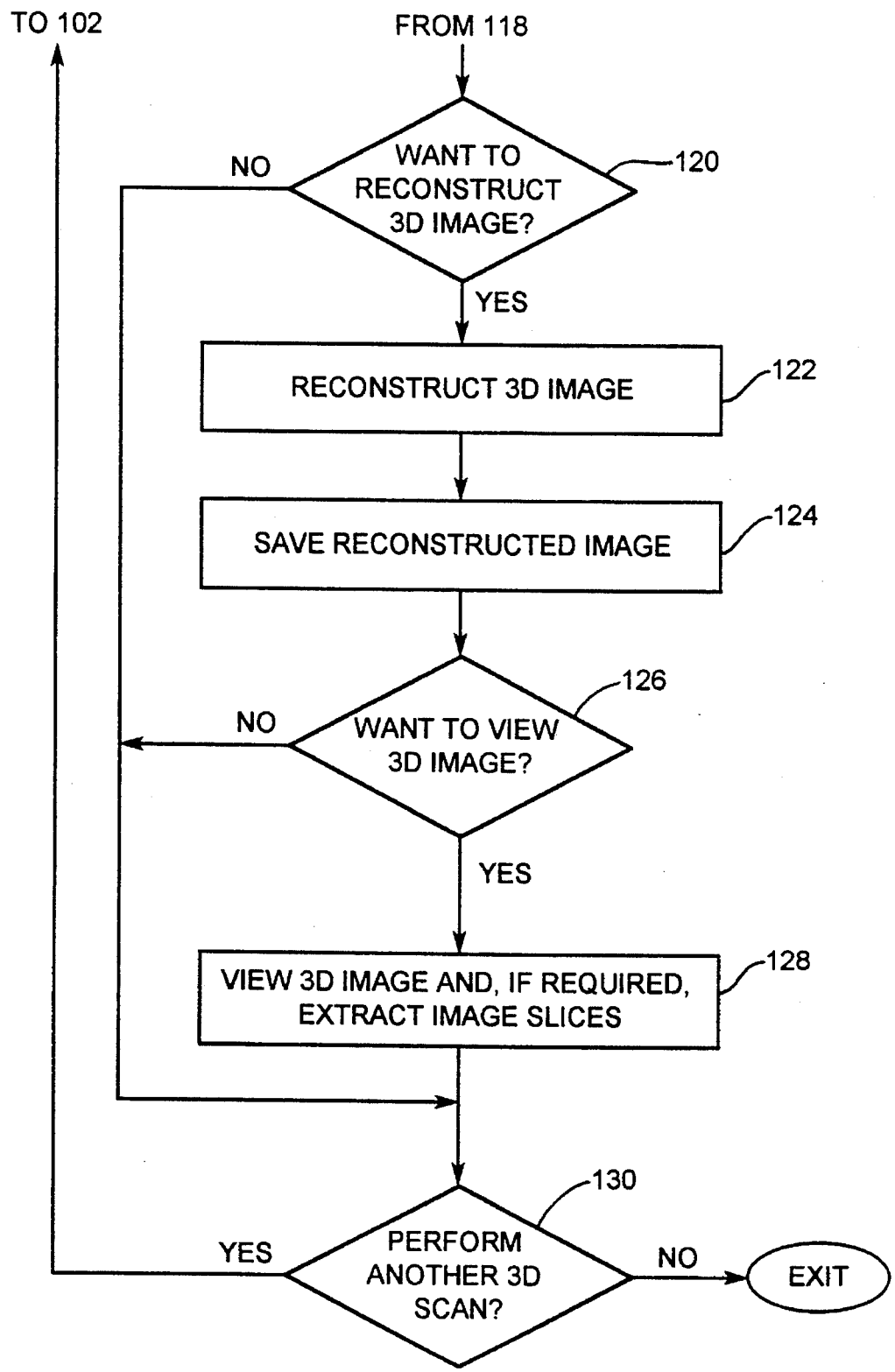
FIG. 6b is a flowchart showing additional operational steps of the system illustrated in FIG. 1.
Figure 7:
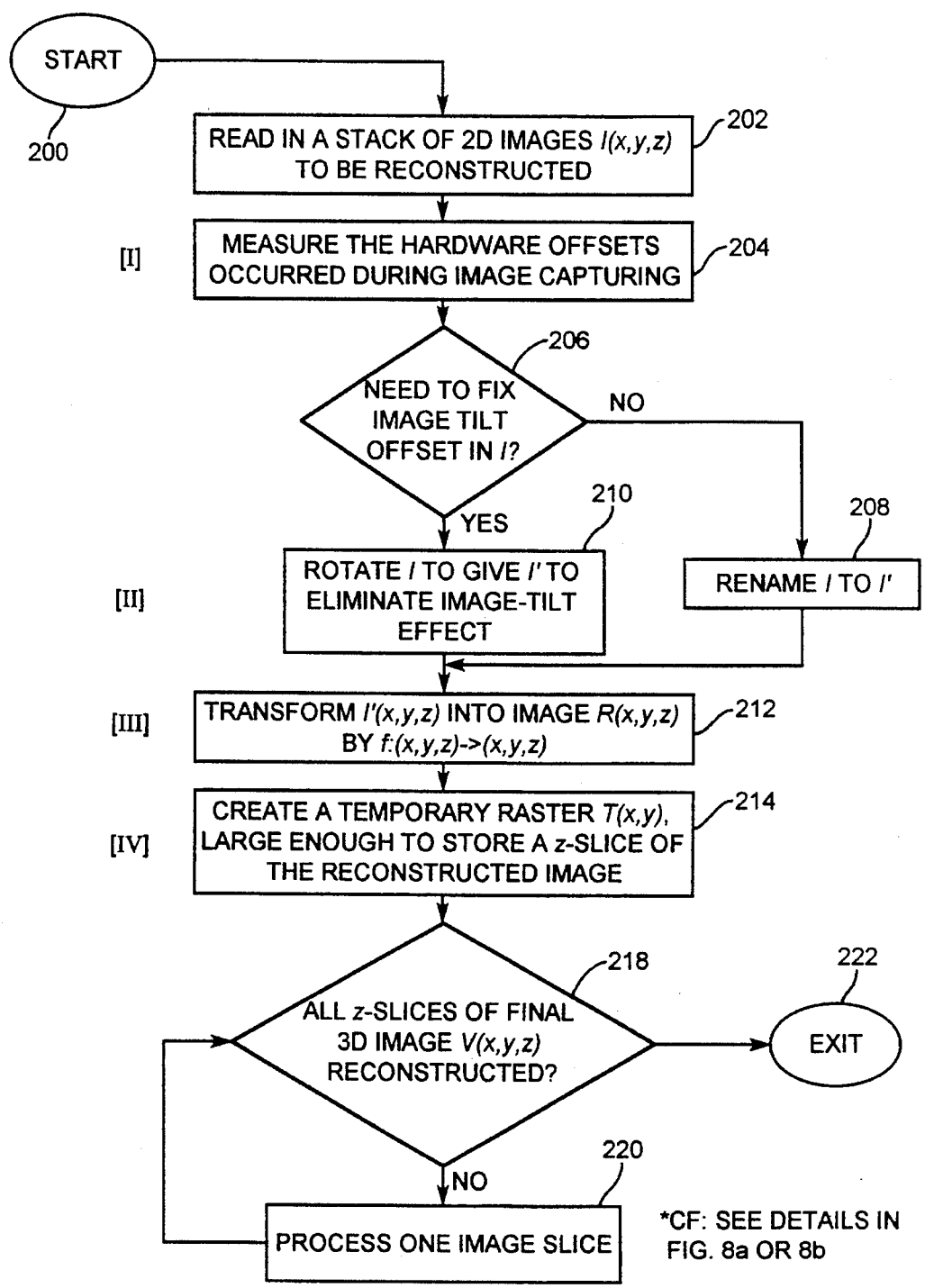
FIG. 7 is a flowchart showing the steps performed by the volume reconstruction module to create a volumetric digital data array representing a three-dimensional ultrasound image.

With reference now to FIGS. 6a and 6b, when it is desired to operate the three-dimensional ultrasound imaging system 20 to acquire two-dimensional images of the target volume, the system 20 must be initialized. This requires the ultrasound probe 24 to be positioned in the probe actuating assembly 22 (see block 100). Once this is done, the ultrasound probe 24 and probe actuating assembly 22 must be properly located with respect to the subject so that the ultrasound waves transmitted by the ultrasound probe 24 are directed at the target volume (see block 102).

Once the ultrasound probe 24 is positioned, a user inputs a start command by selecting an appropriate icon displayed on the screen 36a using the graphical input device 38. Within the context of the present invention, icon refers to any graphical element displayed on the screen 36a which can be selected using graphical input device 38. When the start command is received by the user interface module 84, the user interface module signals the probe scanning module 98. The probe scanning module 98 in turn conveys signals to controller 40 which in turn signals the ultrasound probe 24 to transmit ultrasound signals. The reflected ultrasound signals received from the target volume are conveyed to the clinical ultrasound machine 28 wherein a two-dimensional analog image of the target volume upon which the ultrasound signals impinged, is created. The two-dimensional analog image is then conveyed to the computer 32 via communication line 34 wherein it is captured and digitized via frame grabber module 80. The digitized two-dimensional image is then stored in the memory 82.

A copy of the digitized two-dimensional image is then conveyed to the user interface module 84 and the frame is drawn on the screen 36a of the monitor 36 (block 104). The user then manually rotates the probe 24 while it is transmitting ultrasound signals so that two-dimensional analog images generated by the clinical ultrasound machine 28 are captured and digitized by the frame grabber module 80. These two-dimensional images are also then drawn on the screen 36a of monitor 36 via user interface module 84 (block 106). Next, the user is prompted to confirm that the ultrasound signals are properly directed at the target volume after having viewed the frames drawn on the screen 36a of the monitor (block 108). If the target volume is outside of the drawn frames, then operation returns to block 104. Otherwise, the user provides input to the user interface module 84 using the graphical input device 38 to signify that the target volume is within the drawn frames. Once this has been done, while the user is holding the probe actuating assembly 22 in place (block 110), the user interface module 84 signals the probe scanning module 98.

At this point in time, the probe scanning module 98 conveys control signals to the probe actuating assembly 22 via controller 40 so that the ultrasound probe 24 is rotated while it is transmitting ultrasound signals and receiving reflected ultrasound signals so that the entire target volume is scanned. As the ultrasound probe receives reflected ultrasound signals, it conveys analog information to the clinical ultrasound machine 28 which in turn generates two-dimensional analog images. In this manner, a succession of two-dimensional analog images of the target volume representing a volume image are generated by the clinical ultrasound machine 28 in response to the output of the ultrasound probe 24 (block 112). The succession of two-dimensional analog images generated by the clinical ultrasound machine 28 are captured and digitized by the frame grabber module 80. The digitized two-dimensional images are then conveyed to memory 82 and stored as a stack to form an array of two-dimensional images I(x,y,z) with the pixels in the array I(x,y,z) representing pixels of the digitized two-dimensional images. Because the computer 32 controls the position of the probe actuating assembly 22 and hence the ultrasound probe 24, the spatial orientation of the individual two-dimensional images relative to the target volume is known.

In the present embodiment, the two-dimensional images are considered to be grayscale images. However, the present invention does not depend on the "color" of the two-dimensional images to function properly. A grayscale pixel is associated with a gray-level having a value between 0 and $(2^n -1)$ inclusively, with n being the number of bits required for storing the gray-levels. The gray-level 0 is usually used as a "background color" and is said to be Black.

Once the two-dimensional images have been acquired and saved in memory 82 to form array I(x,y,z), the user interface module 84 generates a prompt to signify that this stage of the image capturing has been completed. At this time, the user may review the acquired frames individually in the manner described previously (block 114). If the two-dimensional images have been acquired incorrectly (block 116), the user can condition the system 20 to return to block 102. Otherwise, the acquired two-dimensional images are saved in the external file storage memory 88 (block 118).

Once the two-dimensional digitized images of the target volume have been acquired, the user is prompted to decide whether a three-dimensional image of the target volume is to be reconstructed from the array of two-dimensional digital images I(x,y,z) via volume reconstruction module 90 (block 120). If the user wishes to reconstruct a three-dimensional image, a volumetric image array V(x,y,z) representing a three-dimensional image of the target volume is created from the two-dimensional digital images (block 122). Once created, the volumetric digital image array is saved in external file storage memory 88 (block 124). Afterwards, the user is prompted to decide whether the three-dimensional image is to be displayed on the screen 36a of the monitor 36 (block 126). If the user wishes to view the three-dimensional image, then a copy of the volumetric image array V(x,y,z) is retrieved from the external file storage memory 88 by the display module 92 and is displayed on the screen 36a (block 128). The displayed image can be manipulated by the user as will be described. During image manipulation, the user can store displayed views in the memory 82 or in the external file storage memory 88 so that these views can be retrieved and re-examined at a later time. Once image manipulation has been completed, the user is prompted to confirm whether another three-dimensional image is to be created (block 130). If the user wishes to create another three-dimensional image, the system 20 reverts to block 102. Otherwise, the three-dimensional imaging procedure is considered to be completed.

If at block 120, the user does not wish to reconstruct a three-dimensional image, or if at block 126, the user does not elect to view the reconstructed three-dimensional image, the system proceeds directly to block 130.

Three-Dimensional Image Reconstruction

Turning now to FIGS. 7 to 18, the steps performed by the volume reconstruction module 90 to generate the volumetric image array V(x,y,z) from the digitized two-dimensional images are better illustrated.

If at block 120, the user elects to reconstruct a three-dimensional image by selecting the appropriate icon using the graphical input device 38, the volume reconstruction module 90 is initialized by the user interface module 84 (block 200). Once initialized, the volume reconstruction module 90 retrieves a copy of the array of digitized two-dimensional images I(x,y,z). The digitized images are then manually examined to determine whether any hardware offsets occurred during capturing of the two-dimensional images (block 204).

In the system 20, three types of hardware offsets may occur during capturing of the two-dimensional images. These hardware offsets are image-tilt offsets, displacement offsets and tilting offsets. An image-tilt offset results in a captured two-dimensional image being rotated through an angle of rotation. This offset occurs when the actual scanning axis ASA of the ultrasound probe 24 is at an angle B to the theoretical scanning axis TSA of the ultrasound probe (see FIG. 10a).

Displacement offset occurs when the two-dimensional images are captured "off-center" from the theoretical scanning axis TSA. In other words, this type of offset occurs when the actual scanning axis ASA of the ultrasound probe 24 is parallel to, but displaced from the theoretical scanning axis TSA (see FIG. 10b).

Figure 10A:
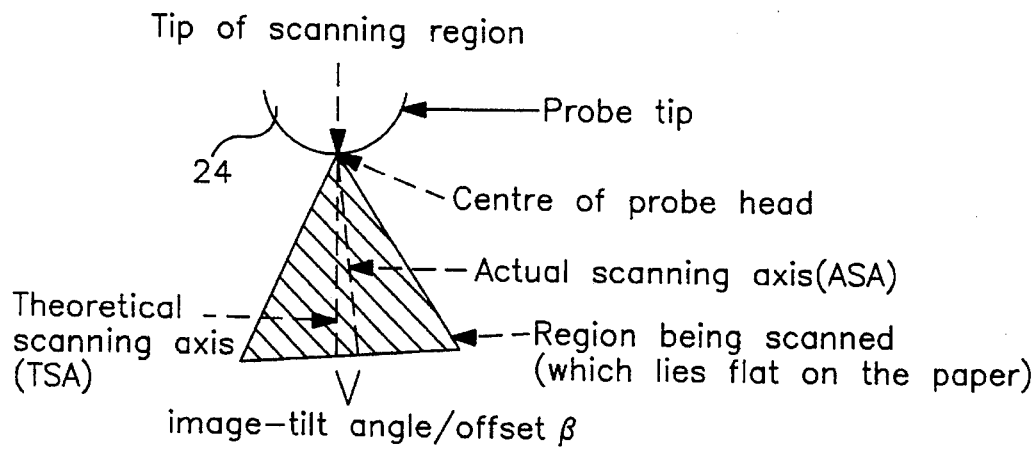
FIGS. 10a, 10b and 10c illustrate hardware offsets which may occur when a succession of two-dimensional ultrasound images is being captured by the system.
Figure 10B:
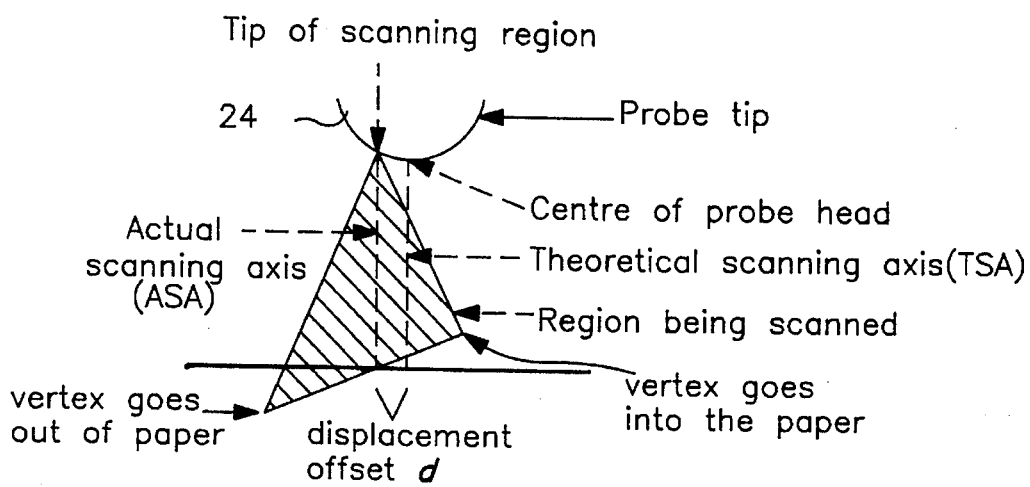
Figure 10C:
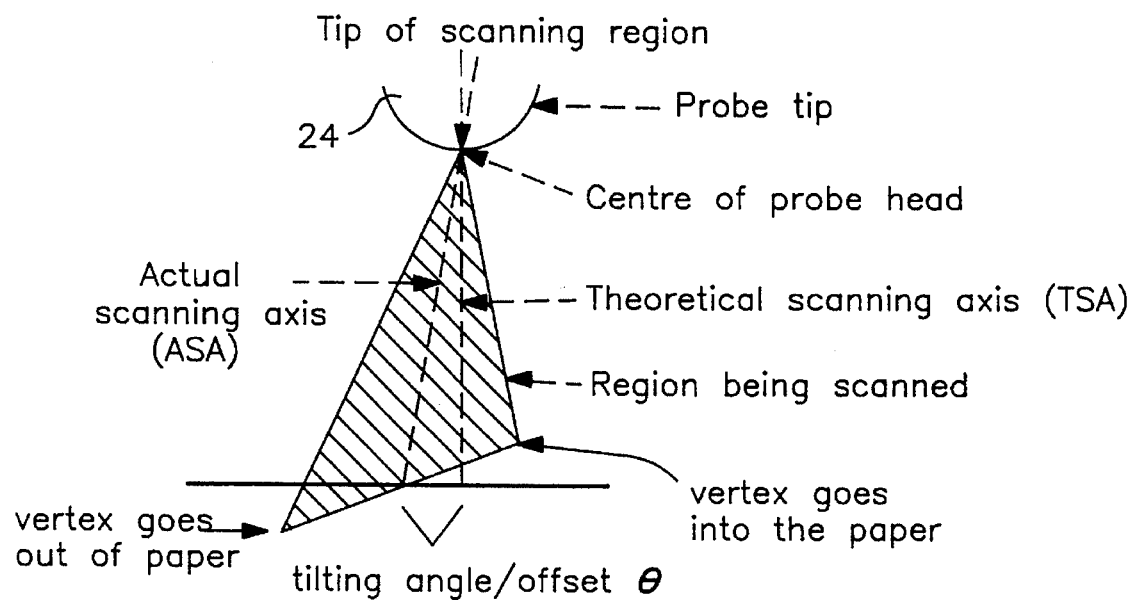

Tilting offset occurs when the two-dimensional images are captured at an angle to the theoretical scanning axis TSA of the ultrasound probe 24 (see FIG. 10c).

It is desirable to compensate for these offsets so that inaccuracies in the final reconstructed three-dimensional image do not occur. In particular, if the image-tilt offset is not removed, wrong image pixels might be used to reconstruct image slices of the target volume. If the displacement and tilting offsets are not removed, distortions in the reconstructed three-dimensional image may occur.

Once the array of digitized two-dimensional images I(x,y,z) has been manually examined and any hardware offsets measured, the volume reconstruction module 90 proceeds to block 206. If the array of two-dimensional images is not affected by image-tilt offset, the array of two-dimensional images is renamed from I(x,y,z) to I'(x,y,z) (block 208). However, if the array of two-dimensional images I(x,y,z) is affected by image-tilt offset, the array of two-dimensional images is rotated to remove the image-tilt offset and the rotated array of two-dimensional images is renamed to I'(x,y,z) (block 210).

Figure 11A:
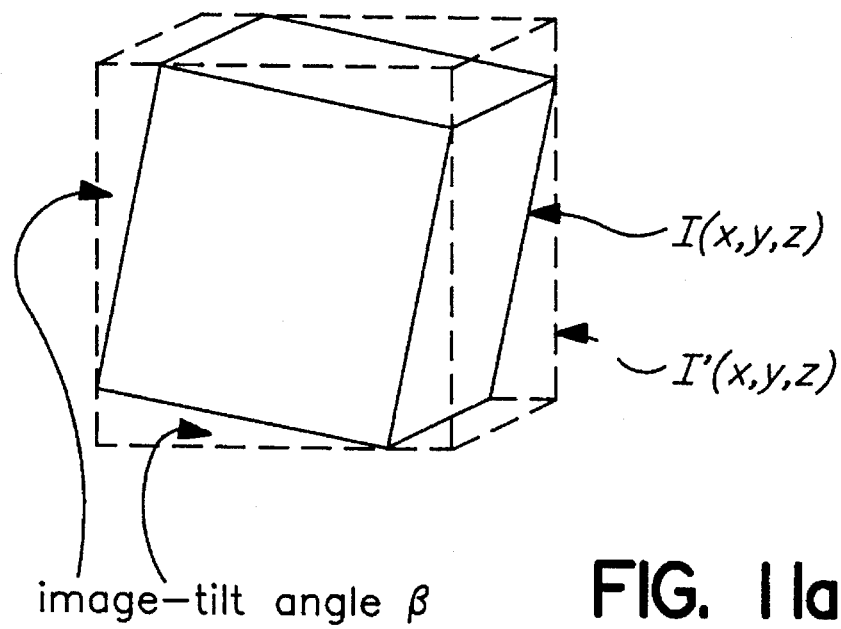
Figure 11B:
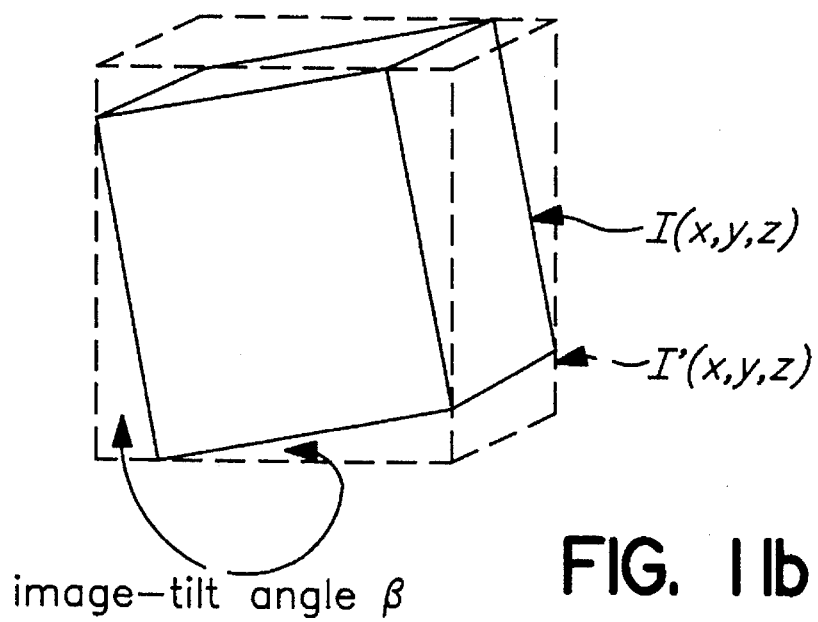

FIGS. 11*a* and 11*b* show the array of two-dimensional images I(x,y,z) being rotated to remove image-tilt offset. The rotation of the array of two-dimensional images I(x,y,z) is achieved through a standard image rotation procedure. Each two-dimensional image in the array of two-dimensional images I(x,y,z) is rotated in the opposite direction as the image-tilt by an angle B. Regions of the array of two-dimensional images I'(x,y,z) which are not available from the array of two-dimensional images I(x,y,z) are set to Black.

After the array of two-dimensional images has been renamed or adjusted to compensate for image-tilt offset, the array of two-dimensional images I'(x,y,z) is transformed into a resultant image array R(x,y,z). The transformation function used to transform array I'(x,y,z) into image array R(x,y,z) is f: (x,y,z) ->(x,z,y) with the assumption that the ultrasound probe 24 was positioned above or below the target volume when the images were taken (block 212). The transformation of array I'(x,y,z) to image array R(x,y,z) is performed on a pixel-by-pixel basis using known methodologies.

Figure 12:
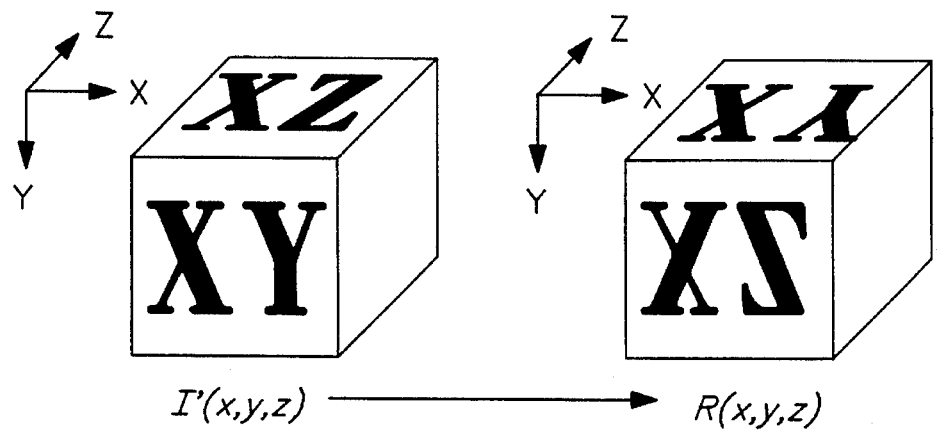
FIG. 12 is a reconstruction diagram showing transformation of an image captured by axial rotation.

FIG. 12 shows the effect of transforming the array of two-dimensional images I'(x,y,z) to image array R(x,y,z). This transformation is performed when the ultrasound probe 24 was either above or below the target volume when the images in array I'(x,y,z) were taken. The transformation is done by mapping the xz-planes of array I'(x,y,z), for all y, into the xy-planes of image array R(x,y,z). As can be seen, the top xz-plane of array I'(x,0,z) becomes the front xy-plane of image array R(x,z,0).

After the transformation has been performed, each xy-slice of image array R(x,y,z) will contain a set of cross-sections (or image lines) of the two-dimensional images in array I'(x,y,z). These two-dimensional image lines are used for reconstructing the same image slice.

When the ultrasound probe 24 is positioned to the left or right of the target volume when the images in array I'(x,y,z) are taken, the transformation is performed by mapping the xz-planes of array I'(x,y,z), for all y, into image array R(Y-y,z,x), where Y is the y-dimension of the images in array I'(x,y,z). As above, after the transformation, each xy-slice of image array R(x,y,z) will contain a set of cross-sections of two-dimensional images in array I'(x,y,z) to be used for reconstructing the same image slice.

Figure 13:
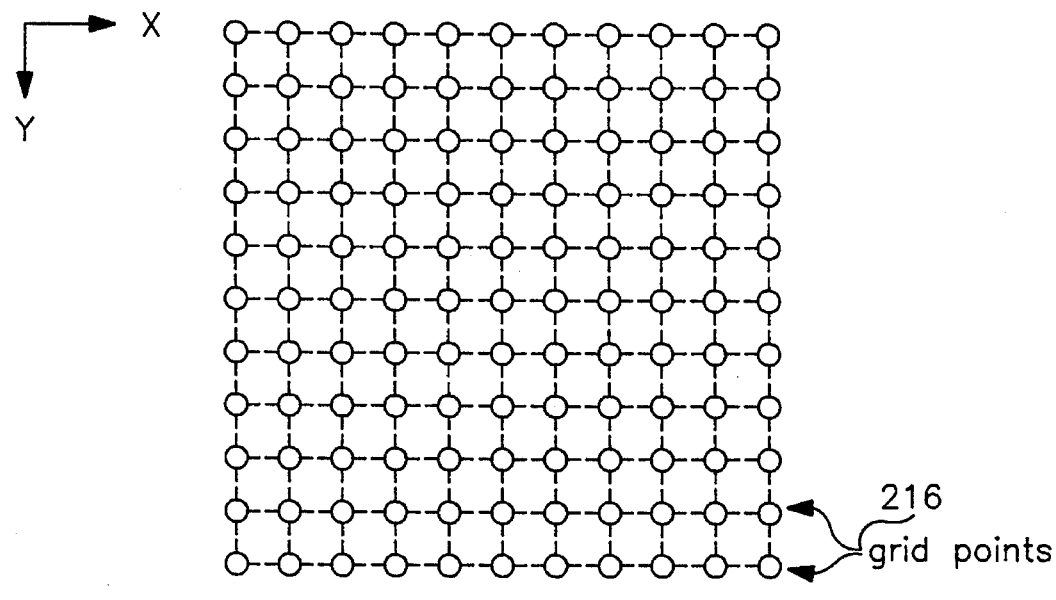
FIG. 13 is a reconstruction diagram schematically representing a temporary raster.
Figure 14:
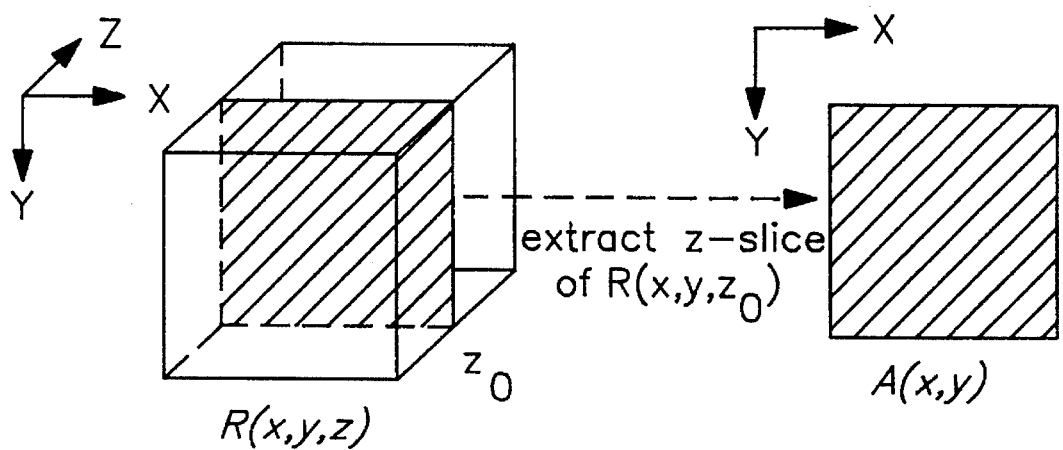
FIG. 14 is a reconstruction diagram showing an extraction of a slice of a three-dimensional ultrasound image.

Once the images in image array R(x,y,z) have been generated, a temporary raster T(x,y) is created which is large enough to store a z-slice of the reconstructed three-dimensional image (block 214). FIG. 13 shows a temporary raster T(x,y) comprising a plurality of grid points or pixels 216. Each element of raster T(x,y) is an image pixel lying at an intersection of two lines. The first pixel (or "origin") of raster T(0,0) is at the top-left-corner of the raster, and indexes of raster T(x,y) run from left to right, and then top to bottom.

Once the temporary raster T(x,y) has been created, a z-slice A(x,y) of the image array R(x,y,z) is processed and the reconstructed image of that z-slice is stored in raster T(x,y). The volume reconstruction module 90 then checks to see if all of the z-slices A(x,y) of the image array R(x,y,z) have been reconstructed (block 218). If not, another z-slice of image array R(x,y,z) is fetched and that z-slice A(x,y) is processed at block 220. The volume reconstruction module 90 then reverts back to block 218. This loop continues until all of the z-slices A(x,y) of image array R(x,y,z) have been reconstructed. At this stage, the volumetric image array V(x,y,z) representing the three-dimensional image is complete and the volume reconstruction module 90 is exited (block 222).

Figure 8A:
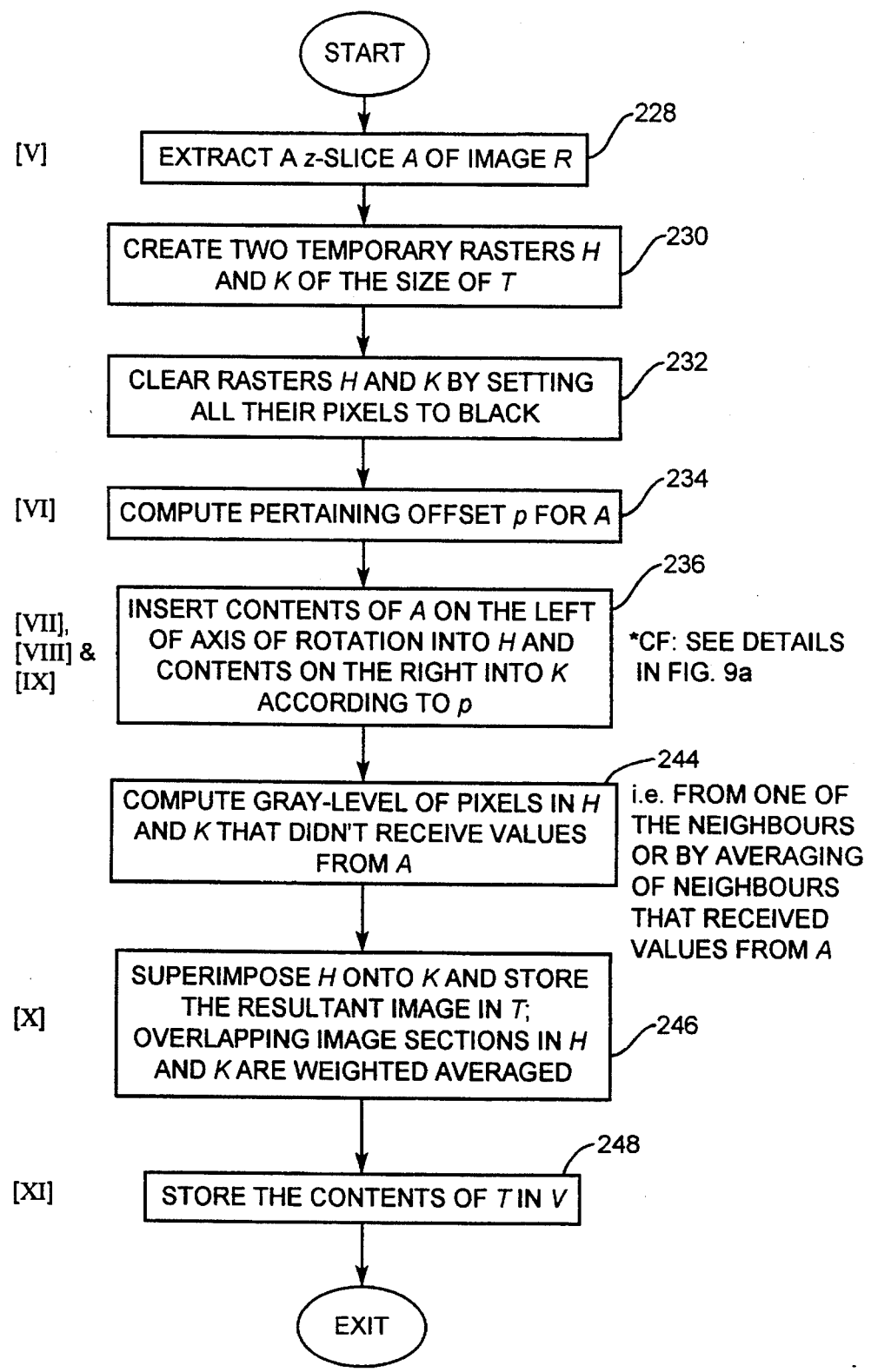
FIGS. 8a and 8b are flowcharts showing the details of one of the steps illustrated in FIG. 7.

FIG. 8*a* better illustrates the steps performed by the volume reconstruction module 90 to process one z-slice A(x,y) at block 220. In particular, after a z-slice A(x,y) of image array R(x,y,z) has been fetched (block 228), two additional temporary rasters H(x,y) and K(x,y), both of the same size as raster T(x,y), are created (block 230). The pixels of the two temporary rasters H(x,y) and K(x,y) are then set to Black (block 232).

After block 232 has been completed, any displacement and/or tilting offset, collectively called the pertaining offset p, is manually measured (block 234). FIG. 15 shows the geometry for calculating the pertaining offset p resulting from displacement and/or tilting offsets assuming that any image-tilt offset has been properly compensated for at block 210. The pertaining offset p for a set of image lines is the distance by which each image line is spaced from the axis of rotation AOR of the ultrasound probe 24. It is the sum of both the displacement offset and the tilting offset. In FIG. 15, a captured image is shown having a displacement offset d and a tiling offset $\Theta$. The displacement offset is always constant for any set of image lines of image array R(x,y,z) to be reconstructed. It is the distance the actual scanning axis ASA is "displaced" from the axis of rotation AOR of the ultrasound probe 24.

For the tilting offset, the effect becomes bigger as the distance between the reconstruction image plane (on which the image lines resides) and the tip of the scanning region of the ultrasound probe 24 increases. Thus, the actual tilting offset for a set of image lines is the distance between the theoretical and actual scanning axes TSA and ASA respectively and it is denoted by $\epsilon$, where $\epsilon$ is given by the product of D and $SIN(\Theta)$. D is the distance from the image lines to the tip of the scanning region. Accordingly, the pertaining offset p for a set of image lines is given by $d+\epsilon$.

When the displacement and/or tilting offsets cause the "center" pixel of an image line (i.e., the one closest to the axis of rotation AOR of the ultrasound probe) to be placed on the same side as the path of the rotation of the ultrasound probe 24, the value of the pertaining offset p is positive. When the offset causes the "center" pixel to be placed on the opposite side of the path of rotation of the ultrasound probe 24, the value of the pertaining offset p is negative.

Once the pertaining offset p has been determined, the z-slice A(x,y) is broken down into two parts according to the pertaining offset p, one part of which represents pixels of z-slice A(x,y) located to the right of the axis of rotation AOR of ultrasound probe 24 and another part of which represents pixels of z-slice A(x,y) located to the left of the axis of rotation AOR of the ultrasound probe. The pixels of the one part are reconstructed and are stored in raster H(x,y) while the pixels of the other part are reconstructed and are stored in raster K(x,y) (block 236).

Figure 9A:
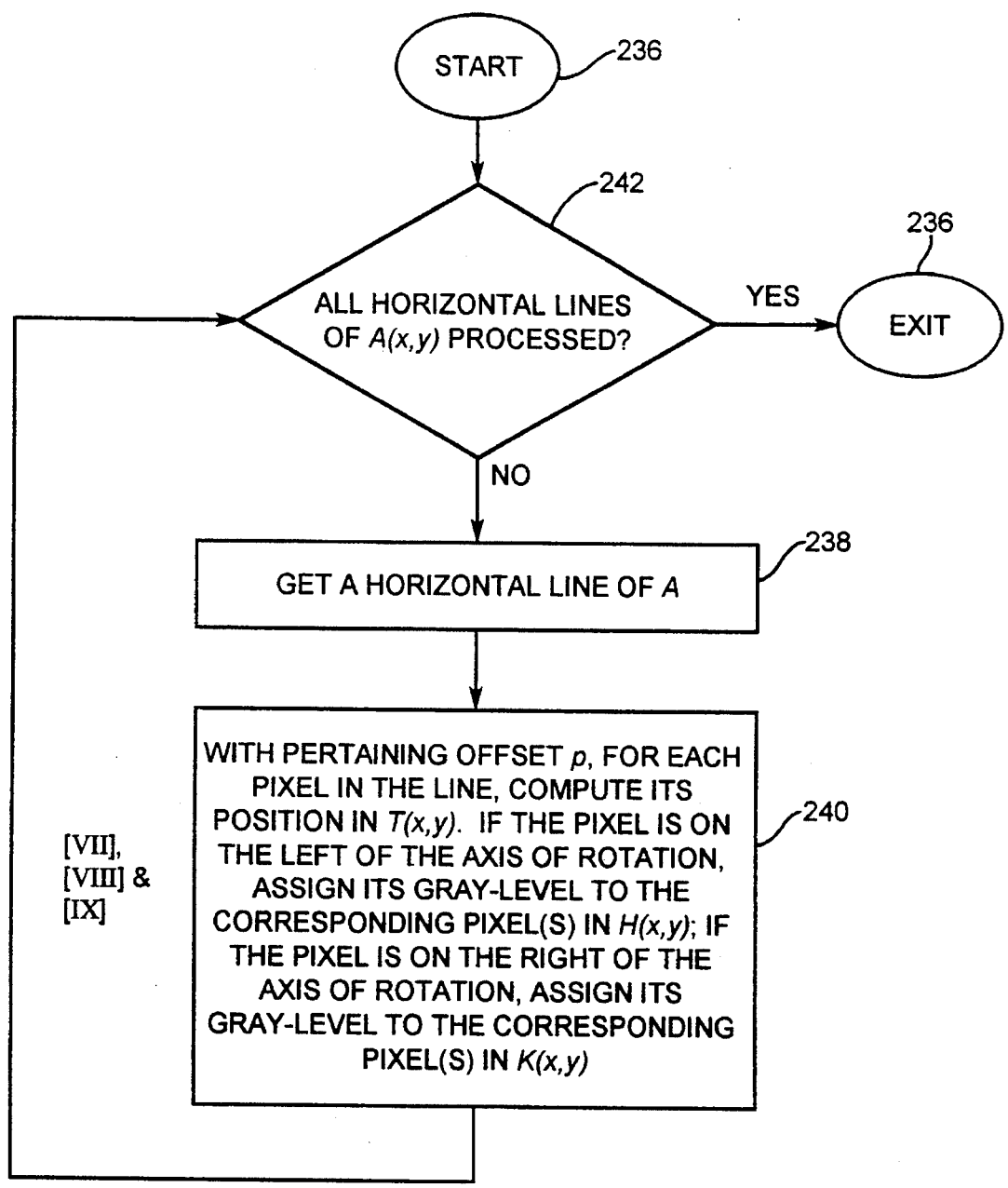
FIGS. 9a and 9b are flowcharts showing the details of one of the steps illustrated in FIGS. 8a and 8b.

FIG. 9a better illustrated the steps performed by the volume reconstruction module 90 to complete block 236. Specifically at block 236, a horizontal line of z-slice A(x,y) is acquired (block 238). With the pertaining offset p calculated, the location of each pixel of z-slice A(x,y) in raster T(x,y) is computed. If a pixel is to the left of the axis of rotation AOR of the ultrasound probe 24, the gray-level of the pixel is assigned to the corresponding pixel in raster H(x,y). If a pixel is to the right of the axis of rotation AOR of the ultrasound probe 24, the gray-level of the pixel is assigned to the corresponding pixel in raster K(x,y) (block 240).

After this, the volume reconstruction module 90 determines whether all of the horizontal lines of z-slice A(x,y) have been processed (block 242). If not, the next horizontal line of z-slice A(x,y) is acquired at block 238 and step 240 is repeated. This loop continues until all of the horizontal lines of the z-slice A(x,y) have been processed and the pixels therein assigned to pixels in one of rasters H(x,y) and K(x,y) respectively.

Figure 16A:
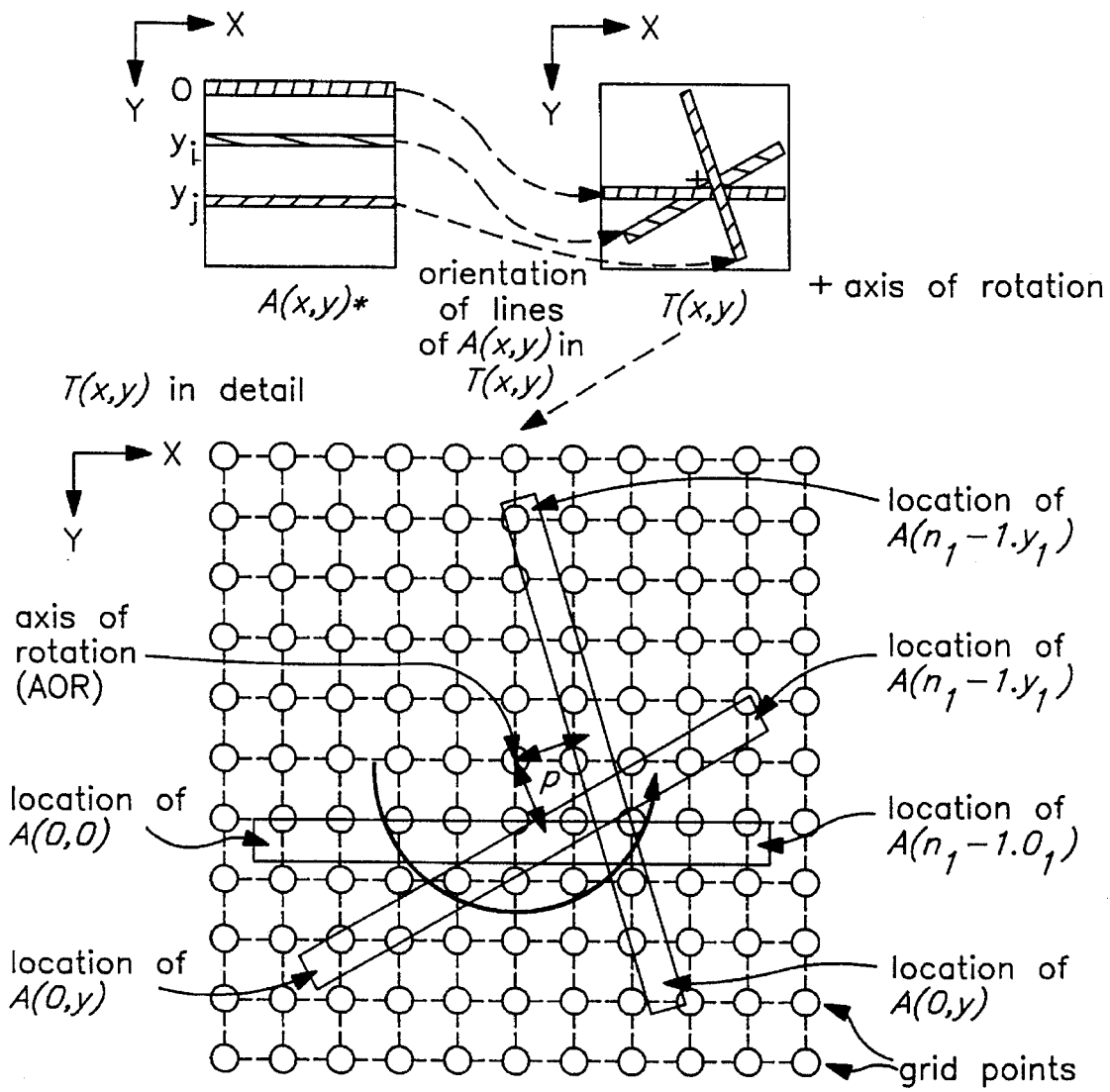
FIGS. 16a to 16c are reconstruction diagrams showing the computation of the contents of the temporary rasters for image data captured by axial rotation with the hardware offsets illustrated in FIGS. 10b and 10c properly compensated.

FIG. 16a shows the orientation of image lines of z-slice A(x,y) in temporary raster T(x,y) with a positive pertaining offset p. Also shown is the geometry for capturing two-dimensional images for the axial rotation reconstruction, as well as for placing the image lines in z-slice A(x,y) back into raster T(x,y) for reconstruction.

Since the two-dimensional images are captured counter-clockwise, the image lines are placed back into raster T(x,y) in a counterclockwise fashion. As a reference model, the first image line is always placed horizontally at the axis of rotation AOR of the ultrasound probe 24. To compensate for displacement and/or tilting offsets, the image line is translated from the axis of rotation AOR by the distance given by the pertaining offset p. If the pertaining offset p is positive, the image line is shifted down from the axis of rotation and if the pertaining offset p is negative, the image line is shifted up from the axis of rotation. Similarly, a subsequent image line is placed and translated by the distance given by the pertaining offset p according to the orientation of the subsequent image line in raster T(x,y). Thus, in effect, the image lines form a circle of radius p at the axis of rotation (see FIG. 18b).

Figure 16B:
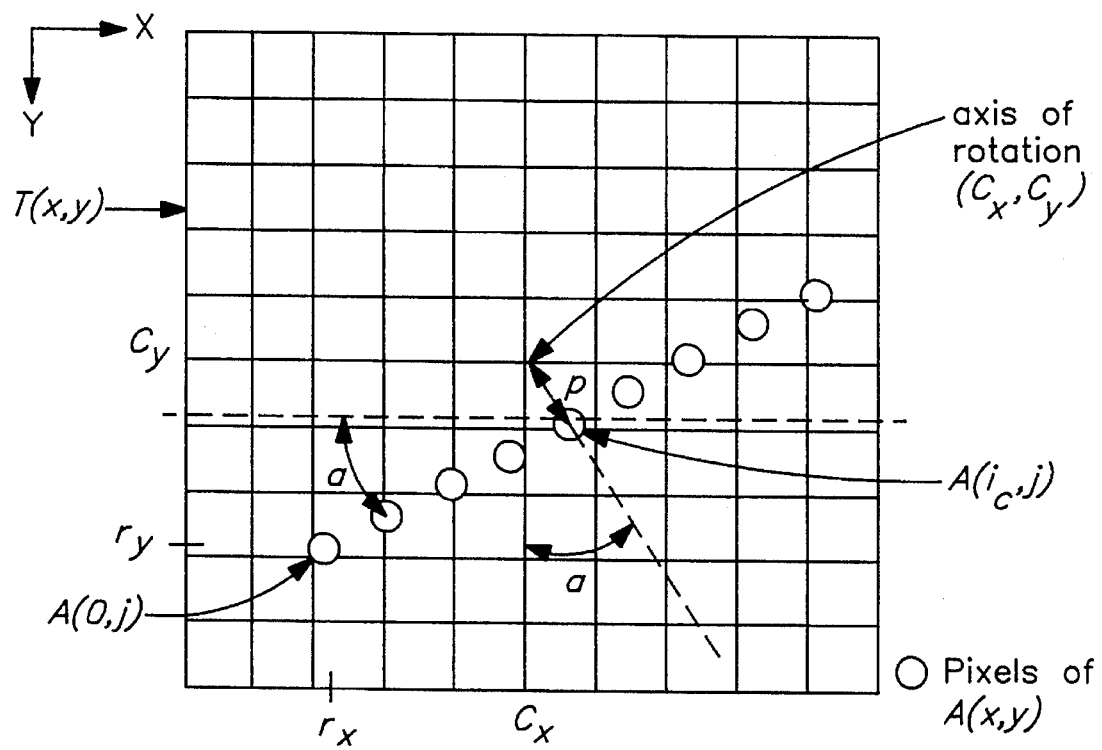
Figure 16C:
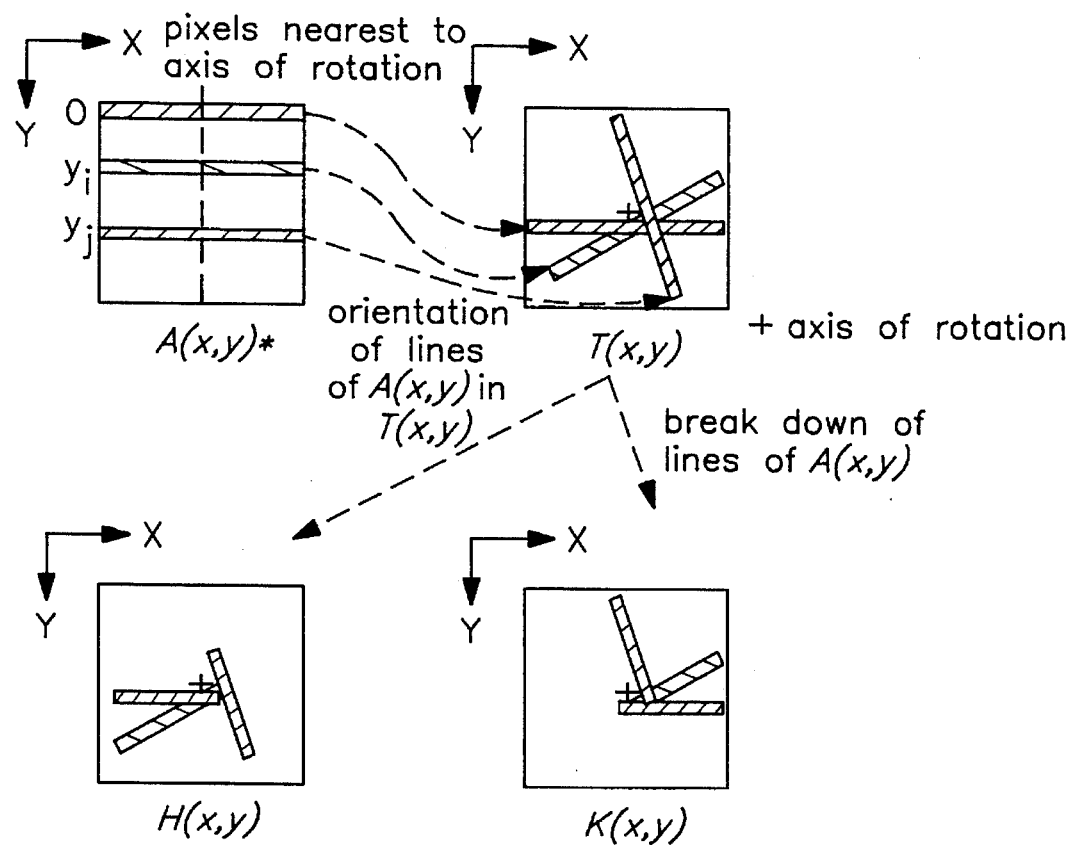

FIG. 16b shows the geometry for calculating locations of pixels of a line of A(x,y) in raster T(x,y) according to the pertaining offset p. For each image line in A(x,y), the location of its first pixel A(0,y) in raster T(x,y) is calculated as if the pertaining offset p is zero. The location is then offset by the pertaining offset p according to the orientation of the image line in T(x,y). The first pixel is then inserted into raster T(x,y) by assigning its gray-level to the corresponding pixel(s) in raster T(x,y). For a subsequent pixel in the image line, its location in raster T(x,y) is acquired by a constant offset from the location of the previous pixel in the image line.

In FIG. 16b, the axis of rotation in raster T(x,y) is $(C_x, C_y)$ and in z-slice A(x,y), the axis of rotation is $(i_c, j)$. The angle of orientation (which is also the angle of rotation) of the image line is a. If the pertaining offset p is zero, the location of A(0,y) would be at $((C_x - i_c * COS(a)), (C_y + i_c * SIN(a)))$. Then the location is shifted by the pertaining offset p according to a; that is $((p * SIN(a)), (p * COS(a)))$. Therefore the actual location of A(0,y) is at $((C_x - i_c * COS(a) + p * SIN(a)), (C_y + i_c * SIN(a) + p * COS(a)))$.

The location of a subsequent pixel is acquired by offsetting the location of the previous pixel by the constant $(COS(a), -SIN(a))$.

Although the above describes placing the image lines of z-slice A(x,y) directly into raster T(x,y), it should be apparent to one of skill in the art that the same technique is used to place the image lines of z-slice A(x,y) into rasters H(x,y) and K(x,y) respectively, with the exception that image lines having pixels to the left and right of the axis of rotation AOR of the ultrasound probe 24 are separated into two parts and the parts are processed separately.

Once all of the horizontal lines of the z-slice A(x,y) have been processed, the volume construction module 90 computes the gray-level of the pixels in the rasters H(x,y) and K(x,y) that did not receive values from z-slice A(x,y). This is done by propagating the gray-level assigned to one of its neighbouring pixels or by averaging the gray-levels assigned to neighbouring pixels that received gray-levels from z-slice A(x,y) (block 244).

Figure 17:
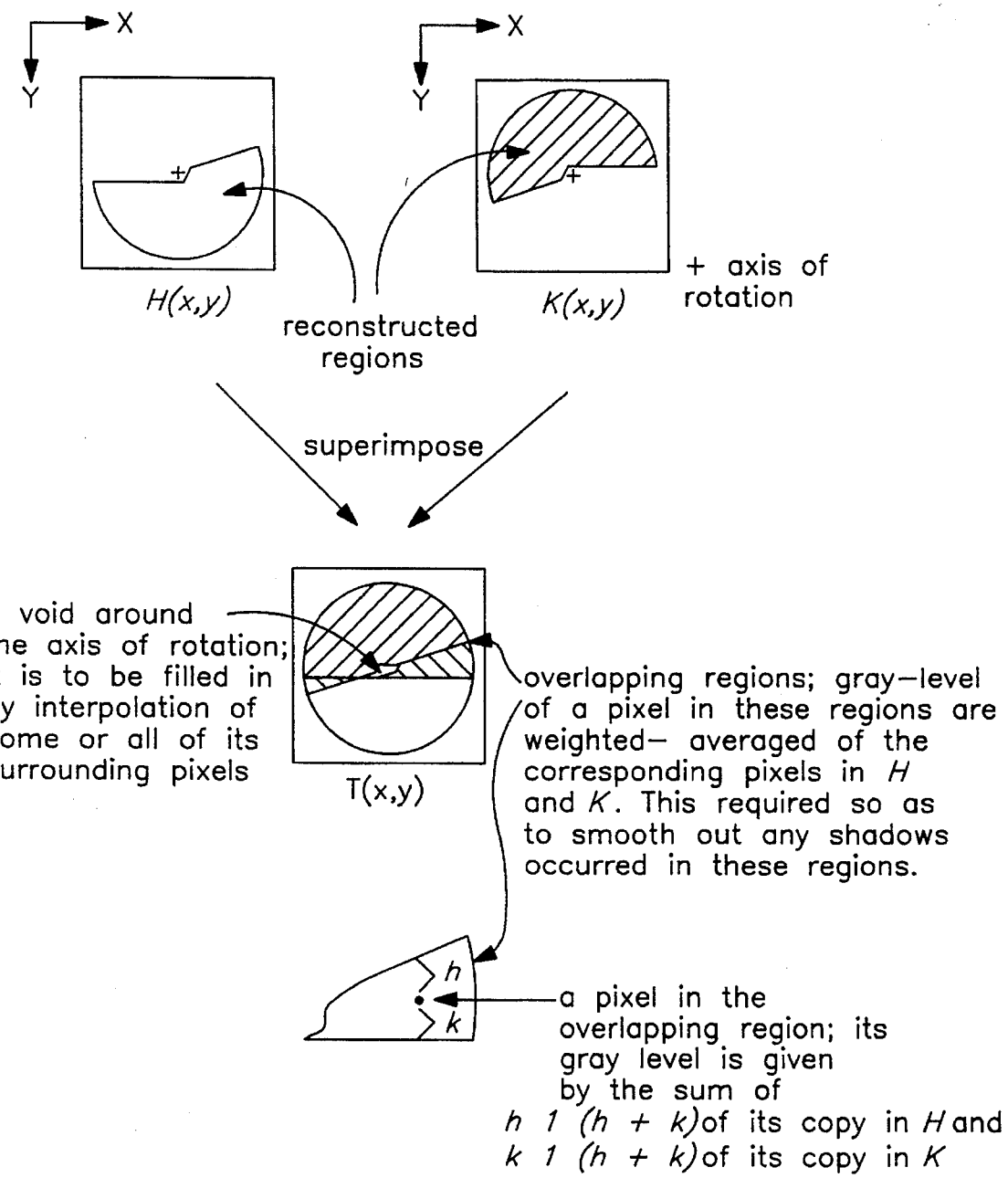
FIG. 17 are reconstruction diagrams showing superimposition of the contents of temporary rasters to form a reconstructed image slice.

After block 244 has been completed, raster H(x,y) is superimposed onto raster K(x,y) and the resultant image is stored in raster T(x,y) (block 246). FIG. 17 shows the manner in which the rasters H(x,y) and K(x,y) are superimposed. Specifically the non-overlapping regions of the rasters H(x,y) and K(x,y) are taken as is, whereas the overlapping regions of the two rasters are weight-averaged. The superimposition of the two rasters is performed to reduce any sudden change of gray-levels in the reconstructed three-dimensional image due to ultrasound shadows in the overlapping regions of rasters H(x,y) and K(x,y).

When an overlapping region occurs, the vertical distances h and k from each pixel to the upper edge and to the lower edge of the overlapping region respectively, are calculated. The gray-level of the pixel is given by the sum of (h/(h+k)) of the gray-level of its copy in raster H(x,y) and (k/(h+k)) of its copy in raster K(x,y). Thus, for example, when a pixel is closer to the upper edge of the overlapping region ie. to raster K(x,y), its copy in raster H(x,y) will be weighted less and the one in raster K(x,y) will be weighted more. Similarly, when a pixel is closer to the lower edge of the overlapping region ie. to raster H(x,y), its copy in raster H(x,y) will be weighted more and the one in raster K(x,y) will be weighted less.

A void may occur around the axis of rotation AOR when the rasters H(x,y) and K(x,y) are superimposed due to displacement and/or tilting effects. If such a void occurs, it is filled in by interpolation of the gray-levels of some or all of the pixels surrounding the void. After the two rasters H(x,y) and K(x,y) have been superimposed and the voids have been filled to complete raster T(x,y), the contents of raster T(x,y) are stored in volumetric image array V(x,y,z) (block 248).

Figure 18A:
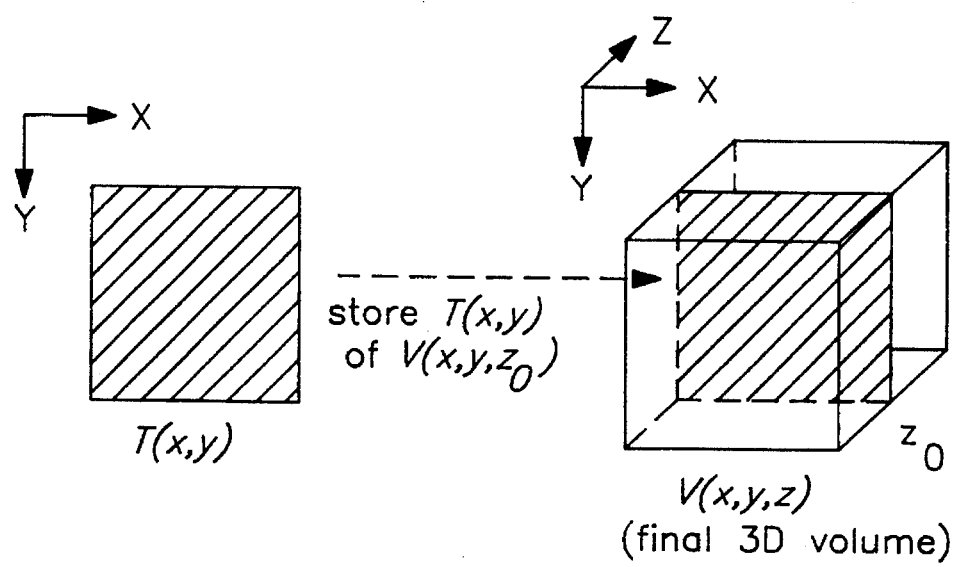
FIG. 18a is a reconstruction diagram showing an image slice forming part of the volumetric digital image array representing the three-dimensional image.

FIG. 18a shows how a reconstructed image slice stored in raster T(x,y) fits into the volumetric image array V(x,y,z) at location $Z=z_0$. The image slice is put back into volumetric image array V(x,y,z) as an xy-slice of the array. Recall that the image slice in raster T(x,y) is reconstructed from pixels in an xy-slice of image array R(x,y,z) extracted from location $Z=z_0$. Therefore, volumetric image array V(x,y,z) will have as many xy-slices as image array R(x,y,z). Thus, its z-dimension will be the same as the height (or width) of a two-dimensional image in array I'(x,y,z) when the ultrasound probe 24 is positioned above or below, or to the left or right respectively, of the target volume when the two-dimensional images in array I'(x,y,z) are taken.

As should be apparent, the volume reconstruction module 90 performs steps 228 to 248 when it reaches block 220 for each z-slice A(x,y) in image array R(x,y,z) until all of the z-slices have been processed. At that time, the volumetric image array V(x,y,z) which represents a three-dimensional image of the target volume is complete and is stored in the external file storage memory 88.

Although the array I'(x,y,z) has been described as undergoing a transformation to generate image array R(x,y,z), it should be realized that proper indexing may be carried out, so that the z-slices A(x,y) can be taken directly from array I'(x,y,z).

Figure 8B:
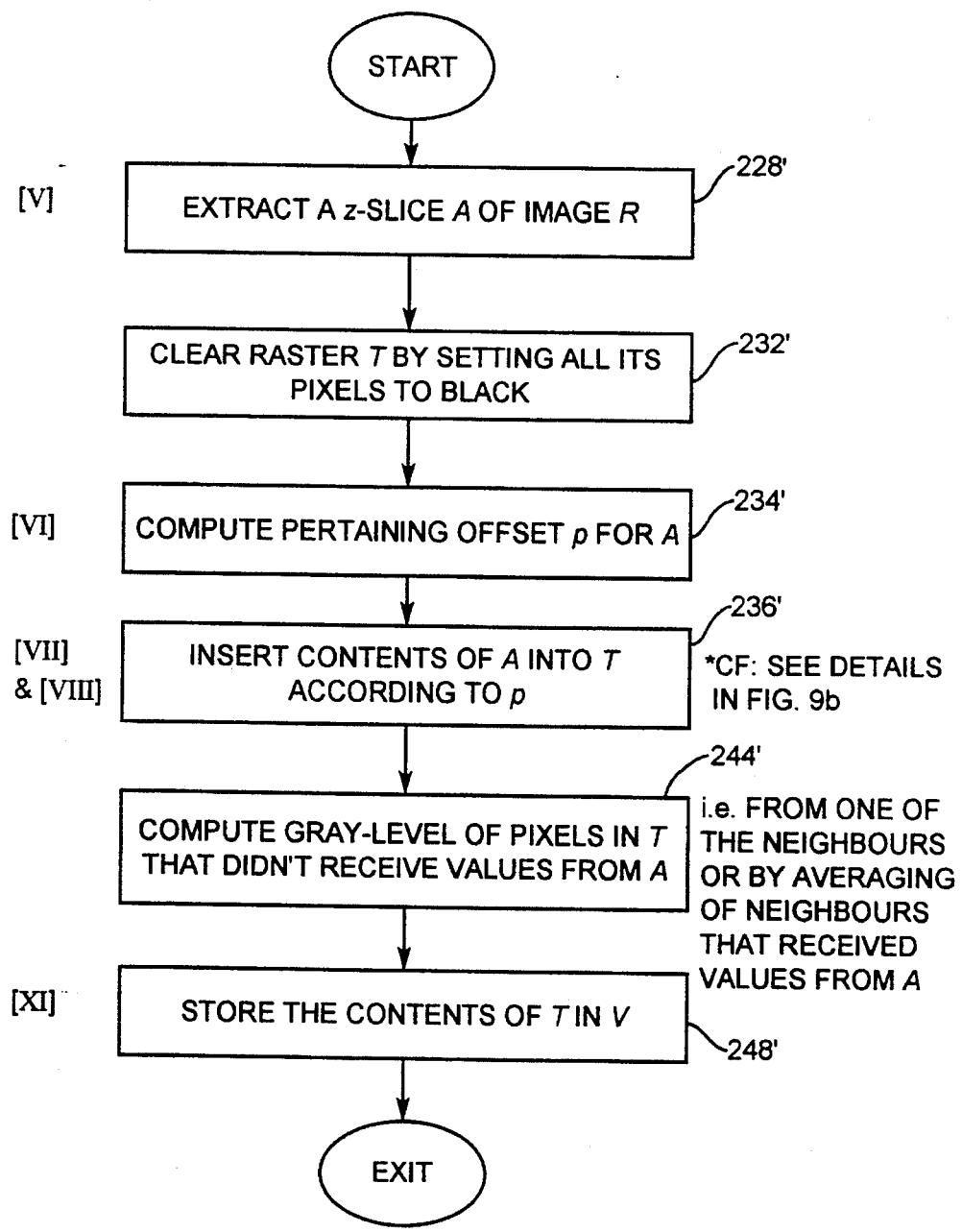

In addition, although during image slice processing at block 220, two rasters H(x,y) and K(x,y) are created and pixels of the image slices are separated and processed separately, these steps need not be carried out. It has been found in the ultrasound imaging art that shadowing effects may occur which affect image quality. The steps carried out at blocks 232 to 246 minimize the effects of shadowing in the reconstructed images. If shadowing is not a concern or if another type of imaging is being carded out which does not suffer from shadowing effects, then the steps performed at block 220 can be modified as shown in FIG. 8b.

Figure 9B:
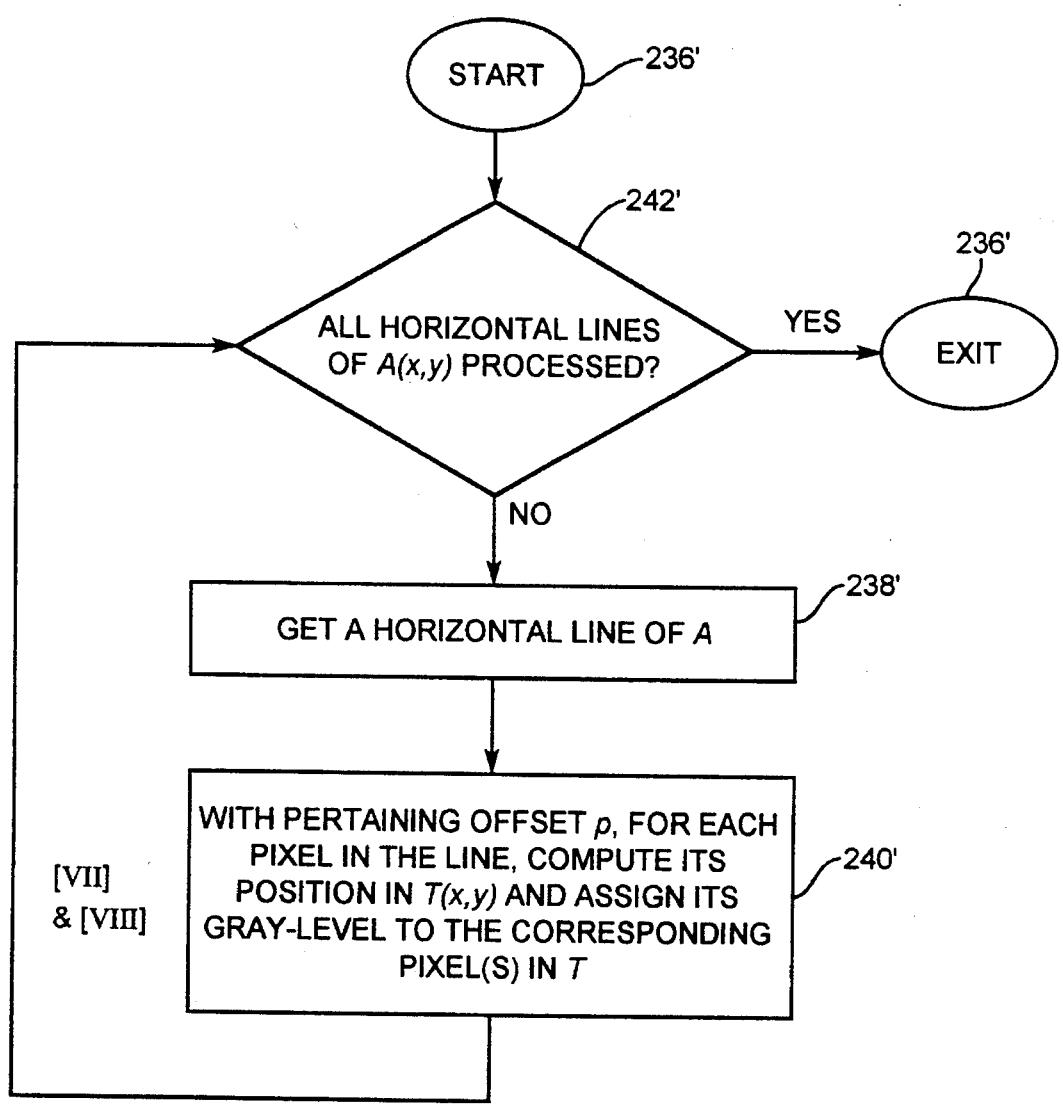

In this instance, a z-slice of image array R(x,y,z) is fetched (block 228') and the pixels in raster T(x,y) are set to Black (block 232'). After this, the pertaining offset p is measured as described previously (block 234'). The z-slice A(x,y) is then inserted into raster T(x,y) according to the pertaining offset p (block 236'). FIG. 9b shows the steps carried out at block 236'. As can be seen, steps 238' to 242' are basically the same as those shown in FIG. 9a except that the pixels in the image lines of z-slice A(x,y) are not separated. Once the z-slice A(x,y) has been inserted into raster T(x,y), the pixels in raster T(x,y) that did not receive gray-levels from z-slice A(x,y) are assigned gray-levels (block 244') by interpolation of the gray-levels of some or all of the neighbouring pixels. The contents in raster T(x,y) are then stored in the volumetric image array V(x,y,z) (block 248').

Although the volume reconstruction technique has been described in an ultrasound three-dimensional imaging system having an axially rotating ultrasound probe, it should be apparent to those of skill in the art that the volume image reconstruction technique may be used in conjunction with three-dimensional imaging systems which use a different type of ultrasound, imaging environment probe and/or sweep geometry to acquire the two-dimensional images. Examples of these ultrasound probes and sweep geometries are fully set out in co-pending U.S. application Ser. No. 08/158,267 filed on Nov. 29, 1993, assigned to the assignee of the present invention, the contents of which are incorporated herein by reference.

If it is necessary for two-dimensional images to be captured from a target volume having a different geometry to that described previously or even along an arbitrary path, the corresponding volumetric image array V(x,y,z) may still be reconstructed using the previously described volume image reconstruction technique as long as a description of the traversing path of the ultrasound probe 24 is known. In this case, the only change that needs to be made is to replace the "axis of rotation" with the "insertion point", the insertion point being a point along the arbitrary path.

FIG. 18b shows raster T(x,y) in which image lines are stored for an axial rotation geometry as well as for an arbitrary path geometry. As can be seen from the arbitrary path geometry, image lines in the raster T(x,y) are perpendicular to the arbitrary path and are translated along the path by the pertaining offset p.

It should also be apparent that the volume image reconstruction technique may be used in different environments other than ultrasound imaging systems where a three-dimensional image needs to be generated for a target volume.

Three-Dimensional Image Display

Once the volume image reconstruction has been completed (block 122) and the reconstructed volumetric image array V(x,y,z) has been stored in the external file storage memory 88 (block 124), the user can decide whether the three-dimensional image is to be displayed on the screen of monitor 36 using the graphical input device 38 (block 126). If the user elects to display the three-dimensional image, the user interface module 84 signals the display module 92 to retrieve a copy of the volumetric image array V(x,y,z) from the memory 88 and display the three-dimensional image on the screen 36a of the monitor 36. Once the image is displayed, the user can manipulate this image as will now be described more fully with reference to FIGS. 19 to 28c.

Figure 19:
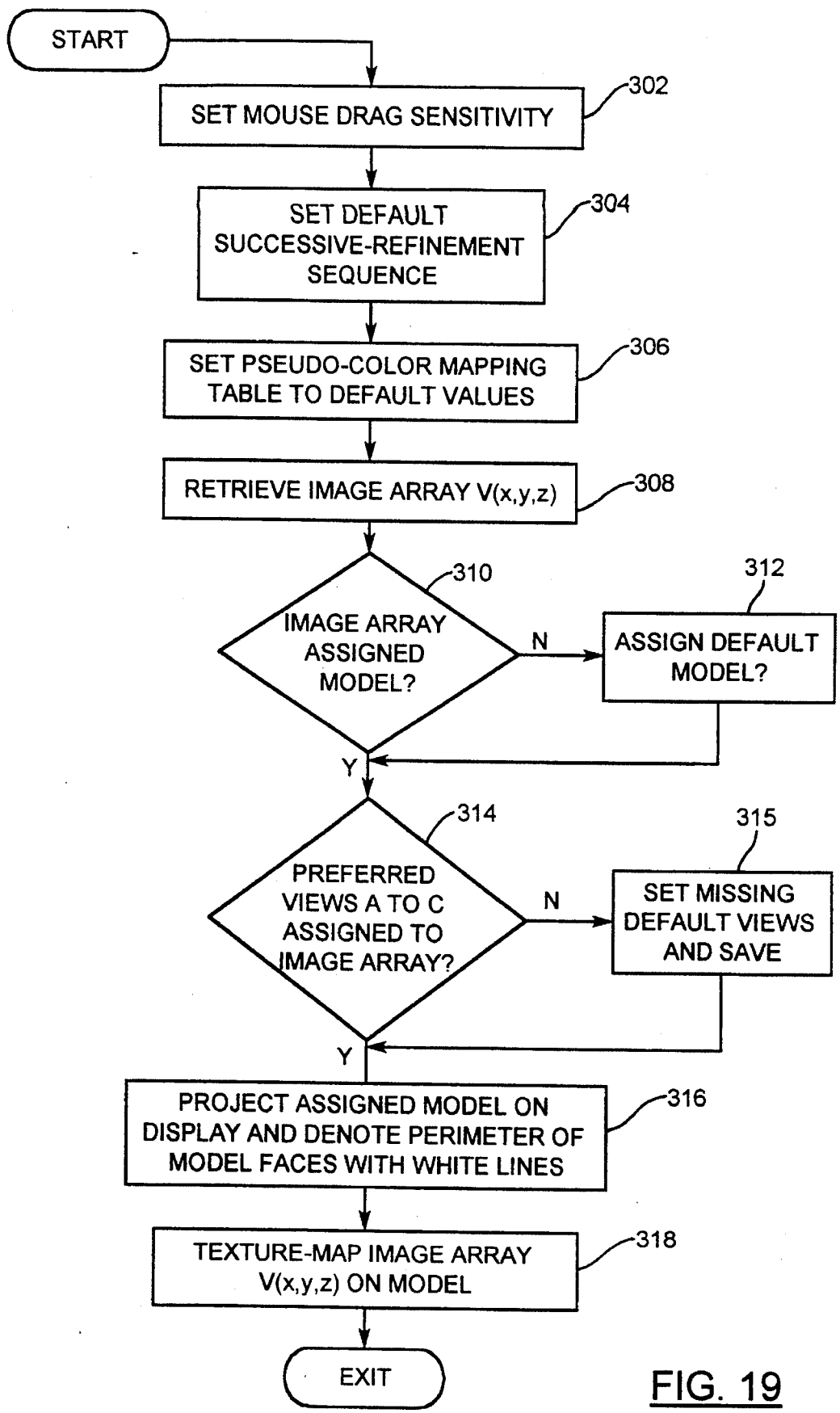
FIG. 19 shows a flowchart of steps performed by the display module during initialization.

When the three-dimensional image is to be displayed as signified by the user via the graphical input device 38, the display module 92 enters an initialization routine (see FIG. 19). Upon entering the initialization routine, the display module 92 sets a number of parameters to their default values as will be explained and uses this information when an image is to be displayed on the screen 36a (blocks 302 to 306). The parameters which are set to their default value are mouse-drag sensitivity, successive refinement sequence and pseudo-color mapping.

After the above has been done, the display module 92 retrieves a copy of the volumetric image array V(x,y,z) from memory 88 and stores it in memory 82 (block 308). Once retrieved, the display module 92 checks to see if the volumetric image array has been assigned a model (block 310). The model is in the form of a convex polyhedron having a plurality of planar faces defined in the same space as the three-dimensional image to be displayed. The polyhedron may take a variety of shapes as will be described herein.

If the image array has not been assigned a model, the dimensions of the volumetric image array V(x,y,z) are examined and a model in the form of a right parallelepiped, which encloses substantially all of the pixels in the image array V(x,y,z), is created and assigned to the image array automatically (block 312). The assigned model is then saved in memory 82 with the copy of the image array. After this, the volumetric image array V(x,y,z) is examined to determine if any or all preferred Views A to C have been assigned to the image array (block 314). If some or all of the preferred Views have not been assigned, the preferred Views are created automatically and saved in the memory 82 with the image array (block 315).

Figure 26:
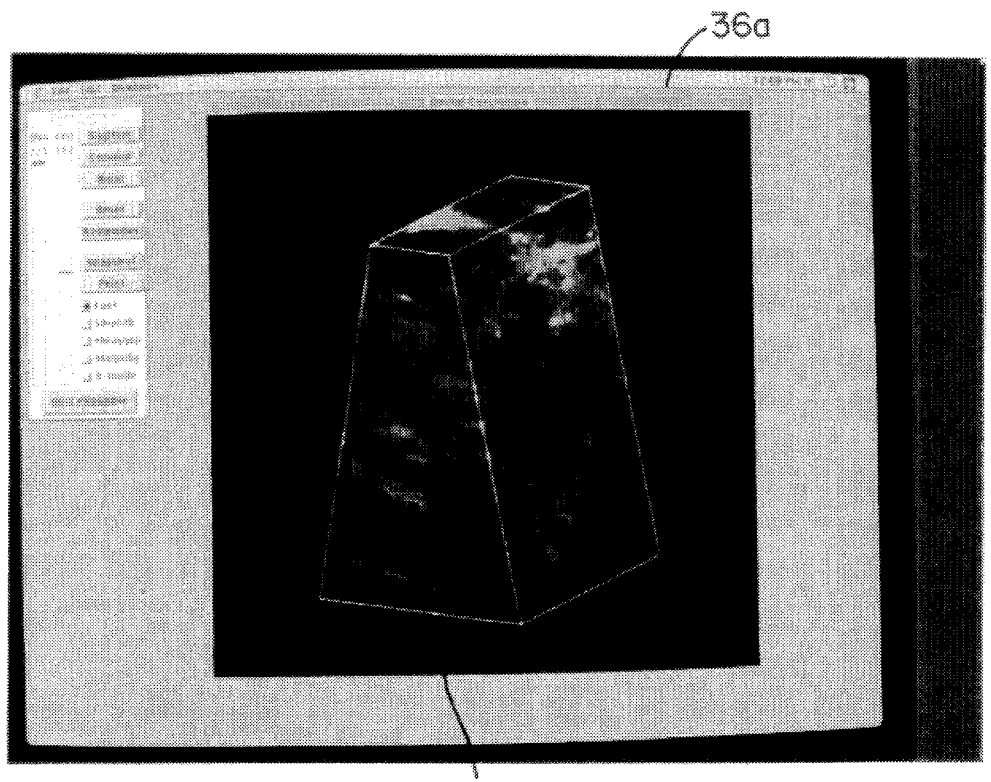
FIG. 26 shows a color typical full screen display including a main display window and a control display window.

The model is then projected on the screen of the monitor 36 within a rectangular sub-region of the full screen display, henceforth called the "main display window" via an orthographic projection (block 316). FIG. 26 illustrates the screen 36a of monitor 36 on which the model and three-dimensional image are displayed within the main display window MDW. It should have been realized that other projection transformations such as a perspective projection may be used to project the model onto the screen. Only the visible faces of the model are displayed on the screen 36a, i.e., hidden-surface elimination is performed so that the displayed model has an opaque appearance. The perimeter lines of the model faces are depicted on the screen by white lines. Each visible model face is projected onto the screen within a polygonal area. Each visible face's polygonal area is divided into an internal area and an external area, the latter being that part of the total area immediately adjacent to the displayed boundary of the face and represents a small portion of the total area.

The display of each visible model face is accomplished as follows. Each screen pixel within the polygonal area of the displayed face has an associated two-dimensional cartesian coordinate pair (x',y'). With precise specifications of the model surface, this can be extended to a three-dimensional coordinate triple (x',y',z').

By means of an appropriate viewing transformation, the pixel coordinates (x',y',z') may be converted to corresponding voxel coordinates (x,y,z), to select a voxel value within the volumetric image array V(x,y,z). The extracted voxel value is indexed into the pseudo-color mapping table to yield a gray-level or color. The gray-level or color in turn is used to illuminate the screen pixel. This process is repeated for all screen pixels located within the displayed model faces (block 318). This technique of display is called "texture mapping", and is known to those of skill in the art.

Each pixel on the display screen is identified by its associated cartesian coordinates (x',y'), which are usually integers. Each voxel in the volumetric image array is identified by its associated array indices (x,y,z), which are also usually integers. For pixels within the perimeter of a displayed model face, it is possible to compute from the pixel coordinates (x',y'), a value z' representing the distance from the plane of the screen 36a to the point on the model face which is projected onto that pixel. In the case of planar faces and using an orthographic or perspective projection, each displayed face has an associated plane equation Ax'+By'+Cz'=D which, given pixel coordinates (x',y'), may be solved to yield the corresponding depth value z'. Other techniques would be required for non-planar model faces, but in general, the problem remains one of solving an equation.

The correspondence between display coordinates (x',y',z') and volumetric image coordinates (x,y,z) is given by the viewing transformation. The particulars of the viewing transformation are re-computed whenever the user decides to change one or more view parameters such as angle of view, display scale, etc. In the case of an orthographic projection and volumetric image arrays sampled on a regular cartesian grid, the viewing transformation is a simple linear mapping. For other cases, such as a perspective projection and/or non-cartesian sampling geometries, the viewing transformation may be more complex. The volumetric image coordinates (x,y,z) computed from display coordinates (x',y',z') via the viewing transformation will not generally be integers, and hence, will not correspond to individual image voxels in the volumetric image array V(x,y,z). In such cases, a voxel value must be computed by interpolation from the nearest available image voxels. This process is called re-sampling, and is known to those of skill in the art. Those of skill in the art will furthermore be aware that a variety of interpolation techniques or "re-sampling methods", are known, and will be aware of their relative advantages and drawbacks.

The preferred embodiment of the present invention performs the display process in multiple passes, using computationally inexpensive resampling methods in earlier passes and progressing to slower, more accurate methods in later passes. It also permits the user to enable or disable selectively, individual passes to choose a satisfactory trade-off between rapidity of response and image fidelity. Furthermore, it is preferred that later passes be interruptible so that if the user requests rapid change of the displayed view, only the earliest passes are performed until such time as there is a pause in user input. At this point, the later passes are performed on the final view only. This technique is called successive refinement and is known to those of skill in the art.

After the three-dimensional image and the model are displayed on the screen 36a of the monitor 36, the initial view is saved in the memory 82 with the image array V(x,y,z) and is indexed as the "Reset" view. Therefore, after initialization, four saved views of the volumetric image array V(x,y,z) exist and can be retrieved from the memory 82 and displayed when an associated icon is selected as will be described. It should be apparent that the number of saved views is arbitrary and that fewer or more saved views may be created and saved. When the initialization is complete, the display module 92 begins to monitor continuously the graphical input device 38 to detect input commands representing desired manipulations to be performed on the displayed image (see FIGS. 20a to 20d). When input commands are detected by the display module 92, the display module manipulates the displayed image in accordance with the received input commands.

All manipulations of the displayed image can be executed via three actions using the graphical input device 38. These actions are termed "point", "click" and "drag". To "point" is to move the graphical input device 38 so that the cursor is positioned on the screen 36a at a desired region without depressing its button. To "click" is to press down on the button of the graphical input device while to "drag" is to move the graphical input device while the button is depressed. The term "point-click-drag sequence" is used to denote the complete action of moving the cursor into a desired region on the screen via the graphical input device, depressing the button on the graphical input device, moving the graphical input device to another desired region with the button depressed and then releasing the button. Specific manipulations of the image are carried out according to the region in which the click aspect of the point-click-drag sequences occur.

Once the initialization routine has been completed and the model and three-dimensional image are displayed on the screen, the graphical input device is monitored to determine whether the user wishes to manipulate the displayed image. The manipulations supported by the display module 92 are rotation of the entire model and three-dimensional image about an arbitrary axis, translation of a selected plane of the model and rotation of a selected plane of the model about an arbitrary axis. The manner in which the display module 92 interprets movement of the graphical input device 38 and manipulates the displayed model and image in response to the graphical input device 38 will now be described.

The display module 92 continuously monitors the graphical input device 38 to determine the position of the cursor on the screen and to determine if a click has occurred. Specifically, the display module 92 determines if the cursor is located within the exterior area of a visible model face (block 324). If the cursor is positioned within such an exterior area, the display module 92 colors the perimeter lines of that model face blue (block 326). Otherwise, the display module 92 changes the color of any perimeter lines which may have been blue to their previous color (block 328). The display module 92 also determines if a click has occurred (block 330). If a click has not occurred, the movement of the graphical input device 38 is tracked. The display module 92 moves the cursor on the screen 36a to follow the movement of the graphical input device (blocks 332 and 334). As the cursor is moved, the display module 92 reverts back to block 324 so that the perimeter lines of the visible faces change colors depending on the location of the cursor as just described.

When a mouse click is detected, the position of the cursor on the screen 36a is examined to determine if the cursor is located within the main display window (block 336). If the cursor is outside of the main display window, the display module 92 determines if the cursor is positioned over an option icon (block 338). If the cursor is not over an option icon, the click is ignored and the graphical input device 38 is monitored until the button is released (block 339). At that time, the display module 92 reverts back to block 324. If however, the cursor is positioned over an option icon, then the display module 92 executes a routine associated with the selected option icon as will be described.

When a graphical input device click occurs and the cursor is positioned within the main display window as detected at block 336, the display module 92 determines whether the cursor is located within the interior area or exterior area of a displayed model face or in the background (block 340). If the cursor is located in the background, the display module 92 determines that the user wishes to rotate the entire model and three-dimensional image. In this case, after the button has been depressed, the drag direction and drag distance of the graphical input device 38 is monitored (block 342). As the graphical input device 38 is being dragged, the drag direction and drag distance are repeatedly conveyed to the display module 92 (block 344). The drag distance and drag direction values are used by the display module 92 to rotate the three-dimensional model and image and to update the display to show the rotation on the screen (block 345). Once the button on the graphical input device 38 has been released, the manipulation is considered complete and the display module 92 reverts to block 324 (block 346).

A variety of techniques for converting mouse drag distance and direction to three-dimensional rotation axis and angle parameters are known to those skilled in the art. The preferred embodiment of the present invention uses Shoemake's "Arcball" technique described in the Proceedings of Graphics Interface 92 published by the Association For Computing Machinery (ACM). The fixed point of rotation for the three-dimensional image is constrained to be the geometric center of the initial model. Thus, in this manipulation, movement of the graphical input device vertically on the screen 36a through the center of the displayed image causes the displayed image to rotate about a horizontal axis, while movement of the graphical input device horizontally through the center 34 of the image causes the displayed image to rotate about a vertical axis.

Figure 21A:
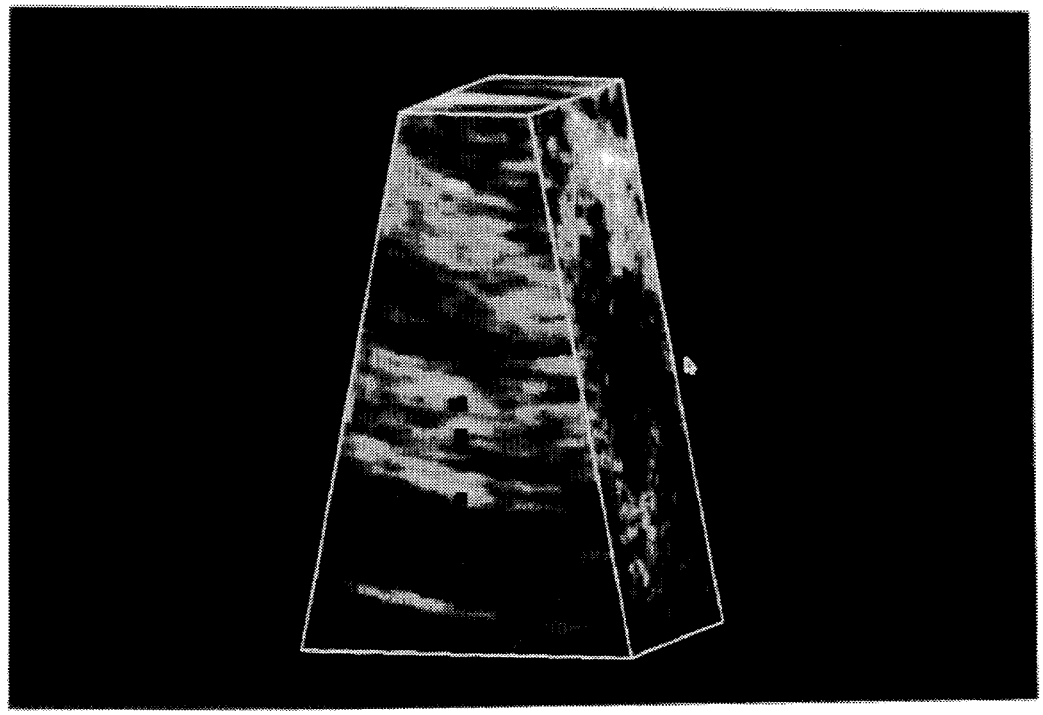
FIGS. 21a to 21c show a color three-dimensional image and model undergoing a rotation about a vertical axis.
Figure 21B:
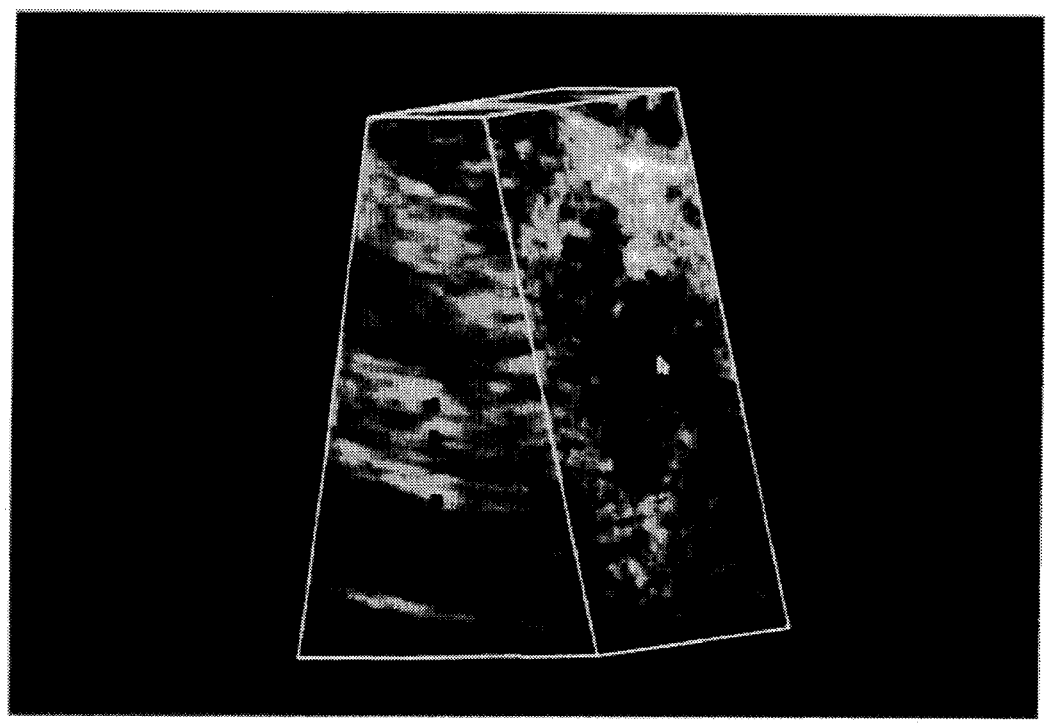
Figure 21C:
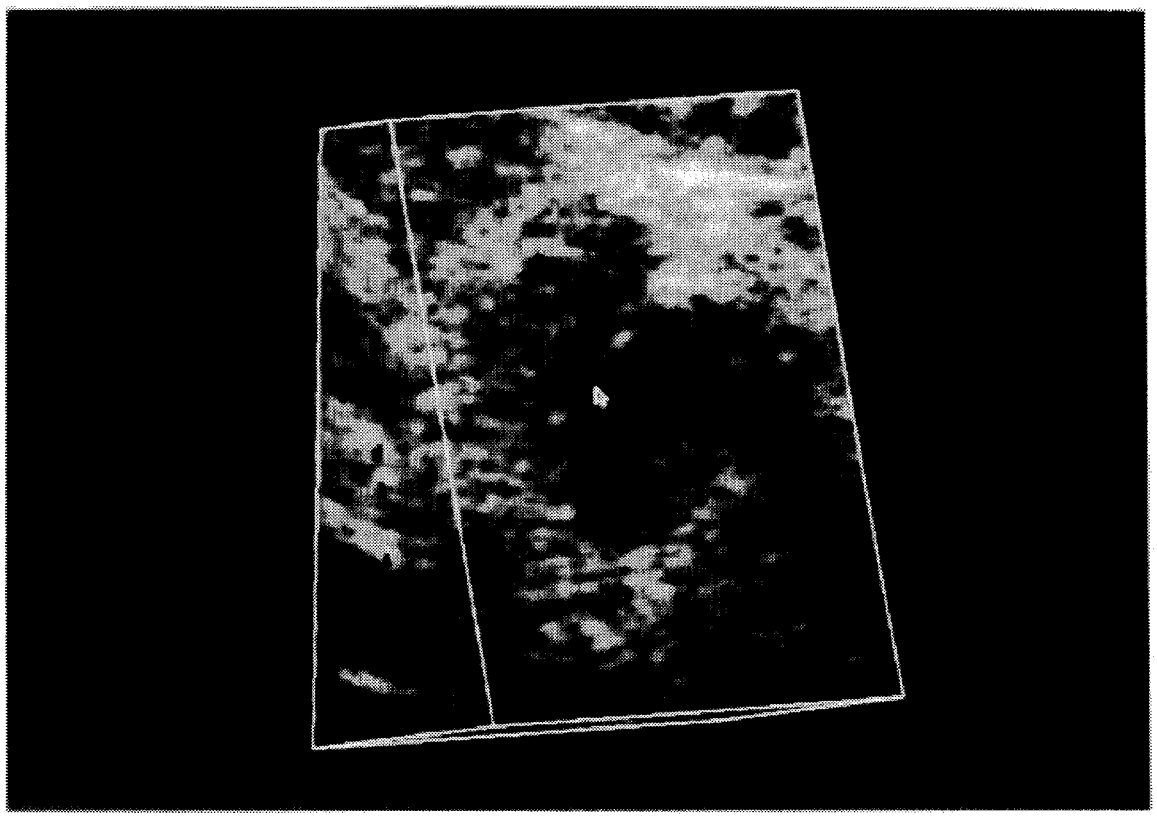
Figure 22A:
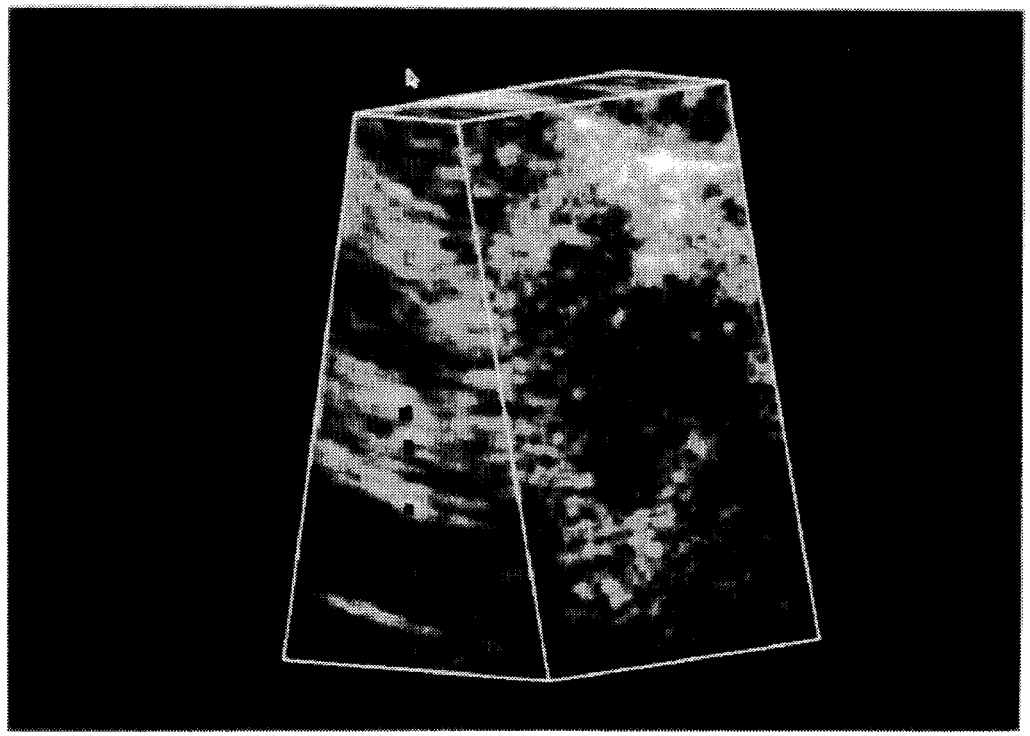
FIGS. 22a to 22c show a color three-dimensional image and model undergoing a rotation in a direction from top-left towards bottom right about an axis, angled at about 30° to the horizontal and sloping up and to the right.
Figure 22B:
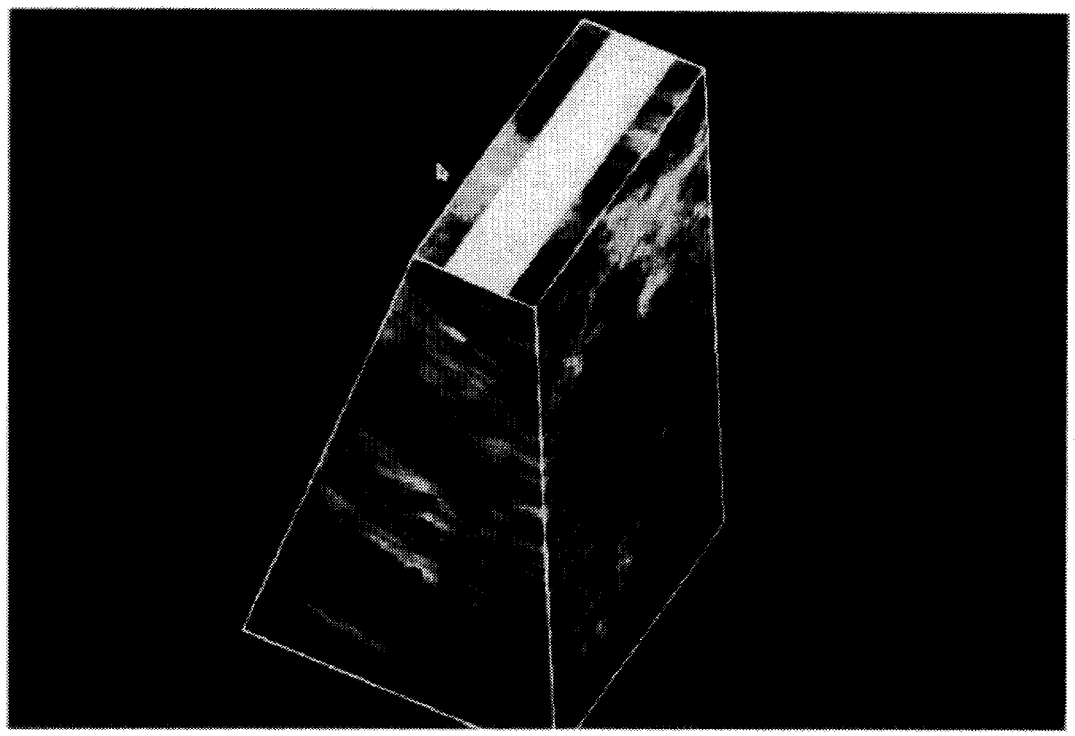
Figure 22C:
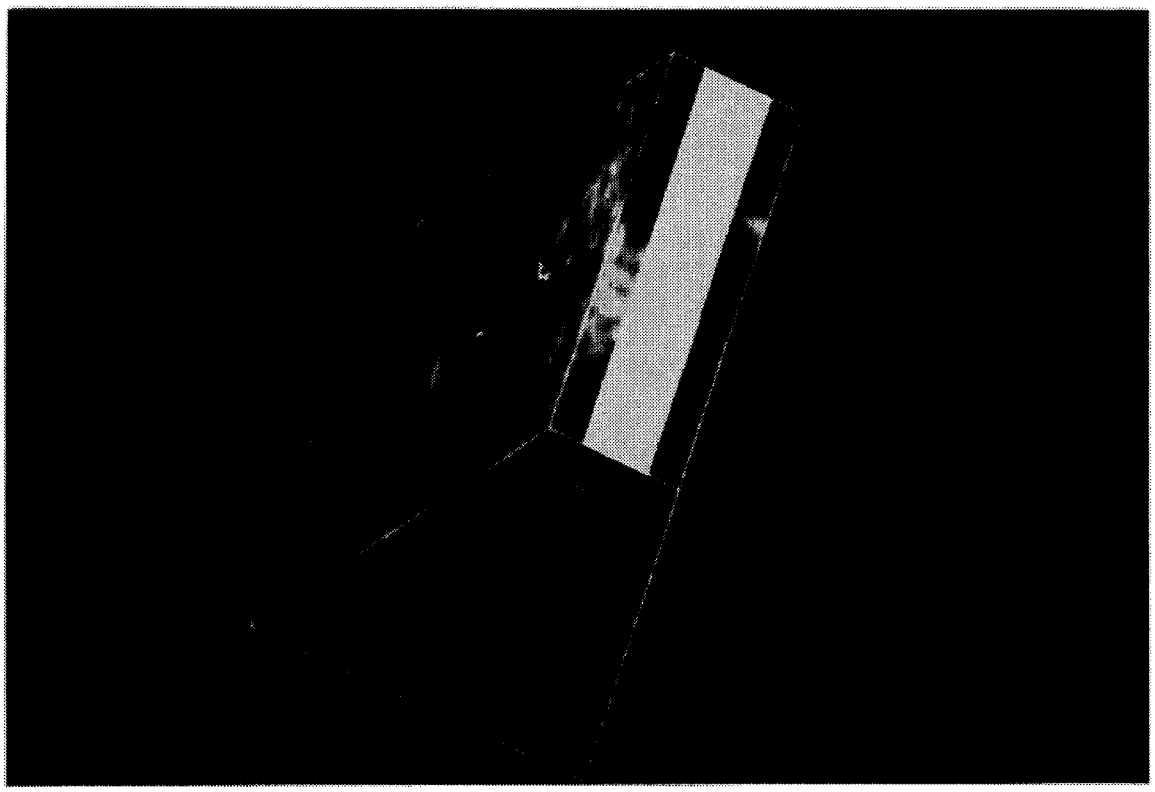

FIGS. 21a to 21c show the model and three-dimensional image within the main window display undergoing a rotation about a vertical axis as the graphical input device 38 is moved to drag the cursor across the main display window from mid-right to mid-left. FIGS. 22a to 22c show the model and three-dimensional image undergoing a rotation about an axis, angled at about 30° to the horizontal and sloping up and to the fight, as the graphical input device 38 is moved to drag the cursor across the main display window from top-left to bottom-right. As should be apparent, this operation gives the user the sense of taking hold of the displayed image and pulling it around. Further details of this image manipulation can be found in the above-mentioned publication.

To facilitate understanding of manipulations of the model other than simple rotation of the entire model, it is necessary to describe the polyhedral model in greater detail. Mathematically, a convex polyhedron can be characterized as the intersection of a set of half-spaces defined by at least four planes, herein called bounding planes. Each face of the polyhedron is a convex polygon embedded in the corresponding bounding plane. By changing the parameters of the bounding planes (i.e. the coefficients A,B,C,D in the plane equation $Ax+By+Cz =D$), the shape of the model polyhedron can be modified. The number of bounding planes may also be changed. Specifically, new bounding planes may be added and existing planes removed from the mathematical specification of the model. The result is that the model polyhedron gains or loses faces.

The display module 92 supports two primary manipulations of bounding plane coefficients, namely translation (change of coefficient D, which essentially specifies the perpendicular distance from the plane to the coordinate origin) and rotation (change of coefficients A,B,C, which collectively specify the orientation of the plane relative to the coordinate axes). As will be described below, the choice of which bounding plane (and hence which corresponding model face) is to be affected, and whether to perform translation or rotation, is determined by contextual interpretation of point-click-drag sequences relative to the displayed model. The display module 92 also provides means to add and delete bounding planes from the model specification, as will also be described below.

A distinction is made between original bounding planes, which are aspects of the model assigned to the volumetric image array $V(x,y,z)$ when it is first loaded into memory (blocks 310 and 312 in FIG. 19) and planes added in response to user input. Model faces corresponding to original bounding planes have their perimeter lines displayed as white lines, while faces corresponding to added planes are indicated using another color, typically yellow or green. Only added planes may be translated, rotated or deleted. The original planes represent the boundaries of the volumetric image and, provide the means to support the addition of new planes.

Figure 20A:
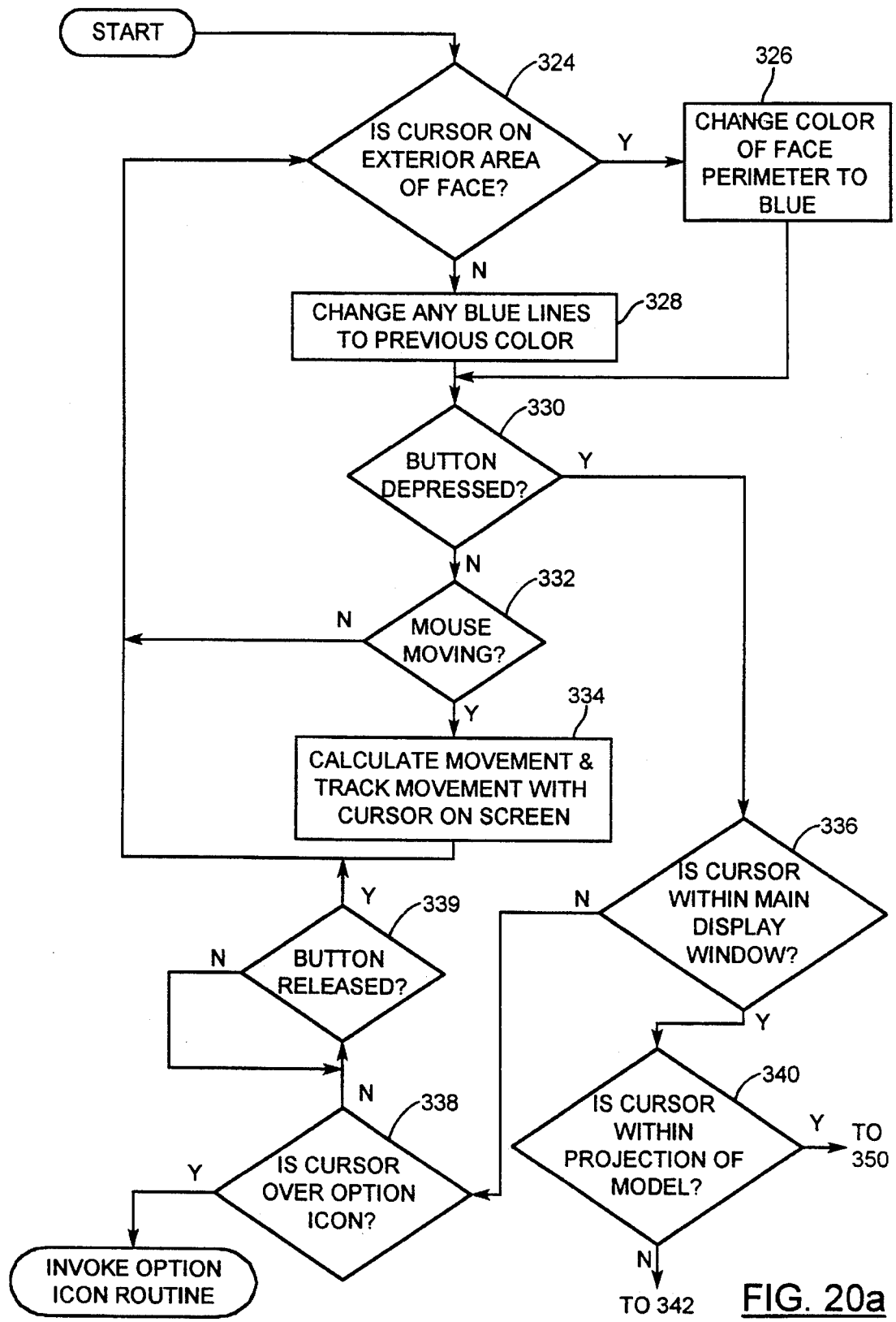
FIGS. 20a to 20d show flowcharts of steps performed by the user interface and display modules when manipulating a displayed three-dimensional image.
Figure 20B:
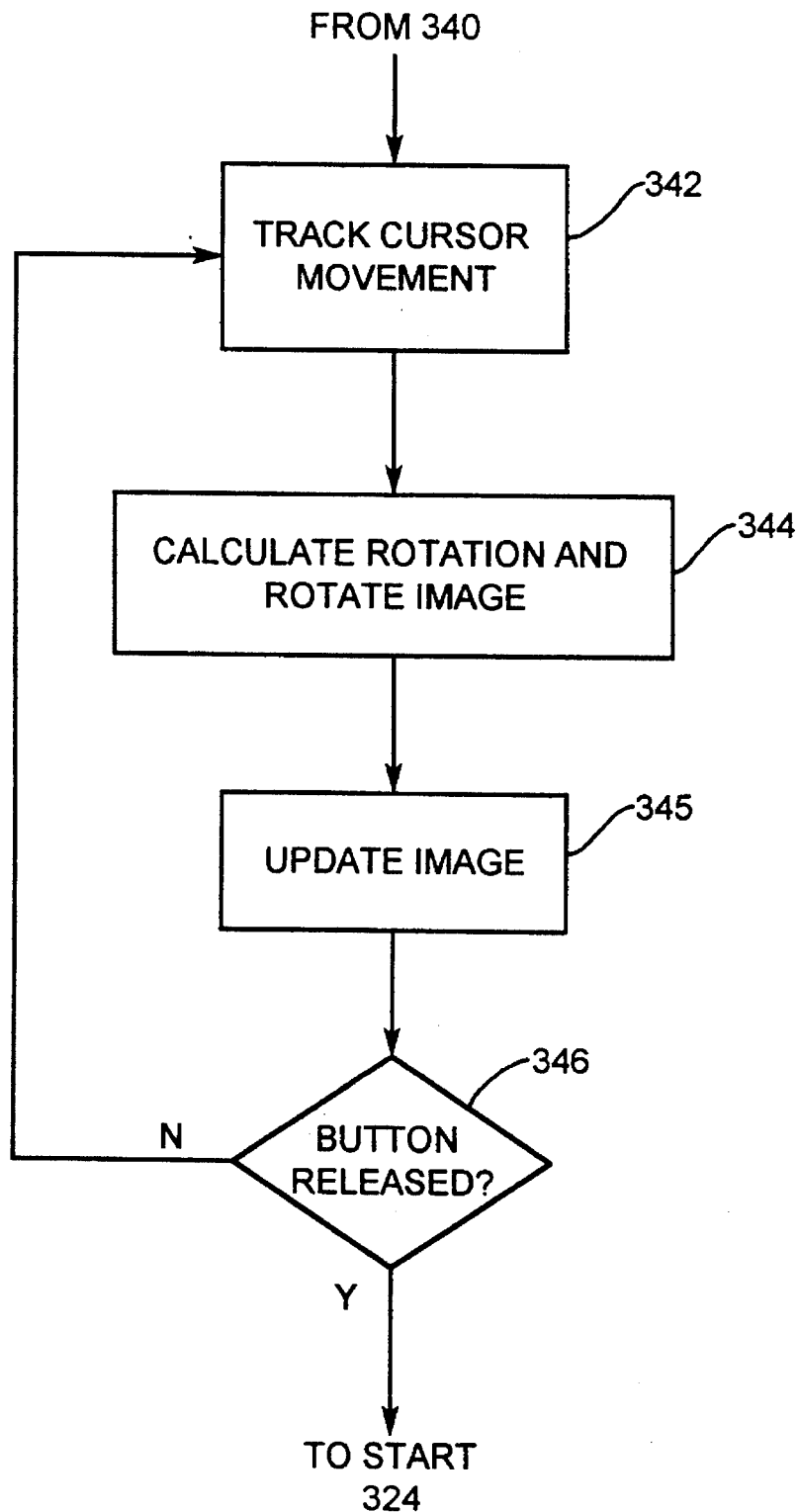
Figure 20C:
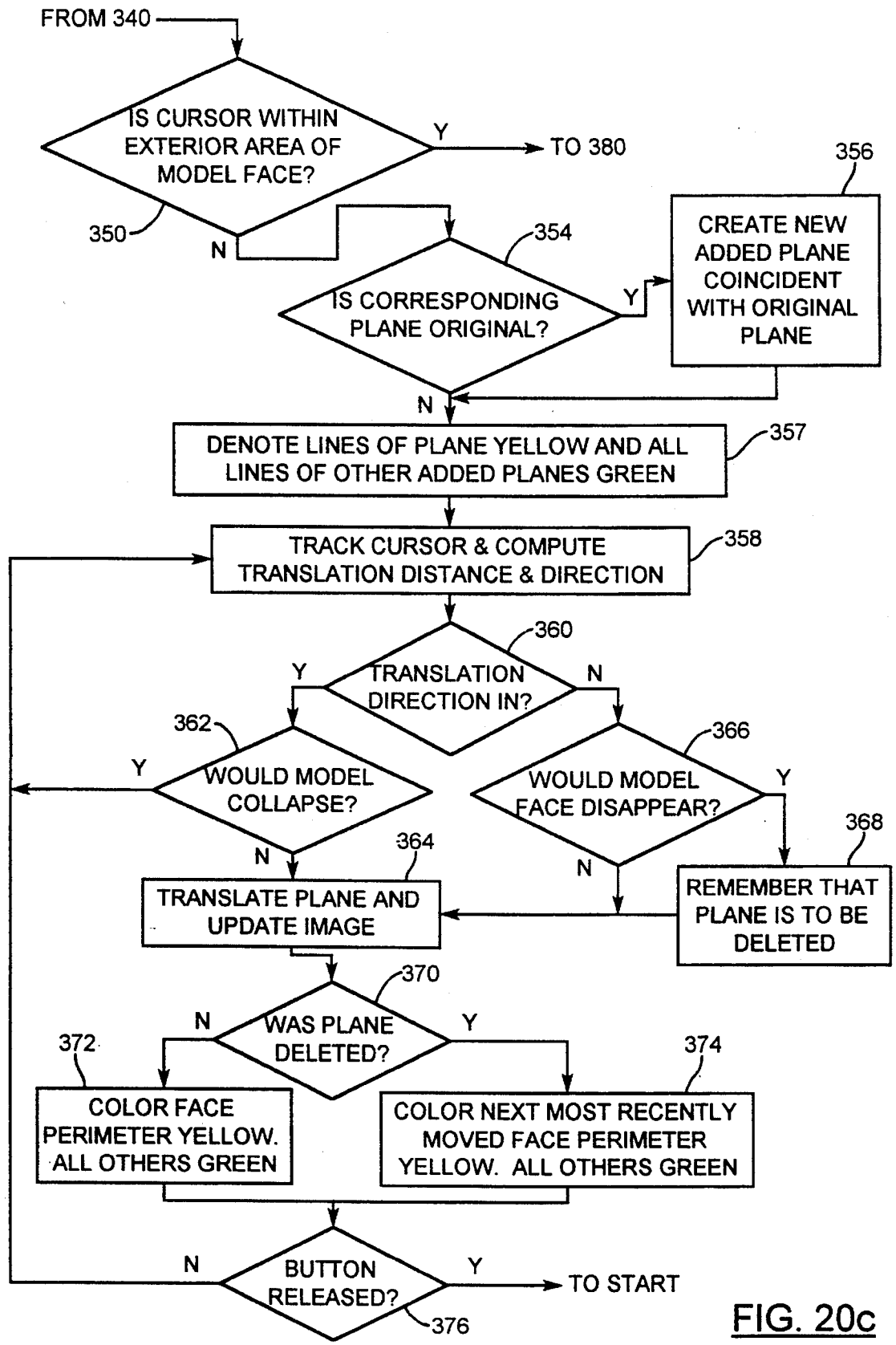
Figure 20D:
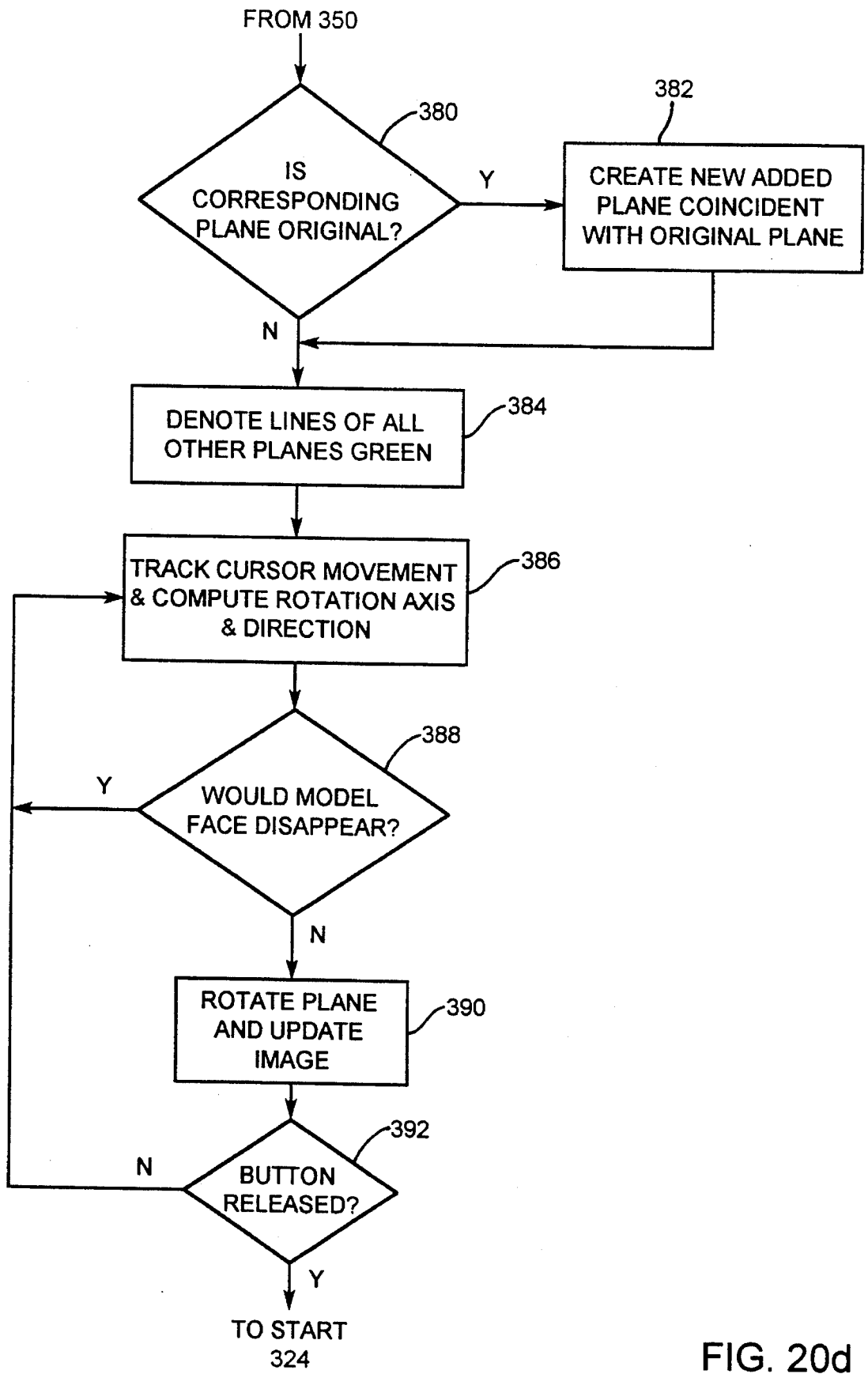

If at block 340, the click is detected and the cursor is determined to be within the perimeter of a displayed model face, the face of the model in which the cursor is positioned is determined and the position of the cursor within the face is examined by the display module 92 (block 350 in FIG. 20c). If the cursor is positioned within the interior area of the face, the display module 92 determines that it is desired to translate the corresponding bounding plane. Thereafter, the display module 92 examines the corresponding plane to determine whether the plane is an original plane i.e. one denoted by white lines (block 354). If the plane is an original plane, a new plane is created and added to the model (block 356). Initially, the added plane is congruent to the original bounding plane. Once the added plane has been created or if at block 354, the plane is not an original plane, the perimeter lines denoting the plane (i.e. the perimeter of the corresponding displayed model face) are colored yellow and all perimeter lines of other added planes are colored green (block 357).

The drag distance and direction of the graphical input device are then monitored (block 358). The display module 92 next determines the direction of translation of the added plane. To do this, the display module 92 calculates the dot product of the drag vector and the projection onto the screen 36a of a normal vector to the plane is computed. If the dot product is positive, the plane is translated in the direction of the normal vector; if negative, it is translated in the opposite direction. In the preferred embodiment, the model specifications are such that all boundary plane normal vectors point away from the interior of the model polyhedron. Hence, movement of the graphical input device 38 which results in a positive dot product pulls the plane outward from the center of the model, while movement of the graphical input device 38 which results in a negative dot product pushes it in (block 360).

If the translation direction of the plane is determined to be in, the display module 92 checks to ensure the translation does not result in the collapse of the model (block 362). If it does, the display model 92 reverts back to block 358 without updating the displayed model and three-dimensional image. Otherwise, translation of the added plane occurs, and the points in the volumetric image array V(x,y,z) which correspond to those on the translated plane are texture-mapped onto the plane (block 364).

If a block 360, the translation direction is determined to be out, the display module 92 checks to see if the translation can result in the plane disappearing (block 366). If not, the display module 92 proceeds to block 364 and updates the displayed model and three-dimensional image. Otherwise, the display module 92 notes that the translation may result in the disappearance of the plane before proceeding to block 364 (block 368). As should be apparent, as a plane is translated, various cross-sections of the image can be viewed as the translated plane slices through the volumetric image array V(x,y,z). Once the plane has been translated, the display module checks to see if the plane was deleted (block 370). If not, the perimeter lines of the translated plane are colored yellow and all other perimeter lines are colored green (block 372). Otherwise, the perimeter lines of the next most recently modified plane are colored yellow and all other perimeter lines are colored green (block 374). When the button is released, the display module 92 considers the translation manipulation complete and reverts back to block 324 (block 376).

Figure 23A:
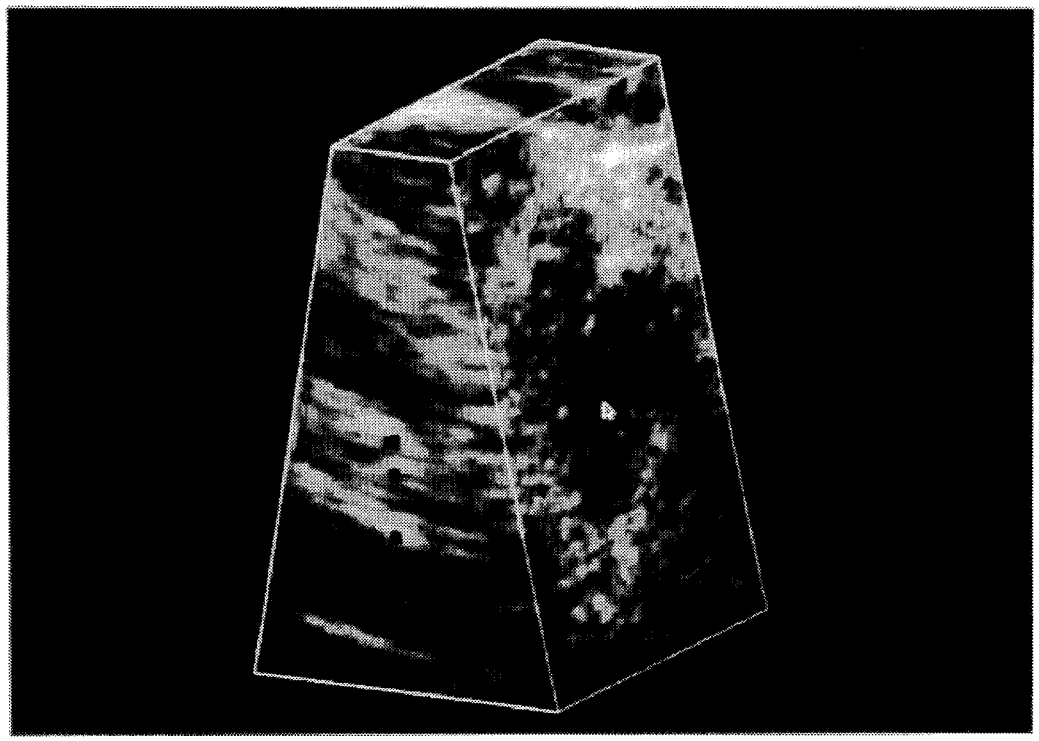
FIGS. 23a to 23c show a color three-dimensional image and model in which a plane of the model is translated towards the geometric center of the model.
Figure 23B:
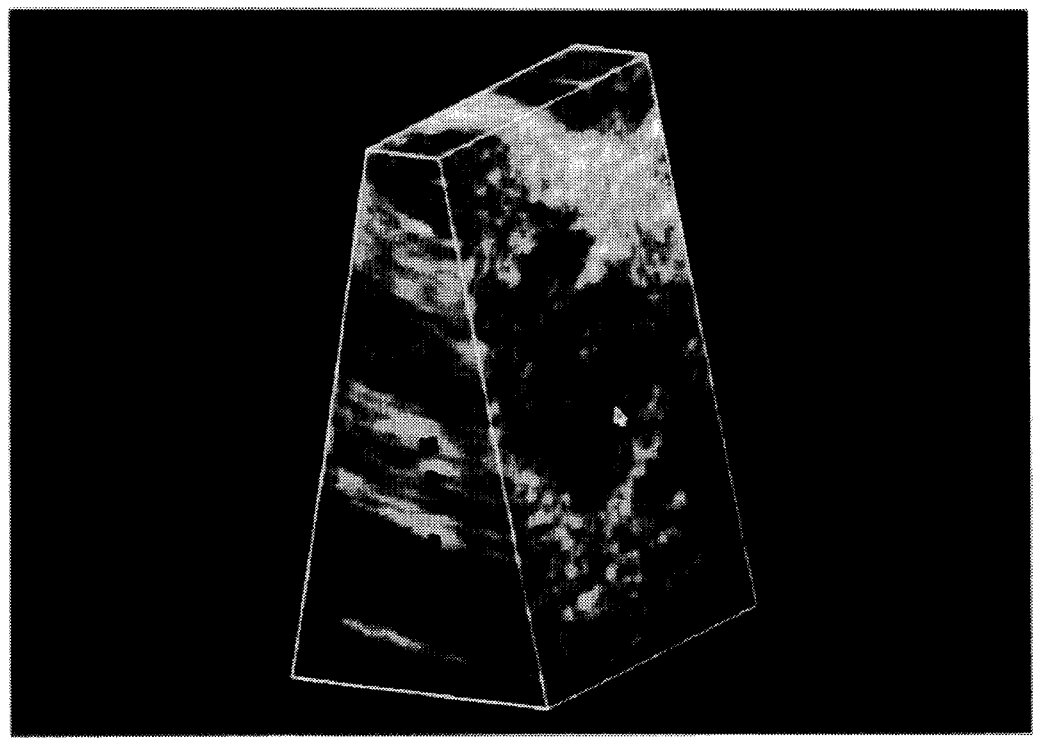
Figure 23C:
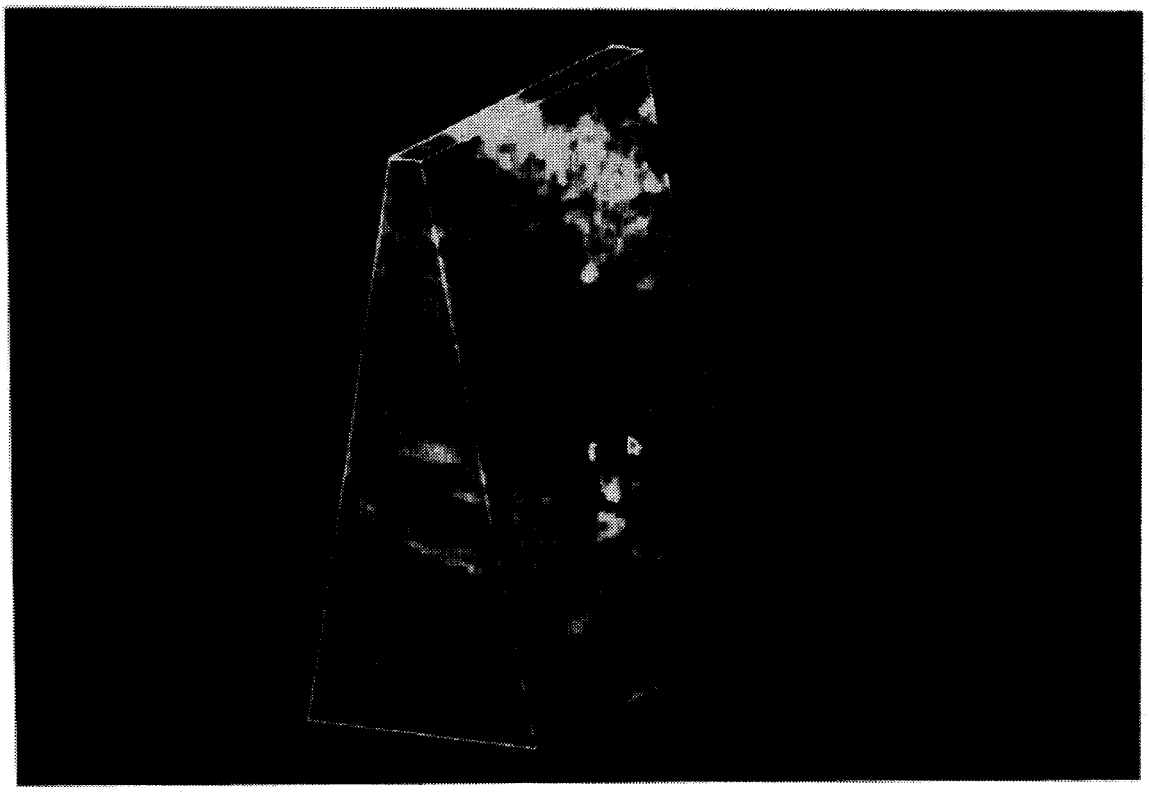

When the added plane which is to be translated is nearly parallel to the plane of the screen 36a, the dot product described above is essentially zero. In such cases, the display module 92 only considers the vertical component of the graphical input device movement to determine the translation direction and distance. In this instance, upward movement of the graphical input device 38 causes the display module 92 to push the added plane into the model 36a while downward movement of the graphical input device causes the display module to pull the plane out of the model. FIGS. 23a to 23c show the model and image within the main display window, wherein a plane of the model is translated towards the geometric center of the model.

When a click is detected and the cursor is positioned within the exterior area of a model face as determined at block 350, the display module 92 determines that the corresponding bounding plane is to be rotated. The display module then examines the plane to determine whether the plane is an original plane (block 380). If the plane is an original plane, a new plane congruent to the original plane is created and added to the model (block 382). The perimeter lines of the added plane are colored yellow. Once this has been done or if at block 380, the plane is not an original plane, the perimeter lines of all other added planes are colored green (block 384).

Figure 24A:
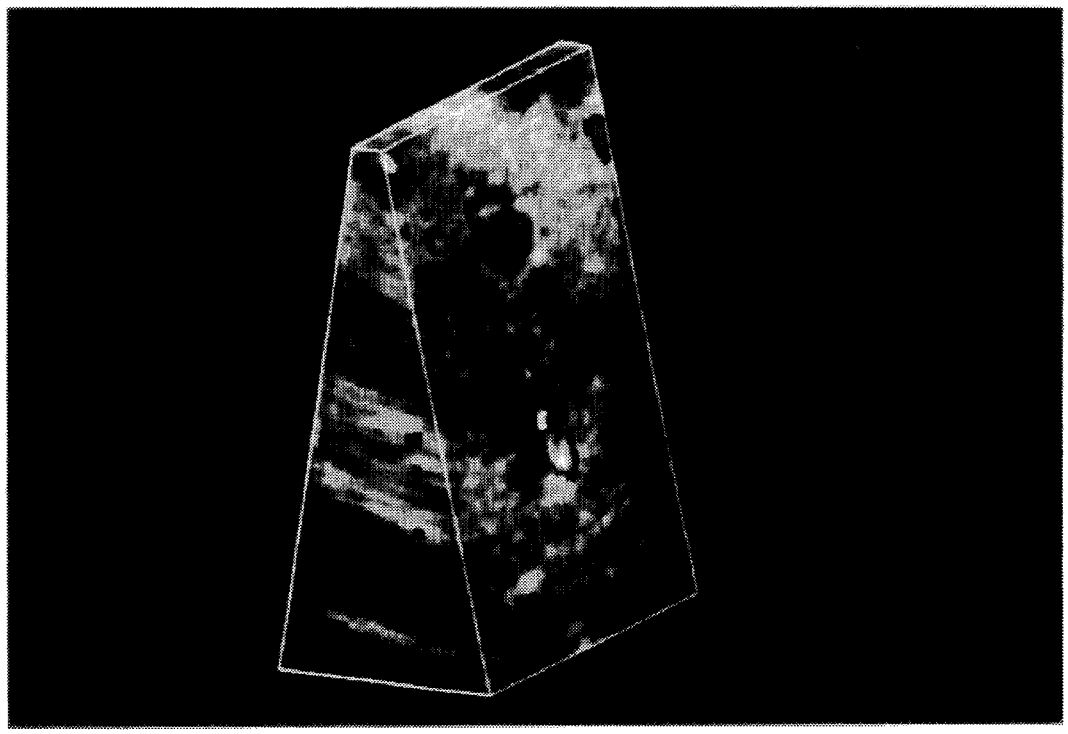
FIGS. 24a to 24c show a color three-dimensional image and model in which a plane of the model is rotated about an axis, angled at about 30° to the horizontal and sloping up and to the right.
Figure 24B:
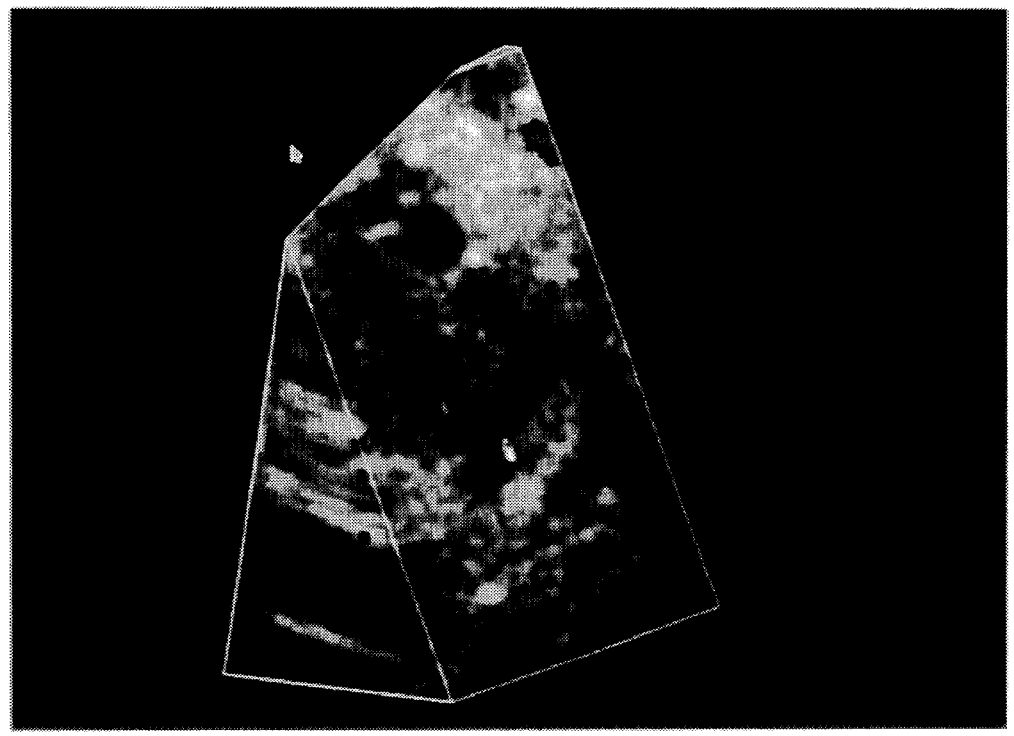
Figure 24C:
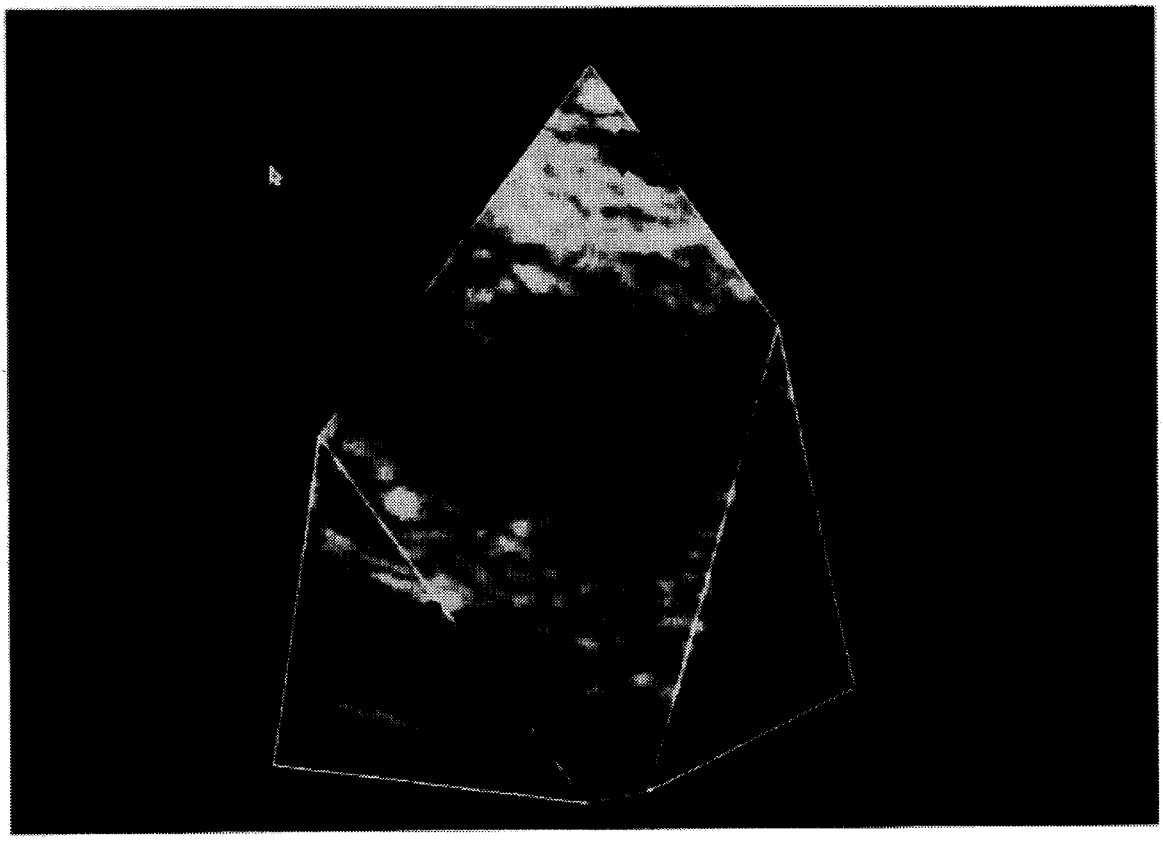
Figure 25A:
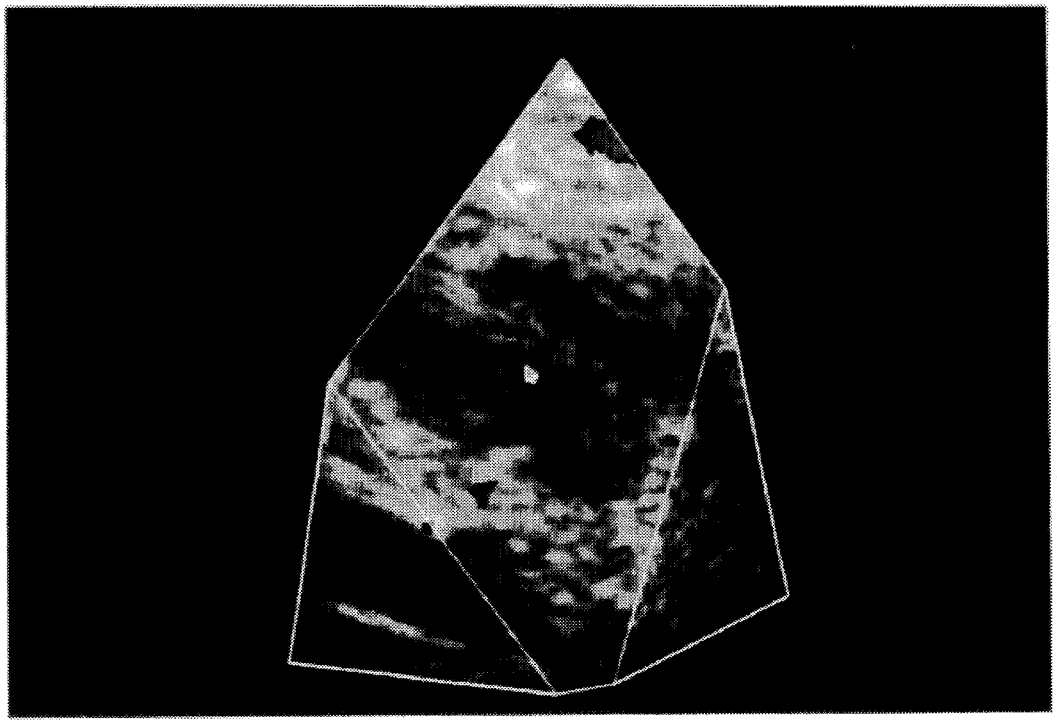
FIGS. 25a to 25d show a color three-dimensional image and model in which a plane of the model is translated away from the geometric center of the model until it disappears.
Figure 25B:
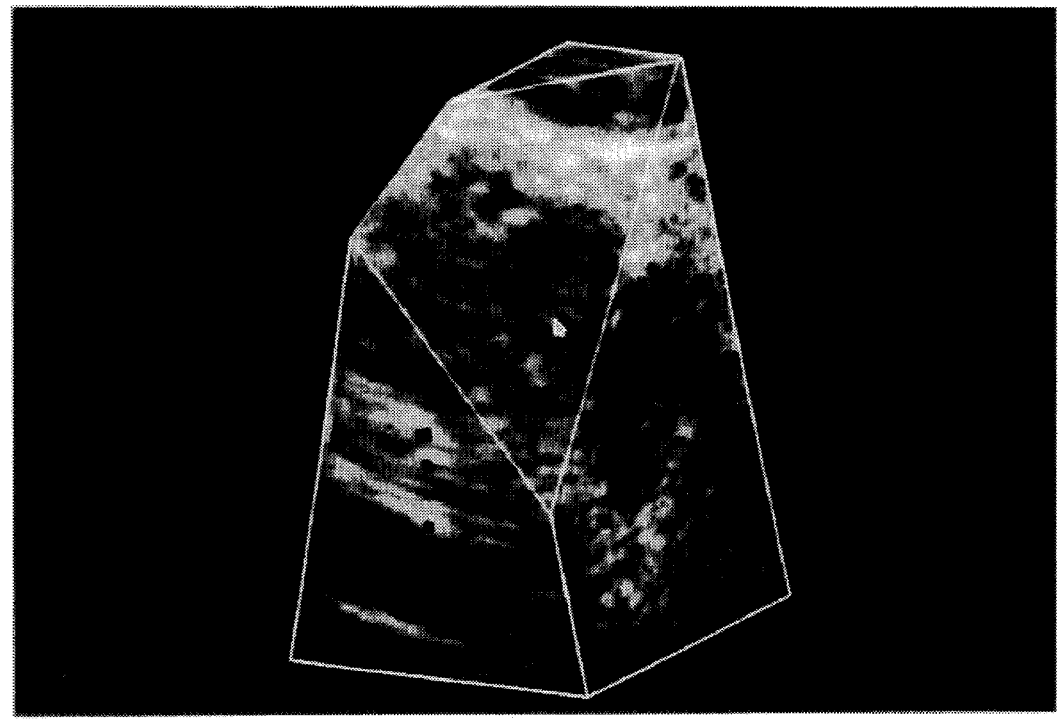
Figure 25C:
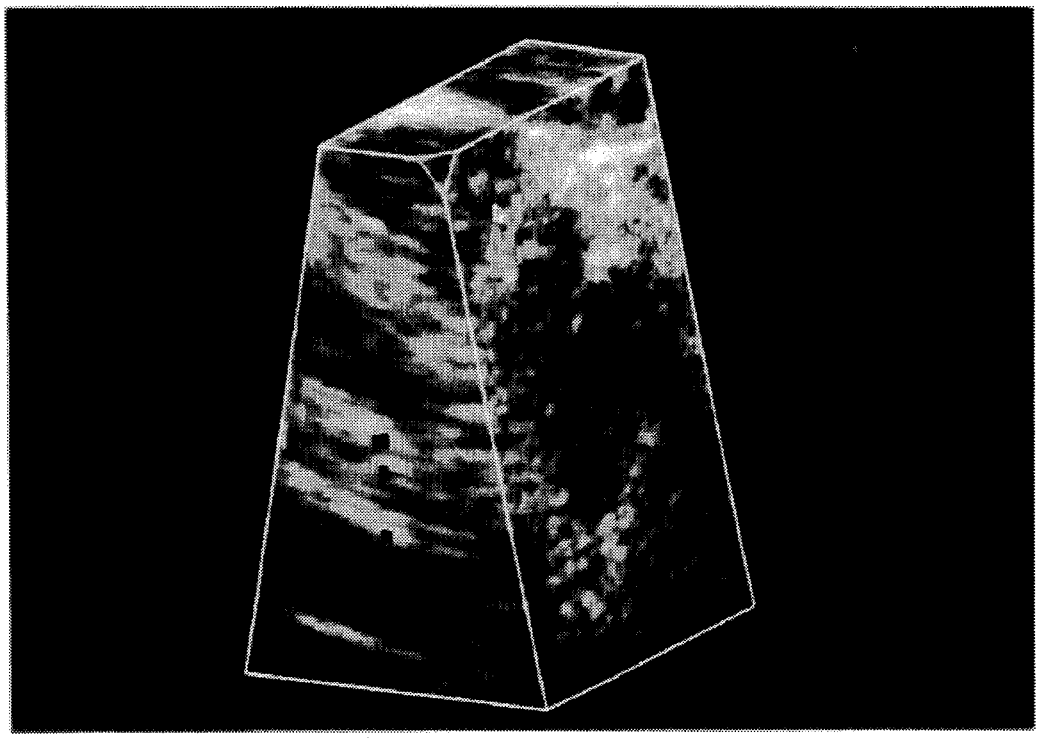
Figure 25D:
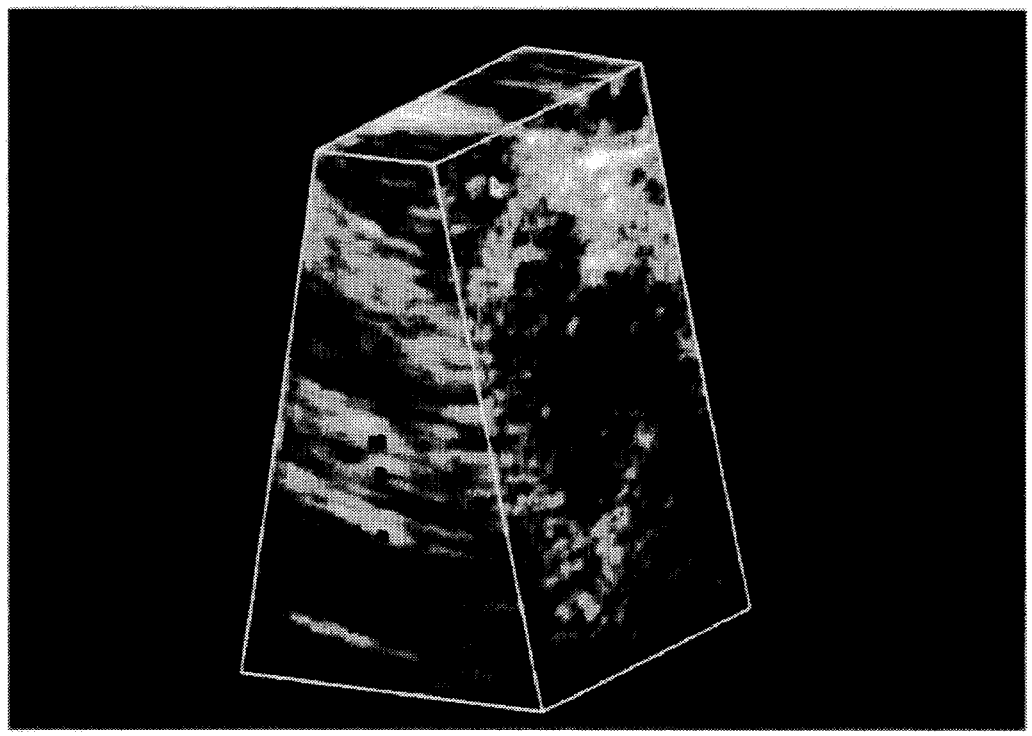

After this, the drag distance and direction of the graphical input device 38 are monitored and the rotation axis and direction of the graphical input device are computed by the display module 92 using Shoemake's technique referred to previously (block 386). After this, the display module 92 determines whether the rotation would cause the plane to disappear (block 388). If so, the display module 92 reverts back to block 386 without updating the displayed model and three-dimensional image. Otherwise, the display module 92 rotates the added plane about the geometric center of the initial model by the calculated amount. As the rotation is occurring, the display module 92 updates the image on the screen (block 390). This allows different cross-sections of the image to be viewed as the rotated plane slices through the volumetric image array V(x,y,z). FIGS. 24a to 24c show the model and three-dimensional image within the main display window, wherein a plane of the model is rotated about an axis, angled at about 30° to the horizontal and sloping up and to the right. It is through this manipulation that new oblique planes may be added to the model. Once the button on the graphical input device 38 has been released signifying that the plane rotation has been completed, the display module 92 reverts to block 324 (block 392).

As should be apparent from the above description, whenever original planes of the model are selected by the user to be translated or rotated, added planes are created and it is the added planes which are moved. The original planes, although not shown on the display screen, remain stored in memory 82 and may be recalled at any time to reset the display to its original state. It should also be apparent that white lines denote an original plane, green lines denote an added plane with the exception of the last moved plane which is denoted by yellow lines and blue lines denote that the plane is going to rotate if a mouse-drag sequence occurs.

When an added plane is rotated, the added plane may become oblique but it is not permitted to extend beyond the boundary defined by the original planes (see FIGS. 24a to 24c). Any added plane can be translated sufficiently far out of the model that its corresponding model face disappears. If the user releases the graphical input device button after the face has disappeared, the plane is removed from the model. This allows a user to delete unwanted added planes. If the graphical input device button is not released, the user can push the added plane back into the model so that the plane becomes visible again and no deletion takes place. FIGS. 25a to 25d show the model and three-dimensional image within the main window display wherein an oblique plane of the model is translated away from the geometric center of the model until it disappears. Although it would seem that if an added plane is translated sufficiently into the model, the entire model can collapse, the display module 92 does not permit an added plane to be translated so far as to collapse the model (see block 362).

While the graphical input device 38 is being moved to effect changes in the displayed view and the display is updated showing intermediate positions and orientations of the affected plane or planes, the display module 92 must re-sample the volumetric image array V(x,y,z) and complete the texture mapping process, a process of discrete approximation. In this embodiment, a number of re-sampling methods are available, each of which offers a different compromise between computational speed and image quality.

To achieve smooth operation with limited computer power, the display may be computed (rendered) at less than the full resolution of the monitor screen and/or a simpler interpolation technique may be employed in the re-sampling process. In this embodiment, the display is computed in as many as three rendering passes, the first and third of which may be disabled if the user so wishes, by selecting the appropriate option icon via the graphical input device 38. The enabled/disabled status of each pass is what is actually set to a default state at block 324 during initialization. The first enabled pass in the sequence is uninterruptible, i.e. while the graphical input device is being moved, the first enabled pass is performed in its entirety, yielding a succession of complete views on the screen. Subsequent enabled passes are automatically interrupted by graphical input device movement, the visible result being that the displayed view is only replaced by a higher quality view (computed by an interruptible rendering pass) when there is a sufficient pause in graphical input device movement. The three rendering passes supported by the present embodiment are:
1. reduced image reduction, nearest-neighbour re-sampling
2. full image resolution, nearest-neighbour re-sampling
3. full image resolution, tri-linear interpolation re-sampling As mentioned previously, at block 338, if a click is detected and the cursor is not positioned in the main display window, the display module 92 determines whether an option icon has been selected. The available option icons allow the user to select parameters different from the default values, to enhance image display and to execute special feature routines. These option icons include "Reset", "Views A to C", "Remember", "Snapshot", "Animation", "Indicator", "Orientation", "Fast", "Smooth", "Win", "Lev", "Magnify" and "Measure". FIG. 26 illustrates most of these option icons in a control display window positioned beside the main display window. In this example, the preferred Views A to C have been labelled by the user as "Sagittal", "Coronal" and "Axial". The available options which can be selected via an option icon will now be described.

If the Reset icon is selected, the original view of the image and model stored with the volumetric image array V(x,y,z) is recomputed and displayed on the screen. Likewise, if one of View A to C icons is selected, the corresponding preferred view is recomputed and displayed. If the user wishes to change one or more of the Views A to C for a current session, the user can substitute the displayed view for the stored view. The present embodiment permits the user to activate a distinct window in which the View icon labels (e.g. Sagittal, Coronal, Axial etc. in FIG. 26) are displayed and to edit the labels as desired. Changes made to the labels persist only for the current session, unless the user elects to save the changes in memory 88 using an option icon provided for that purpose, in which case any preferred Views associated with the data file are overwritten.

If the Remember icon is selected, the current view on the screen is stored in memory 82 overwriting the "Reset" view for the current session only. The "Reset" view associated with the current data file in memory 88 is not changed, only the copy in memory 82. This view may be recalled to the screen at any time by selecting the Reset icon, unless and until it is overwritten by a subsequent use of the Remember icon.

It should be realized that a similar two-icon technique can be used for Preferred Views A to C. However, the present embodiment allows the user to overwrite these views in memory 82 by holding down a specified key on the keyboard while selecting the corresponding View icon.

If the Snapshot icon is selected at any time during manipulation of the model and image, the image currently displayed in the main display window is stored as a file in memory 88 in an industry-standard image file format, in order that it be may subsequently be used with other software. The present embodiment uses a tagged image file format ("TIFF"). It should be realized that adding support for other file formats can be achieved in a straightforward manner by following published format specifications.

If the Animation icon is selected, animated sequences of displayed views can be created and saved into memory 82 in an industry-standard image format as just described. When the Animation icon is selected, the display module 92 determines whether a view of the image has been saved using the Remember icon and retrieves it. If no view has been saved using the Remember icon, the original view is retrieved. While this is occurring, an animation display window appears on the screen 36a. The display window allows the user to select the number of intermediate views of the displayed image which are to be computed and displayed (see FIG. 27). The animation display window also allows the user to adjust the image size, assign an identifier to the animation sequence and preview the animation to ensure that the selected parameters are satisfactory. After this, the display module 92 computes the view orientation, position and orientation of each plane of the intermediate views by simultaneous interpolation between the saved and current views.

By using simultaneous interpolation, the user need only enter two views making the use of the feature very simple. Secondly it allows complicated view sequences to be produced which cannot be produced manually. When altering an image manually, a plane may be either rotated or translated but not translated and rotated at the same time. Simultaneous interpolation of plane position and orientation makes it possible to produce an animated view sequence in which a plane is rotated and translated at the same time. As should be realized, this feature as described can only be implemented when the current and saved views have the same number of planes.

If the Indicator icon is selected, the model is displayed with axis indicators to indicate standard directions of the image, such as front F, back B, left L etc. These symbols may be changed by the user to suit the application. For example, in ophthalmic imaging the symbols can represent the standard ocular axes, namely superior S, inferior I, nasal N and temporal T. These indicators float as the view of the displayed image changes. To avoid cluttering, it is preferred that axis indicators disappear when the current view orientation would place then behind the displayed model.

Figure 28A:
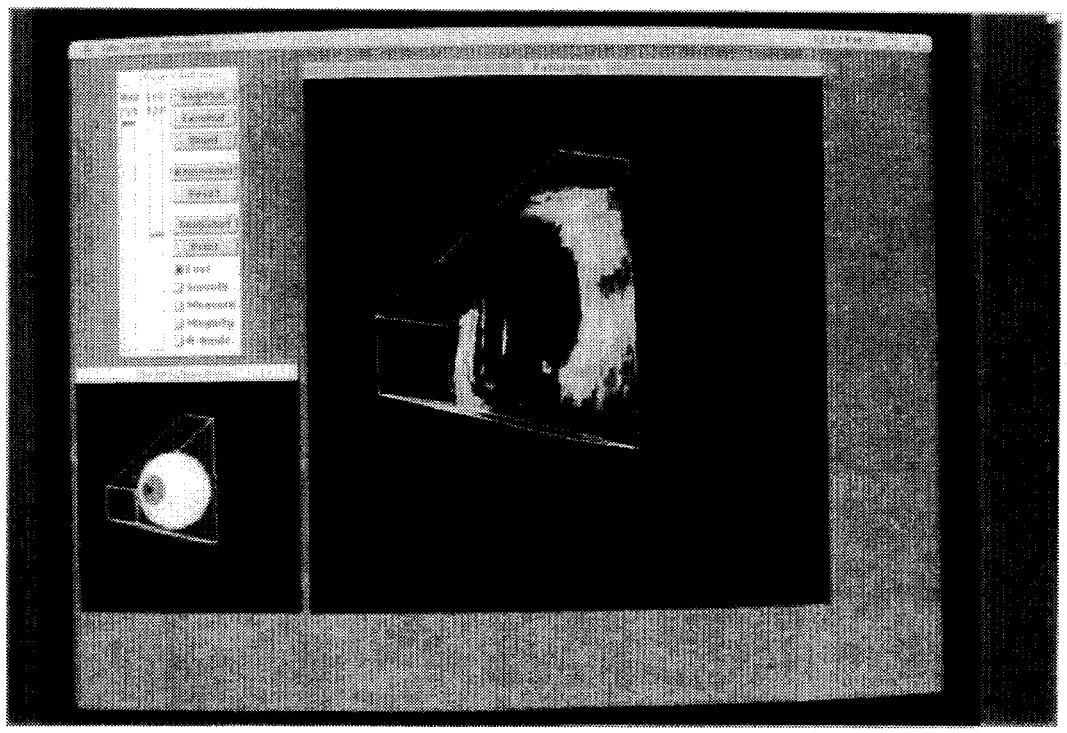
FIGS. 28a to 28c show color full screen displays further including an orientation view window.
Figure 28B:
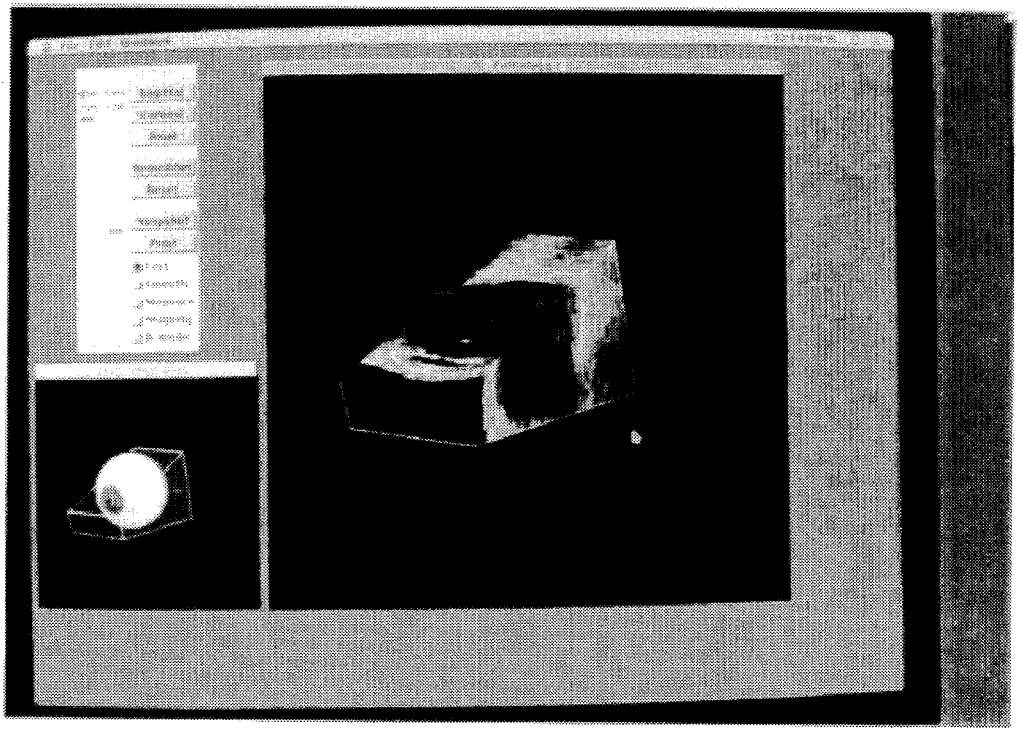
Figure 28C:
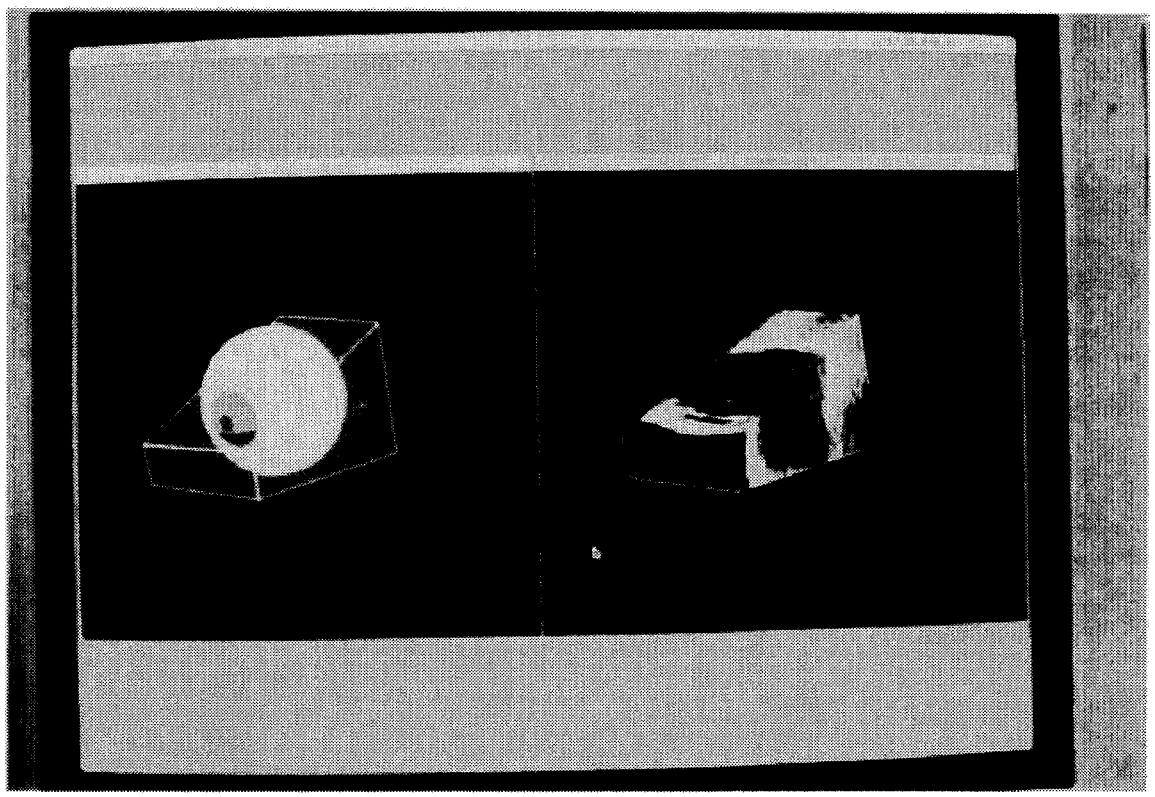

In some applications such as in medical imaging, it is desired to show the current spatial relationship of the model to a representation of the structure which has been imaged. This can be achieved when the Orientation icon is selected. When this icon is selected, the representation of the structure being imaged is selected from a list of stored structures. The structure is modelled using conventional three-dimensional computer graphics techniques. The structure is then displayed as a semi-transparent solid object intersecting the model polyhedron, either in the main display window or in a second display window elsewhere on the monitor screen. This requires use of a rendering algorithm which makes it apparent how the structure and model polyhedron intersect. The position, size and spatial orientation of the structure relative to the model polyhedron, which may be expressed as a 4×4 transformation matrix, must be determined. When this icon is selected, the structure display window is updated as the user manipulates the displayed view, so that the two displays are always oriented in the same manner. When computer power is limited, it is permissible to update the structure display less frequently then the main display window, e.g. to suppress updating the former until there is a pause in user input. This approach, which works best when the structure is displayed in a window distinct from the main window, is used in the present embodiment. FIGS. 28a to 28c show the model and three-dimensional image within the main window display as well as the structure of an eye in a second display window beside the main window display. As can be seen, in FIGS. 28a and 28b, the second display window is small and is positioned below the control display window while in FIG. 28c, the second display window has been increased in size.

The Fast and Smooth icons may be individually selected or deselected to enable or disable the first and third rendering passes described previously (the second pass is always enabled). The initial state of these icons is established during initialization at block 324. It should be realized that this general scheme can be altered slightly, e.g. by addition of a fourth pass with a corresponding option icon to selectively enable or disable it if desired.

Each displayed point of the image array V(x,y,z) is converted to a pixel brightness or color by pseudo-color mapping. The domain of the pseudo-color mapping is the range of values in the volumetric image array V(x,y,z). The pseudo-color mapping can be adjusted by a user via the window and level slide controls (labelled "Win" and "Lev" in FIGS. 26 to 28) to allow the contrast, brightness etc. of the display to be enhanced. The terms "window" and "level" and their interpretation have become standardized in the medical imaging field. The present embodiment is consistent with established medical imaging practice in this regard.

When the Magnify icon is selected, a magnifying window appears superimposed upon the main display window and can be moved over the displayed view. Cross-hairs are located at the center of the window and can be positioned over a certain area of the displayed view. When the cross-hairs are at the appropriate location, the user can use the graphical input device to adjust the magnification of the area at which the cross-hairs are located.

Figure 27:
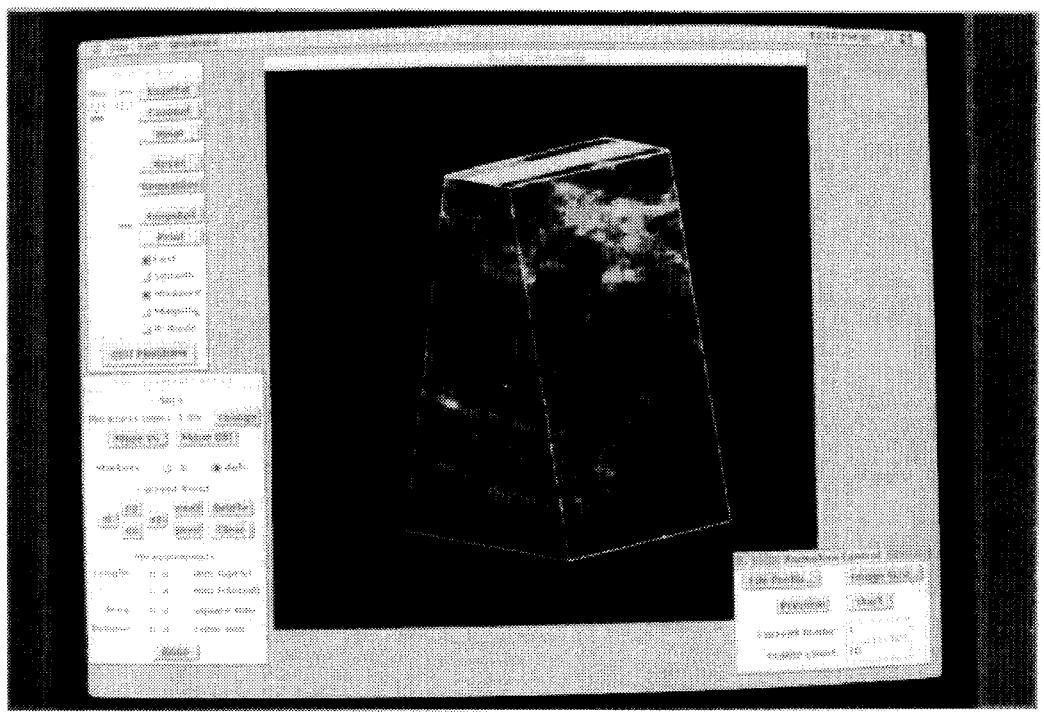
FIG. 27 shows another color full screen display further including a measure control window and an animation control window.

When the Measure icon is selected, a measure display window appears on the screen (see FIG. 27). The user can use the graphical input device to measure distances and areas of the three-dimensional image within the most recently moved plane (i.e. the one denoted by yellow lines). If the user wishes to measure a distance, the user simply needs to use the graphical input device 38 to indicate the two end points over which the distance is to be measured. If an area is to be measured, the user must identify at least three points. When the cursor is moved over the most recently moved plane, it changes to cross-hairs to facilitate placement of the points on the image. The display module 92 in this mode connects adjacent points by straight line segments and computes both the overall line length and the area bounded by the lines joining the points using an appropriate scale.

If it is desired to change the drag sensitivity, the user can depress a specified key on the keyboard and this will adjust the scaling factor for as long as the key is depressed. This allows for greater or smaller mouse movements for a given change in the displayed image. This of course can also be achieved by increasing or decreasing the size of the main display window.

Although the animation function has been described to animate a sequence of translated and/or rotated images, the cine loop technique may also be applied to visualize four dimensional image arrays. In this case, the four-dimensional image arrays are a series of three-dimensional images of the same target volume, acquired at different times. For example in trans-oesophageal cardiac ultrasound imaging, it is possible to capture and reconstruct a plurality of images of the beating heart, each corresponding to a different point in the cardiac cycle. The three-dimensional images will all have the same spatial interpretation and hence, it is possible to impose a single bounding model upon all of them simultaneously. The intersection of the model polyhedron with each volume image yields a two-dimensional image. The images can be computed and displayed in time order as a cine loop.

Although the system has been described as including a single button mouse to allow a user to input commands, it should be apparent to those of skill in the art that other input/output devices such as a multi-button mouse, a digitizer, a light pen, a trackball, a keyboard or the like or any combination of the above can be used. When other input/output devices are used, different inputs can be chosen to represent different commands or to select the various option icons.

When a graphical input device other than the single button mouse is used, manipulation of an image by rotation of a plane of the model can be enhanced. For example, if a mouse is used in combination with a keyboard and a keyboard input is used to signify that it is desired to rotate a plane, the fixed point of rotation of the plane can be determined by the position of the mouse when it is clicked and the keyboard input signifying rotation of the plane is selected. This allows the plane to be rotated about a point different from the geometric center of the initial model.

If a two button mouse is used as the input/output device, one of the buttons can be assigned to signify translation of a plane and the other button can be used to signify rotation of a plane. This avoids the need to examine the position of the cursor to determine whether it is within interior or exterior areas of the selected model face.

Although the three-dimensional image display technique has been described in an ultrasound three-dimensional imaging system, it should be apparent that the image display technique may be used in different environments where a three-dimensional image needs to be manipulated to allow different views of the image to be visualized. Specifically, the present display technique can be used to display any volumetric image array V(x,y,z) which represents a discretely sampled function defined over a three-dimensional space. This allows the display technique to be used in other environments such as, for example, magnetic resonance imaging (MRI) and x-ray computed tomography Although the system 20 has been described as including a clinical ultrasound machine 28 and a computer 32, it is contemplated that a single machine be used to perform the functions of both of these components.

Variations and modifications of the present invention should be apparent to those of skill in the art without departing from the scope of the present invention as defined by the dependant claims.

We claim:

1. A method for conveying two-dimensional images of a target volume represented by an array of pixels I(x,y,z) into a three-dimensional image represented by a volumetric image array V(x,y,z) comprising the steps of:

(i) transforming said array of pixels I(x,y,z) into an image array R(x,y,z) so that each z-slice A(x,y) of image array R(x,y,z) provides sufficient image data to construct an image slice;

(ii) extracting a z-slice A(x,y) of image array R(x,y,z) and computing the position of each pixel of z-slice A(x,y) in a volumetric image array V(x,y,z);

(iii) mapping a gray-level or color of the pixels of z-slice A(x,y) into corresponding pixels of said volumetric image array;

(iv) repeating steps (ii) and (iii) until all z-slices A(x,y) of image array R(x,y,z) have been processed to complete said volumetric image array; and (v) compensating for at least one hardware offset affecting said volumetric image array which occurred when said two-dimensional images were taken.

2. The method of claim 1 wherein said at least one hardware offset is an image-tilt offset, said step of compensating (v) being performed prior to step (i) and including the step of rotating the pixels of array I(x,y,z) to compensate for said image-tilt offset.

3. The method of claim 1 wherein said at least one hardware offset is a displacement offset, said step of compensating (v) being performed at step (iii) and including the step of adjusting the position of pixels from z-slice A(x,y) in the said volumetric image array prior to performing step (iii).

4. The method of claim 3 wherein said at least one hardware offset further includes a tilting offset, said step of compensating (v) being _performed at step (iii) and including the step of adjusting the position of pixels from z-slice A(x,y) in the said volumetric image array prior to performing step (iii).

5. The method of claim 1 wherein said at least one hardware offset includes image-tilt offset, displacement offset and tilting offset, said step of compensating (v) including the steps of (vi) rotating the pixels of array I(x,y,z) prior to step (i) to compensate for said image-tilt offset, and (vii) adjusting the position of pixels from z-slice A(x,y) in the said volumetric image array prior to performing step (iii) to compensate for said displacement and tilting offsets.

6. The method of claim 5 further including the step of (viii) compensating for shadowing effects.

7. The method of claim 6 wherein said step (viii) includes the steps of (ix) separating the pixels of z-slice A(x,y) into two parts, (x) computing the position of each pixel of each part in the said volumetric image array, (xi) computing and storing gray-levels or colors of the pixels in temporary rasters H(x,y) and K(x,y) associated with a respective one of said parts, (xii) superimposing said temporary rasters after step (xi) has been completed and (xiii) mapping the computed gray-levels or colors of the pixels in the superimposition to corresponding pixels in said volumetric image array.

8. The method of claim 7 wherein the pixels in said superimposition are mapped into a temporary raster T(x,y) before being mapped into said volumetric image array.

9. A system for convening two-dimensional images of a target volume represented by an array of pixels I(x,y,z) into a three-dimensional image represented by a volumetric image array V(x,y,z) comprising:

means to transform said array of pixels I(x,y,z) into an image array R(x,y,z) so that each z-slice A(x,y) of image array R(x,y,z) provides sufficient image data to construct an image slice;

means to extract each z-slice A(x,y) of image array R(x,y,z) and compute the position of each pixel of each z-slice A(x,y) in a volumetric image array;

means to compute and store a gray-level or color for each of the pixels of each z-slice A(x,y);

means to map the computed gray-levels or colors into corresponding pixels of said volumetric image array V(x,y,z); and means to compensate for at least one hardware offset affecting said array of pixels I(x,y,z) which occurred when said two-dimensional images were taken.

10. A system as defined in claim 9 wherein said means to compensate adjusts said array of pixels I(x,y,z) to compensate for image-flit offset, and adjusts the position of pixels of each z-slice prior to the gray-levels or colors being mapped to the volumetric image array to compensate for displacement and tilting offsets.

11. A three-dimensional imaging system for acquiring a succession of two-dimensional images of a target volume represented by an array of pixels I(x,y,z) into a three-dimensional image represented by a volumetric image array V(x,y,z) comprising:

scanning means to scan said target volume and generate a succession of two-dimensional images thereof; and processing means in communication with said scanning means, said processing means including:

means to convert the two-dimensional images of the target volume into an array of pixels I(x,y,z);

means to transform said array of pixels I(x,y,z) into an image array R(x,y,z) so that each z-slice A(x,y) of image array R(x,y,z) provides sufficient image data to construct an image slice;

means to extract each z-slice A(x,y) of image array R(x,y,z) and compute the position of each pixel of each z-slice A(x,y) in a volumetric image array;

means to compute and store a gray level or color for each of the pixels of each z-slice A(x,y);

means to map the computed gray-levels or colors into corresponding pixels of said volumetric image array V(x,y,z); and means to compensate for at least one hardware offset affecting said array of pixels associated with said scanning means.

12. A system as defined in claim 11 wherein said scanning means includes a probe to transmit signals to and to receive signals from said target volume, said probe being axially rotated to scan said target volume and wherein said at least one hardware offset includes image-tilt offset, displacement offset and tilting offset.

13. A system as defined in claim 11 wherein said scanning means includes a probe to transmit signals to and receive signals from said target volume, said probe being moveable along a path to scan the entire target volume and wherein said at least one hardware offset includes displacement offset and tilting offset.

14. A system as defined in claim 11 wherein said processing means further includes means to compensate for shadowing effects affecting said three-dimensional image.

15. A system for displaying and manipulating a displayed three-dimensional image represented by a volumetric image array V(x,y,z), said three-dimensional image having a plurality of surfaces, at least one of which is visible on a display at any given time, said system comprising:

detection means to contextually interpret actuation of a user input device to detect a desired manipulation of said displayed image selected from a group of desired manipulations including (i) rotation of said displayed image about an arbitrary axis; (ii) translation of a selected visible surface of said image; and (iii) rotation of a selected visible surface of said image about an arbitrary axis; and processing means in communication with said detection means, said processing means acting on said volumetric image array in response to the user input device and updating said displayed image in accordance with the selected desired manipulated thereof.

16. A system as defined in claim 15 wherein said processing means examines the volumetric image array V(x,y,z) and establishes a model in the form of a convex polyhedron having a plurality of planes which substantially encompasses said image array, the visible surfaces of said image array being texture-mapped onto the visible planes of said model when said three-dimensional image is displayed.

17. A system as defined in claim 16 wherein once a model has been established for a volumetric image array by said processing means, said model is stored in memory with said volumetric image array and is retrieved when said volumetric image array is processed.

18. A system as defined in claim 16 wherein movement of said user input device moves an indicator over said display, said detection means detecting the position of said indicator and monitoring actuation of said user input device to detect said desired manipulation.

19. A system as defined in claim 18 wherein said detection means detects desired manipulation (i) when said indicator is positioned outside of said model and said user input device is actuated.

20. A system as defined in claim 18 wherein said detection means detects desired manipulations (ii) and (iii) when said indicator is positioned on said model and said user input device is actuated, said detection means distinguishing between desired manipulations (ii) and (iii) based on the position of the indicator relative to the boundary of a selected plane of said model when said user input device is actuated.

21. A system as defined in claim 20 wherein the planes of said model are divided into internal and external areas, and wherein positioning of said indicator in said external area when said user input device is actuated represents desired manipulation (iii) and positioning of said indicator in said internal area when said user input device is actuated represents desired manipulation (ii).

22. A system as defined in claim 21 wherein said plane is colored when said indicator is positioned in said external area to signify that actuation of said user input device will result in rotation of said selected plane.

23. A system as defined in claim 20 wherein said processing means ignores said detection means when actuation of said user input device would cause translation of a plane sufficient to collapse said model.

24. A system as defined in claim 28 where once a model is established to encompass the volumetric image array, the planes of that model represent the outer boundary of which any plane may extend.

25. A system as defined in claim 23 wherein said processing means creates a new plane when a selected plane of said model is to be translated or rotated, said new plane being congruent with said selected plane, said new plane replacing the selected plane on the display and undergoing the translation or rotation in response to said user input device.

26. A system as defined in claim 16 wherein arbitrary views of said displayed image may be saved and retrieved.

27. A system as defined in claim 26 wherein said processing means is operable to create sequences of images by interpolating between a displayed image and a saved image in response to input received by said detection means from said user input device and to display said sequence of images as an animated sequence.

28. A system as defined in claim 27 wherein the number of intermediate views in the animated sequence between the displayed image and the saved image is selectable by a user.

29. A system as defined in claim 16 wherein said processing means performs said texture-mapping at different resolutions and/or using different resampling methods depending on the state of program variables which may be modified in response to user input.

30. A system as defined in claim 16 wherein said processing means displays a representation of the three-dimensional image adjacent to or superimposed upon the displayed three-dimensional image, the orientation of the representation on the display being adjusted as the model and three-dimensional image are manipulated.

31. A system as defined in claim 16 wherein said user input device is in the form of a mouse, digitizer, light pen, trackball, keyboard or the like or any combination of the above.

32. A three-dimensional imaging system for generating a three-dimensional image of a target volume under examination, said system comprising:

scanning means to transmit signals to said target volume, to scan said entire target volume; and a processor in communication with said scanning means and receiving output signals therefrom, said processor reconstructing a volumetric image array $V(x,y,z)$ representing a three-dimensional image of said target volume from said output signals, said processor establishing a model in the form of a convex polyhedron having a plurality of planes which encompasses substantially said volumetric image array, said processor mapping said image array onto said model to form a displayed three-dimensional image having a plurality of surfaces, at least one of which is visible on said display at any given time, said processor including:

detection means to contextually interpret actuation of a user input device to detect a desired manipulation of said displayed image selected from a group of desired manipulations including (i) rotation of said displayed image about an arbitrary axis; (ii) translation of a selected plane of said image; and (iii) rotation of a selected plane of said image about an arbitrary axis; and means in communication with said detection means, to act on said volumetric image array in response to the user input device and update said displayed image in accordance with the selected desired manipulated thereof.

* * * * *